United States Patent
Klinger et al.

(10) Patent No.: US 6,867,288 B1
(45) Date of Patent: Mar. 15, 2005

(54) POLYCYSTIC KIDNEY DISEASE GENE

(75) Inventors: Katherine W. Klinger, Sudbury, MA (US); Gregory M. Landes, Northborough, MA (US); Timothy C. Burn, Northborough, MA (US); Timothy D. Connors, Hopkinton, MA (US); William Dackowski, Hopkinton, MA (US); Gregory Germino, Baltimore, MD (US); Feng Qian, Baltimore, MD (US)

(73) Assignees: Genzyme Corporation, Cambridge, MA (US); Johns Hopkins University, Baltimore, MD (US)

( * ) Notice: Subject to any disclaimer, the term of this patent is extended or adjusted under 35 U.S.C. 154(b) by 0 days.

(21) Appl. No.: 08/460,215

(22) Filed: Jun. 2, 1995

Related U.S. Application Data

(60) Division of application No. 08/381,520, filed on Jan. 31, 1995, now abandoned, which is a continuation-in-part of application No. 08/323,443, filed on Oct. 12, 1994, now Pat. No. 5,654,170.

(51) Int. Cl.[7] .......................... C07H 21/02; C12N 15/63
(52) U.S. Cl. .................................. 536/23.1; 435/320.1
(58) Field of Search ............................... 536/23.1, 24.1; 435/320.1; 514/44

(56) References Cited

U.S. PATENT DOCUMENTS 6,071,717 A * 6/2000 Klinger et al. ............. 435/69.1

OTHER PUBLICATIONS

Cecil: Textbook of Medicine, J.B. Wyngaarden et al., ed., W.B. Saunders Co., Philadelphia 1988, pp. xxxv, 1039.*
The European Polycystic Kidney Diseae Consortium, 1994, Cell:881–894, Jun. 1994.*
Orkin et al., 1995, "Report and Recommendation of the Panel to Assess the NIH Investment in Research on Gene Therapy", National Institutes of Health, Dec. 1995.*

* cited by examiner

*Primary Examiner*—Michael C. Wilson

(57) ABSTRACT

The present invention provides methods and compositions for treating cyst formation in PKD1-associated epithelial cells. Such methods encompass administering an isolated human PKD1 gene, or fragments of the gene, under conditions that result in expression of therapeutically effective amounts of all, or part of, the PKD1 protein. The invention also encompasses compositions for treating cyst formation associated with APKD.

3 Claims, 39 Drawing Sheets

FIGURE 1

```
TGTAAACTTT TTGAGACAGC ATCTCACCCT GTTCCCCAGG CTGGAGTGCA GTGGTGTGAT    60
CATGGCTCAC TGCAGCGTCA ACCTCCTGGG TCTACTTGAT CTGTAAACTT CGAGGGAAGG   120
TGTAATAAAC CCTCCTGCAA TGTCTTTGTT TTTCAAAATC TTTGTATTTC ACAGTTTAGC   180
TTCGTGGGTT GATGTTCTAT TTTGTTTTTG TGTGTGTGTG TGTGTGTTTT GTGTTTTTT    240
TTGAGACACA GTCTTGCTCT TGTTGCCCAG GCTGGAGTGC AATGGTGTGA TCTTGGCTCA   300
CTGCAACTTC CACCTCTTGG GTTCAAGAGA TTCTCCTGCC TCAGCCTTCC GAGTAGCTAG   360
GATTACAGGC GCCGCCACCA CACCCCGCTA ATTTTGTATT TTTAGTAGAG ATGGGGTTTC   420
TCCATATTGG TCAGGCTGGT CTCAAACTCC CGACCTCAGG TGATCCGCCC ACCTCAGCCT   480
CCCAAAATGC TGGGATTACA GGCGTGAGTC ACCGCACCTG GCCAATGTTC TATTTTGAG    540
AACACAACAG TTCATAATAT ATTCTACATA GACCATACCT GTTATGTGTA GATAAACAGA   600
CTCTTTTCCC ATTTAACACC TTTTGCCTTA GGTTTATTTT TCTGGTATCA ATACTGGCAC   660
ACTTACTTTG TTTGCAGTTT CCTGTCTTTT TTTTTTTTT TTTTTTTTT GAGACAGAGT    720
CTCACTCTGT CACCCAGGCT GGAGTGAAGT GGCGGGATCT CGGCTCACTG CAACCTCTAC   780
CTCCTGGGTT CATGCGATTC TCCTGCCTCA GCTTCCCGAA TAGCTGAGAC CACAACTGTG   840
TGCCACCATG CCCAGCCAAT TTTTGTATTT TTAGTAGACA CGGGGTTTCA CCATACTGGC   900
CAGGATGGCT CAATCTCTTG ACCTCGTGAT CCACCTGCCT CCGCCTCCCA AAGTGCTGGG   960
ATTACAGGCA TGAGCCACTG TGCCTGGCCT TTTTTTTCT TTTTGAGATG GAGTCTCACT   1020
CTGTCACCCA GGCTGGAGTG CAGTGGGGTA ACCTCAGGTC ACTGCGACCT CCGCCTCCCG  1080
GGTTCCAGTG ATTCTCCTGC CTCAGCCTCC CGAGTAGCTG GGATTACAGG CACCCACCAC  1140
CATGCCTGGC TAATTTTTGT ATTTTAGTA GAGACGGGGT TTGCCACGT TGGCCAGGTT   1200
GGTCTCGAAC TCTTGGCCTC ATGTGACCCG CCTGCCTTGG CCTCCCAAAG TGCTGGGATT  1260
ACAGGTGTGA GCCACTGTGC CTGGCCTGGC TTTCTTGTTT CTTTTCTCCT CTTCTAGTTT  1320
CCCCCTTTTA GGCTAACAAT TATTCACTGT TAATAAAAAC CCTCAGGTCT GTATTTTATC  1380
AAGAAACATT TCCCTCACGT CTTCTTCCCT GAACCAAACA AGATCTCTGG CACATTTTAT  1440
TTGCTCTGTC TCACCACATG GATTTTGTTT TTTGTTTCT TTGTTTTTTG AGATGGAGTC   1500
TCACTCTTGT TGCCCAGGCT GGAGTGCCAT GGCACAATCT CAGCTCACTG CAACCTCCAC  1560
CTCCTGGGTT CAAGCGATTC TCCTGTCTCA GCCTCCTGAG TAGCTGGGAT TACAGGCGCG  1620
TGGCACCACC CCCAGCTAAT TTTTGTATTT TTAGTAGAGA CGGGGTTTCA CCATGTTGGT  1680
```

```
CAGGCTGGTC TCGAACTCCT GACCTTGTGA TCTGCCCACC TTGGCCTCCC AAAGTGCTGG    1740
GATTACAGGC ATGAGCCACC ACGCCCGGCC CCCATGGTTT TTCAAATAGT TTAGAATTTC    1800
ATTTCCAGGT AACTAATTTG CTTCTTTAAA CATATGTCTT TTCTATTTAA GAAATCCTTT    1860
CTAAACAATT GCATTTTATT CCACAACCGC CTTCAAACAA TCATTGAGAC TTGGTTAATC    1920
TGTTTTGCTC ATTTGGCAGC AGTTTCTTGT GGCTGTTTCT TCCCTCCACT GGAGTCCTTG    1980
AATCTTAAGT CTGTCATTTG ACTGCAATTA AAAGCTGGGT TTGGAATACA ATCGCAGCCT    2040
TACCATCCAC CTGCTGTGTG ACCTGGTAAA TTTCTTTTTT TTTTTTTGAG ACGGAGTCTT    2100
GCTCTGTTGC CCAGGCTGGA GTGCAGTGGC ACAACCTCTG CCTCCAGGT TCAAGCGATT      2160
CTACTGCCTC AGGCTCCCTA GTAGCTGGGA TTATAGGTGC CTGCCACCAT GCCCAGCTGA    2220
TTTTTGTATT TTTAGTAGAG ATGAGGTTTC ACCATGTTGG CTAGGCTGGT CTCGAACTTC    2280
TGATCTTGTG ATCTGCCCGC CTCGGCCTCC CAAAGTGCTG GATTACAGG CATGAGCCAC      2340
CACTCCCAGC CAGTTCTTTT TTTCTTTTTT CCATTTTTTT TTTTTCGAG ACAGGATCTT      2400
ACTCTTTTGC CCAGGCGGGA GTGCAGTGGC ACAATCACGG CTCAGCGCAG CCACTGCCTA    2460
CTGGGCTCAC ACGCTCCTCC GGCCTCAGCC TCTCGAGTAC CTGGGACTAC AAGCGTGAGC    2520
CAGTTTGGCT AATTTTGGCT AATTTTTGTA GAAACGGGGT CTCGCCATGT TGGCCAGGCT    2580
GGTCTCCAAC TCCTGGACTC AAGGGATCCA CCTTCCTCCC CCTCTCAAAG TTCTGGGATT    2640
ACCGGAGTGA GCCACTGTGC CCTGCTGGCA AATTTCTTAA ACTGTCTGTG CCTCAGTGAC    2700
CTCATTTAAT AAAGGGAATA ATTGTAGCAC ACTTTTTCTA GAGCTGTGAA GATTCAATGG    2760
AATAAATAAG GCAATAAATG AATGGATGGG GAATGAAGGA TGTGGGTTTC CTCCCTCTTG    2820
TCTTTCAATA AGCTCTCACC ATCAACCTCC CATTGCCTGT TCTCTCTCTT CCCCCTCTCT    2880
CCCTCTGTCT CTCTCTCAGC CAGGAAACCT GGGGTAGGGA GGCTTGGAGC CAGCGGGTGC    2940
GTCGGGAGGC TGCGGGTACT GACTCGGGCC GCGCACGGAG ATCGCGGGAG AAGGATCCAC    3000
AACCGCGGAA GAAGGATCAG GGTGGAGCCT GTGGCTGCTG CAGGAGGAGG AACCCGCCGC    3060
CTGGCCCACA CCACAGGAGA AGGGCGGAGC AGATGGCACC CTGCCCACCG CTTCCCGCCC    3120
ACGCACTTTA GCCTGCAGCG GGGCGGAGCG TGAAAAATAG CTCGTGCTCC TCGGCCGACT    3180
CTGCAGTGCG ACGGCGGTGC TTCCAGACGC TCCGCCCCAC GTCGCATGCG CCCCGGGAAC    3240
GCGTGGGGCG GAGCTTCCGG AGGCCCCGCC CTGCTGCCGA CCCTGTGGAG CGGAGGGTGA    3300
AGCCTCCGGA TGCCAGTCCC TCATCGCTGG CCCGGTCGCG CTGTGGCGAA GGGGCGGAG      3360
CCTGCACCCG CCCCGCCCCC CCTCGCCCCG TCCGCCCCGC GCCGCGCGGG GAGGAGGAGG    3420
```

| | | | | | |
|---|---|---|---|---|---|
| AGGAGCCGCG | GCGGGGCCCG | CACTGCAGCG | CCAGCGTCCG | AGCGGGCGGC | CGAGCTCCCG | 3480 |
| GAGCGGCCTG | GCCCCGAGCC | CCGAGCGGGC | GTCGCTCAGC | AGCAGGTCGC | GGCCGCAGCC | 3540 |
| CCATCCAGCC | CGCGCCCGCC | ATGCCGTCCG | CGGGCCCCGC | CTGAGCTGCG | GCCTCCGCGC | 3600 |
| GCGGGCGGGC | CTGGGGACGG | CGGGGCCATG | CGCGCGCTGC | CCTAACGATG | CCGCCCGCCG | 3660 |
| CGCCCGCCCG | CCTGGCGCTG | GCCCTGGGCC | TGGGCCTGTG | GCTCGGGGCG | CTGGCGGGGG | 3720 |
| GCCCCGGGCG | CGGCTGCGGG | CCCTGCGAGC | CCCCCTGCCT | CTGCGGCCCA | GCGCCCGGCG | 3780 |
| CCGCCTGCCG | CGTCAACTGC | TCGGGCCGCG | GGCTGCGGAC | GCTCGGTCCC | GCGCTGCGCA | 3840 |
| TCCCCGCGGA | CGCCACAGCG | CTGTGAGTAG | CGGGCCCAGC | GGCACCCGGG | AGAGGCCGCG | 3900 |
| GGACGGGCGG | GCGTGGGCGG | GTTCCCTGGC | CCGGGACGGG | AAGCAGGACG | CGGGCCAGGA | 3960 |
| CGCTCCCAGG | GGCGAGGCTC | CGGCGCGGCA | CGGCGGGCCC | TGCTAAATAA | GGAACGCCTG | 4020 |
| GAGCCGCGGT | TGGCACGGCC | CCGGGGAGCC | GAAAAACCCC | GGGTCTGGAG | ACAGACGTCC | 4080 |
| CACCCGGGGG | CTCTGCAGAC | GCCAGCGGGG | GCGGGCGCG | GAGGCCGCGC | TCAGCTGGGA | 4140 |
| GGACAAACAG | TCGCTAATTG | GAGAGGAATT | GGGATCGGCC | TGGGCTGCG | GGGTACCCGG | 4200 |
| AGAGGTGGGG | ATGGCTGTAG | GGGGCGGCAG | CCAAGAGTTC | CAGGAGGTGT | CTGGAAAAGG | 4260 |
| ATTTGATGGA | TGTGCAAGAA | TTGGGCTGAT | GCTTAGGAAG | GGGCGATGAG | GTGGGTCCAG | 4320 |
| AAGAAGGGGG | GTCAACGGTG | TGAGCAAAGA | CCGTGAGGCT | GGAGGCTGGC | CACGGGAGGT | 4380 |
| GTGAGGGGTA | GGGGCAGGGT | GGGAGGTGGG | CTCGCGGGTG | GGCTGGGGTC | ATGAAGGGCC | 4440 |
| TCAGGCGCTC | TGCTATTGGG | TTCCAAGGCT | ATCCTGAGAA | CAGGGGTGAG | GGGGATTGC | 4500 |
| CGTGGGGGGT | TAAAGCCTTG | TCATGTTCGC | TTTCGGGAGA | TAAAAACAAC | AGGTGGCCTT | 4560 |
| TATGGAGACG | CTGCCCAGAG | CCAGGTCTGT | GCCAGGCTCC | TGTTGGGGGT | CGTCATGCGG | 4620 |
| AATCCTGACT | CTGACCATCC | GAGGCATAGG | GACCGTGCAG | ATTTGCATTT | CACAGATGAG | 4680 |
| GAAACAGGTT | TGGAGAGGTG | ACACGACCTG | TCCCAGGCAT | CACAGCCGGG | ATGTGCATAG | 4740 |
| CAGGGGTTTG | CAACTATGAG | GTGCCCAGGA | CCCAGGGTTG | GATTGAAAAG | GGCGGAGGGG | 4800 |
| ACTAAGATAA | GCAGACAGTT | GTCCCCAGCG | CTGGGGAGAG | TCTTGGGACC | AGTCTGATGC | 4860 |
| CTTGTATTTC | CCAGGCTCCA | GGCTCCTCGC | CGGGACAGTG | TCTCCTTGGG | TGCGTGCTGG | 4920 |
| ATCCCTGGGG | GACGTGGCAC | ATCCCCAGGC | TTGCTAAACA | TTGGGTGGGT | TCTGGCATTT | 4980 |
| GGTTTTGTAA | CGTTTCTGGG | TCACTCCCGC | CTGTGGCCAC | CCTTCCTTAG | GGGAGCCGTG | 5040 |
| TGTCCTTGGG | GCTTTGCTGG | GTGGTCTCGA | GGGTGGGAGA | AGAATGGGTT | CTCCTGGACC | 5100 |
| AATGGAGCCC | GTGCCCCTCG | GGGCCACATT | GCTCCTGCGC | TCCCTGACTG | CGGACGCGTG | 5160 |

```
TGTCTCGCGG CTGTCTCTGT GGAGATGGCC TCCTCCTGCC TGGCAACAGC ACCCACAGAA    5220
TTGCATCAGA CCTACCCCAC CCGTTGTTTG TGATGCTGTA GCTGAGGGCT CCTCTGTCTG    5280
CCAGGCCGGT CACTGGGGAC TCTGTCCAGG GCCTGGTGGT TCCTGCTTCC CAGCACCTGA    5340
TGGTGTCCAT GAGAGCAGCC CCTCAGGAGC TGTCCGGGAG AGAAGGGCGC TGGTGGCTGC    5400
TGAGCGGAGA GCAAGGCCCG TGTTCTCCAG GCCCTTGGCA CAGCAGTGGA GCCCCGCCC    5460
CTGCCTTGTG TTGTCCTCTT AGGCTCTGGT CCTGGGGTTT GGAGGAGGGG GACCCTGGGA    5520
GTTGGTGGCC TGTCCCAGCC TGAGCTGGCA AGATTCCGAA TGCCAGGCCC CCCAAGTGTG    5580
CAACAGGGCA CAGGGTGACC TCATGTGGGC AGGTCGGTGC TGTTCTGTAC ACACCTGGGG    5640
CCGCCGCTGG GAGAGTTCTG GAAGGTGGGG TGAGGGGACC CATGGCAAAC TAGGGCCTTA    5700
GGAAGGATGT GAAGGCCCTG GCTGGCCCCC CAGGCCACCC TCTGTGCTGT GGGGCAGCCC    5760
AGCCATTTTG CTGTCTACCC TGCAAACTCC TCCTCGGGGA GACGGCTGGG TTTTCCCCAG    5820
GGAAGAGGGG TCAAGCTGGG AGAGGTGAAG GACACAGATC ACAGCTGCTG GCAGGTGTTC    5880
AAGGGTCCAA GAGCGTTGCT GTCTGGGTGT CACCAGTAGC CTTCCTGGGG GGCTCACGCA    5940
GGTGCCTCTC CACTTGTGGC TCCCTGGCTG CTGAAGCTCA GCAGGGACAG CTGTGTCCAG    6000
TTCCAGGTGG AGGACAGCCG GGGCTTCTGA GGCCACAGCC TGCCTTGGGT TAATGATGCT    6060
GCCGAGAGGT GGTGGCTTTT GGAAAAGATG GCGTACTGCA AACGTGCTG CTCTGCGTGG    6120
CTCGAAGCTT CGTGGGGAGA CGTGGGCAGA GCCGTGGCTG ACTCACAGAC CCCCCACCCC    6180
AGAGCCTGCC CTGCCCTCCC TGCCCCGACC CTTCTCCCTC CTGACCCATG TGTTTTTTT    6240
TTTTTTTTT TTTTTGAGA CAGAGTTCAC TCTTGTTGCC AAGGCTGGAG TGCAATGGCA    6300
CGATCTCGGC TCATGGCAAC CTCCGCCTCC TGGGTTCAAG CGCTTTTCC TGCCTCAGCC    6360
TCCCGAGTAG CTGGGATTAC AGGCGTGCAC CACCATGCCT GGCTAATTTT GTATTTTAG    6420
TAGAGACAGG GTTTCTCCAT ATTGGTCAGG CTGGTCTTGA ACTCCTGACC TCAGATGATC    6480
CGCCCGCCTC GGCCTCCCAA AGTGCTGGGA TTACAGGCAT GAGCCACCAC GCCAGCCCT    6540
GACCCATGTT TTGAACCAAA TTCCAGCCAC CCTTTTATCT GCAAGCATTT TGGAGGGCAT    6600
CGCAATACTG CAGACCCACC TAACACAACA GACAGTTCCT TCATGCCACC GAAGGCCTGG    6660
TGTGTTCACA TTTTTGGTTT AATAGTTTGA ATTAAGAGCC AAATAAGGTC CACACACTGC    6720
AATTAGTTGA TGTCTTTTTT TTTTCTTTT TTTTTTTTT TTTGAGACGG AGTCTTGCTC    6780
TTGTCTCCAG GCCGCAGTGC AGTGGCATGA TCTCAGCTCA CCGCAACCTC CGACTCCCTG    6840
GTTCAAGCGA TTCTCCTGCC TCAGCCTCCC GAGTACCTGG TAGCTGGGTT TACAGGCATG    6900
```

| | | | | | |
|---|---|---|---|---|---|
| CACCACCGTG | CCCAGCTAAT | TTTTGTATTT | TTAGTAGAGA | CGGGGTTTTA | CTGTGTTGGC | 6960 |
| CAGGATGGTC | TCGATCTCCT | GACCTCGTGA | TCTGCCCACC | TCGGCCTCCC | AAAGTGCTGG | 7020 |
| GATTACAGGC | GTGAGCCACC | GCACCCGGCC | AATGTCTTTT | AAAAATATAT | ACTTTTTTTT | 7080 |
| TTTTTTTGAG | ACGGAGTTTC | GCTCTTGTTG | CCCAGGCTGG | AGTGCAGTGG | CGCGATCTCA | 7140 |
| CCTCACGGCA | ACCTCCGCCT | CCCGGGTTCA | AGTGATTCTC | CTGCCTCAGC | CTCTCCAGTA | 7200 |
| GCTGGGATTA | CAGGCATGTG | CCACCATGCC | TGGCTAATTT | TGTATTTTTA | GGAGAGACGG | 7260 |
| GGTTTCTCCA | CGTTGGTCAG | GCTGGTCTCA | AACTCCTGAC | CTCAGGTGAT | CCGCCTGCCT | 7320 |
| TGGCCTCCCA | AAGTGTTGGG | ATTACAGGTG | TGAGCCAACG | CGCCCAGACA | AAAATATATG | 7380 |
| TGTGTCTTTA | AGGCTGGTCA | AGCAAAGCAG | TAGGACTGGA | GAAAGAATGA | GAATTCTAC | 7440 |
| CTGGCTGTGA | TCAATTCGTT | GTGAACACCA | CTGTGCTTGG | ACCAGCTAGC | TGATGTCTTT | 7500 |
| TGTTTTGTTT | TGTTTGAGAC | GGAGTCTGGC | TCTGTCACCC | AGGCTGGAGG | ACAATGGTGT | 7560 |
| GATCTCGGCT | CACTGCAGCC | TCCATCTCCC | GGGTTCAAGC | GATTCTCCTG | CCTCAGCCTC | 7620 |
| CTGAGTAGCT | GGGATTAGAG | GCGCGCGCCA | CCACGCCCGG | CTAATTTTA | AAAATATTTT | 7680 |
| TAGTAGAGAT | GGGGTTTCAC | CATGTTGGTC | AGGCTGGTCT | TGAACTCTTG | GCCTTAGGTG | 7740 |
| ATCTGCTTGC | CTCGGCCTCC | CAAAGTGCTG | GATTACAGG | TGTGAGTGAT | GTATTTTATT | 7800 |
| TATTTATTTA | TTTATTTATT | TTTATTATTT | GAGATGGAGT | CTCACTCTGT | TGCCCAGGCT | 7860 |
| GGAGTGCAGC | AGTGCCATCT | CAGCTCACTG | CAAGCTCCGC | CTCCTGGGTT | CACGCCATTC | 7920 |
| TCCTGCCTCA | GCCTCCTGAG | TAGCCTGGAC | TGGTGCCCGC | CACCATGCCC | AGCTAATTTT | 7980 |
| TTGTATTTTT | AGTAGAGACG | GGGTTTCACC | GTGTTAGCCA | GGATGGTCTG | GATCTCCTGA | 8040 |
| CCTCGTGATC | CTCCCGCCTC | AGCCTCCCAA | AGTGCTGGGA | TTACAGGCTT | GAGCCACCGC | 8100 |
| CTGTCTTTTA | AATGTCCGAT | GATGTCTAGG | AGCTTCCCTT | CCTCTCTTTT | TCCTTGTGCA | 8160 |
| ATTTGTTGAA | GAAACTGGCT | CCTGCAGCCT | GGATTTCTCG | CTGTGTCTTG | GGGGTGCCAC | 8220 |
| CTCCATGGTG | TCACCTCCGT | GGTGCTGTGA | GTGTGTGCTT | TGTGTTTCTT | GTAAATTGGT | 8280 |
| CGTTGGAGCC | GACATCCCAT | TGTCCCAGAG | GTTGTCCTGG | CTGGCACTGG | CCTAGGTGTA | 8340 |
| GATGTCATCA | GCTCAGGGCC | CCCTGCTCTA | AAGGCCACTT | CTGGTGCTGG | TTGCCACTCA | 8400 |
| CCCTGGCTGG | GGGTCACCTG | GGTCTGCTGC | TGTCTCGCAA | ATGCTGGGGT | CCAGGACTGG | 8460 |
| GCACATCGAG | GGACTTGGTA | GGTGCTTGGT | TCACTGATGT | AAAATATAGG | AGCACCCGGG | 8520 |
| GCCTTGCCCT | TTCCCACCTG | CATCCCTGAA | TGACAGGAGA | GTGTGGGAGA | GTGTAGGGAC | 8580 |
| AGCAGGCGCA | GACCCCGGGG | CCCCTGCCTG | GGATTGGCGT | CGGGGAAGAC | AGGCATTCTG | 8640 |

| | | | | | | |
|---|---|---|---|---|---|---|
| GAGCGACCCC | TAGGCCTGAT | GCCTTAGAGC | GCAACTGCCA | GAGACACAGC | TTCCTTGGGG | 8700 |
| GGCTGGCCAG | GCCACGGAGG | GGCCCTGGCT | CCCATTTCTG | GTCCCTGGAT | CCTGAGAGCG | 8760 |
| AGGACTAGGG | ATTGTCACCA | AGGCCTCCAT | GAGCCCTCAG | CAGAAGGAGG | GCCACCCTCG | 8820 |
| AGGGCTCCGT | TATCACTGGA | GCCCGCGTTC | AACCAACACG | CAGATGATTC | TCCAAGGACA | 8880 |
| GAGATGGATG | ATGGGGAGGG | GGCTGGCCTG | GAAGGACCCC | CAGTGCAGGT | GACATTGAAG | 8940 |
| CCAGGTTTCA | AAGCTCCCAC | AGGGAGCTGC | CCAGAGAGAG | TCCCCAAGGG | GCAAGGTGAC | 9000 |
| TCGGGGGCAG | GGGTAGGGCC | TCTGTCAGGA | GAGCCTAGGA | GAGGCCTGTG | TCTTCTAGGA | 9060 |
| AGAGCCCTGG | CAGCCGAGCG | GAGGCAGTGG | TGAGGACCTG | CATCCTGCAT | GTCCAGCTGG | 9120 |
| CCTCACCCGG | GGTCCCTGAG | CCGGGTCTTA | CGTGGCTCCC | GCACTCGGGC | GTTCAGAACG | 9180 |
| TGCCTGCGTG | AGAAACGGTA | GTTTCTTTAT | TAGACGCGGA | TGCAAACTCG | CCAAACTTGT | 9240 |
| GGACAAAAAT | GTGGACAAGA | AGTCACACGC | TCACTCCTGT | ACGCGATTGC | CGGCAGGGGT | 9300 |
| GGGGGAAGGG | ATGGGGAGGC | TTTGGTTGTG | TCTGCAGCAG | TTGGGAATGT | GGGGCACCCG | 9360 |
| AGCTCCCACT | GCAGAGGCGA | CTGTGGAGAC | AGAGAGCACC | TGCAGGTCAT | CCATGCAGTA | 9420 |
| TCGGCTTGCA | TCCAGATCAT | ACAGGGAACA | CTATGATTCA | ACAACAGACA | GGGACCCCGT | 9480 |
| TTAAACATGG | ACAAGGGGTC | ACTCACGCCT | GGAATCCCAG | CAGTTTGGGA | GGCCAGGGTG | 9540 |
| GGTGGATCGC | TTGAGCCCAG | GAGTTTGACA | CCAGCCTGGG | CAACAGGGTG | AGACCCCGGT | 9600 |
| CTCTAAAAAA | TAAAAGAACA | TTGGCCGGGC | GTGGTGGTAT | GCATCTGTGG | TCCCAGCTAT | 9660 |
| TCAGGAGACT | GAGGTGGGAC | ATCACTTGAG | CCGAGGAGGT | CAAGGCTGCA | GTGAGCTGTG | 9720 |
| ATCACACCAC | TGCACTCCAG | GCTGGGTCAC | AGAGCAAGAC | CCTGTCTCAA | AAAAAAAAAA | 9780 |
| AAAAAAAAAA | AAAAATCACA | GGATCTGAAC | AGAGATTTCT | CCAAAGAAGA | CGCACAGATG | 9840 |
| GCCAACAGCG | TGTGAGAAGA | TGGTCGGCCT | CATTAGTCAT | GAGGGAAACG | TAAATCAAAA | 9900 |
| CCACTGTCCA | GCCGGGCGCG | GTGCCTCACG | CCTGTAATCC | CAGCACTTTA | GGAGAGCAGA | 9960 |
| TGGCTTGAGG | CCAGGAGTTT | GAGGCCAGCC | TGGGCAACAT | AGCCAGACCA | ATAAATAGAT | 10020 |
| ATTAGTGGTG | GCGCCTGTAC | TCCCAGCTAG | TTGGGAGGCT | GAGGGGGGAG | GATTCCCTGA | 10080 |
| GTCTATGAGG | TTGAGACTGC | AGTTAGCTGT | GATGGTGCCA | CTGCACTCCA | GCCTGGGCGA | 10140 |
| CTAGGAAACG | GTCTTTAAAA | AAAAAAAAAA | AAAACAGGGT | GGGCGCGGTG | GTTCACGCCT | 10200 |
| GTAATCTCAG | CACTTTGGGA | GGCCAAGGTG | GGGGGATCAC | AAGGTCAGGA | GTTTGTGACC | 10260 |
| AGCCTGACCA | ACATGGTGAA | ACCCCGTTCT | ACTAAAAATA | CAAAAATTAG | CGAGGTGTGG | 10320 |
| TCGTGGGCGC | CTGTAATCCC | AGCTAATTAG | GAGGCTGAGG | CAGGAGAATC | ACTTGAACCC | 10380 |

| | | | | | |
|---|---|---|---|---|---|
| GGGAGGCGGA | GGTTGCAGTG | AGCCAATATC | ACACCACTGC | ACTCTAGCCT | GGTCAACAGA | 10440 |
| GCGAGACTCT | GTCTCAAAAA | AAAAAAATGC | TGAGCGTGGT | GGCGCATGCC | TGTAGTCTCA | 10500 |
| GCTACTTTGG | GGGCTGAGGC | AGGAGAATCG | CTTGAACCTG | GGAGGCAGAG | GTCGCAGTGA | 10560 |
| GGCAAGATTG | CACCATTGCA | CTCCAGCCTG | GGAGACAGAG | TGAAACTCTG | TCTCAAAAAG | 10620 |
| AAAAGGTCTA | GGAAGAGTCC | GCACCCTCTC | CCCGCGGTGG | CCACGCCGGG | CTCCGCGCTG | 10680 |
| AGCCCTCTGT | GTTCTTGTCT | CTCCATACCT | CATCACGGCA | CCGCAGGGTT | GCAGCCACTC | 10740 |
| CTGGTCTCAT | TTTACACACC | AGGAAATTGA | GGCTCTTTGA | GAAGCCGTGG | TGATGATTTC | 10800 |
| ATCAGCATGC | TCTGGGGCAG | ACCCCTGCAG | CCGCACAGGG | TGCCTGGGCC | CCACACTAGT | 10860 |
| GCCCTGGTTT | ATAGACAGAC | AGAGGTGGCA | GTGGCGCTTC | CGAGTCGGGC | TGCGATGTGC | 10920 |
| TTGCACTCCC | CGAGGGGCTG | AGGGGCCCTG | CGCCCAGGTG | CAGCTGCTTG | GGTGCTGCCA | 10980 |
| GCCCCTCCCA | CCTCTCCCTC | CCTGCCAGCC | CCTCCCACCT | CTCCCTCCCT | GCCAGCCCCT | 11040 |
| CCCACCTCTC | CCTCCCTGCC | AGCCCCTCCC | ACCTCTCCCT | CCCTGCCAGC | CCCTCCCACC | 11100 |
| TCTCCCTCCC | TGCCAGCCCC | TCCCACCTCT | CCCTCCCTGC | CAGCCCCTCC | CACCTCTCCC | 11160 |
| TCCCTGCCAG | CCCCTCCCAC | CTCTCCCTCC | CTCCAGCCCC | TCCCACCTCT | CCCTCCCTGC | 11220 |
| CAGCCCCTCC | CACCTCTCCC | TCCCTGCCAG | CCCCTCCCAC | CTCTCCCTCC | CTGCCAGCCC | 11280 |
| CTCCCACCTC | TCCCTCCCTG | CCAGCCCCTC | CCACCTCTCC | CTCCCTGCCA | GCCCCTCCCA | 11340 |
| CCTCTCCCTC | CCTGCCAGCC | CCTCCCACCT | CTCCCTCCCT | GGCTCATCCC | TGCTGTGTCC | 11400 |
| CTTCTCTCTA | GTTTCCTGTT | CAGTTTCAGG | AAGGAGGCTG | GGAACCCAGA | TGTAGGGAAT | 11460 |
| TTGCGCCCTG | GAGTCAGACC | TGGGTTCACG | TCCCAGCGCC | TCCACCTCTG | GTGTGACCTT | 11520 |
| GGTCCAGTCT | CTCAGCCTCA | GTTTCCTCAC | CTGTAAAGTG | GCTCCATGA | TTAGATGCAC | 11580 |
| CCTGCAGGGC | AGTGTAGCAG | TGACCTGGCT | CAGCCACTGG | CAGCCCCAAC | AATCATACCT | 11640 |
| TGTTAAAGTA | GCTCTGTCGG | TTCCCTCAGG | GGTTCCGGGG | GCCCATTCCC | CTGTCCTCCA | 11700 |
| TGCACTGTGA | GACCTGCCCT | GCCACAGAGC | AGAGTGTAAC | AGCCTGAGGG | TGAGAGCCAG | 11760 |
| ACACTGTGCC | TGTGCTTAGA | CCAGACACTG | GACGACGGGA | GCCAGTGCAG | CCTGGGCGGG | 11820 |
| TGGACTCCTA | TGGACCCCTC | AGCACCCAGC | CTCGGTGCCT | TCAGCGCAGG | GCCGCGTGGC | 11880 |
| TGTGGGGGCT | CACAAGACCC | GGCCCACTCC | TGCTTGTGCC | TACATCTGGG | TGTTTGCCCA | 11940 |
| TTGGTGCCTT | TTGACGCGTT | CTGGTGTGTG | TGAGACGTGC | GGGGCTGGGA | AGTGTTGGCA | 12000 |
| GAGCCGCGAG | TACCGTCCTC | ACTCCTTTTG | TTCTTTTGAC | GTAAGCTGGC | GAGTGGCACT | 12060 |
| GCCTGAGTTC | CGCTCAGTGC | CCGCCCTGAT | GTGCGGACCC | CGCTGCATTC | TTGCTGTTAG | 12120 |

```
GTGGTGGCGG TGTGCGCTGT CGCTGGTGGG CACCGAGAGT CTTTGGGAGC TTTGGGGAGG    12180
TTGTGCCAAG CCTGAGCCTC GACGTCCCCC TTCCCGGCTT TCTGTTGGCT CTTCTGAGGC    12240
CAGGGCATCT CTATGAGGGC CTCCTGCTGG AGCCGTCTCT GTGGATCTCC TCTGCCATCC    12300
TGGCCCATGA GTGGGTGATG CGCTGGCCAC CATCTGGTGA CAGTGGCCGG GCACCGCTGC    12360
CAAATGTGGG TCCCGCATCT GCAAGCCCCT CCCTGGGTCC CCTAGGGTAT GGGGTGGTTC    12420
TGCCACTGCC CTCGCTCCCC CACCTTGGGG TGCCTCTCCC CCTGCTCGTG GGGGAGACCC    12480
TGCCTGGGAT CTGCTTTCCA GCAAGGAATA TACTTTGGAG GGAGACACAC ATGTTCTTTT    12540
CTGGAGCTCT GCAGTGGCCA CGGCAGCCCA GCCCGCCAAG CACCCTGGAA TGAAAACATC    12600
CCGCTGCTGT CTGGGCCTGG CCTGCACTCT GCTGCCTGCG CTCCAGCTGG CTGAGGCCGG    12660
GCACGTCTGC GGGCACAGCA GCGGGGGCGC CACAGTCTCC CTGCAGAGTG AGCGCAGCTG    12720
GAAAATGCAG CTCACGCCCT TCCCAGAAC ACCTCGCTCT TCATGGCTTG GCAGCTGTCC    12780
TTGCCTAGGG GCCAGGGTGC CCAGGCACTG GTGGCAGGAG AAGGGCTACA TCTGGGGCTG    12840
AGGCGGGCTG GGTCCTTTTC TCCCTGCAGC TCCCGAGGCC CAGCCCTGGC CCAGCCTGGC    12900
ATTCCTGACC TTAGCAGCGC CATGATCTGA AGACAGGCTG GCTTCTGTGA GGCCACCTCA    12960
GAAAGGGCTT TGTGCCCAGG CAGAGGCGGA AGCCAGCTCT TCCTTCTGGT TGAGGCAGGA    13020
ATGAGGCCAG CGCTGGGCAA GCCCATGCCC AGGGAACGTC ACAGCTGTGG GAGTACAGGG    13080
GCTCCGGGTT CTGAGCCCGT CCACTGTGCA TCGTGGCCCT GGCCTCAGGA TGGCTCGTAC    13140
CATCATTGGC TGTGCCCACA GCCGAGTGGG TGATGGGATT CCGGCTGCCC CGCTGGATCT    13200
GTGCTGCTGC CCTCTCCAGG GCACTGCTGT GCCCGCACAG CCGGGCGCAG ATGGCCAGTT    13260
TGCTTGCCCC CCCCCCCACC ATCCTCTTCC TACCTTGGCT TCCTCCATTG ACACACTGGA    13320
CCCTGCTGGC TGCCCGGGGA GGTGTTTGGG GGATGGTGTT GGGGGAGGAG GAGGGCCCCT    13380
TGAGCCTCAG TGTGCCCATC AGGAGCGTAA GGTCAGTGCA GCACCTGCCC ACACAGGCTG    13440
TGAAGGGTGG GAGTGGAGAG GGATGCAAGG GGGTCACAAC GCCTGGCTCC ATGTCAGCTG    13500
CGTGCAGGGG CACCAGGAGC CGGCCCTCAT TCTCCCCTTG AACTGGAAGG GTGGCCCCGA    13560
CCCCAGCGGC AGGTAGCATA CGTATGAAGC GCTCTCCTTC CTACACCCCA CAGGTGGGCT    13620
CGTCTCCAGA CGGCCCTTTT TGAGCTGGCT GTGTTTTCC ATCTGTGTAG GCAAGGACAT    13680
CGCAGACTCC CCTTTCTCAT CTCCCTCGTT CAGCCTCCGA GGCCGGAGTC TCCATCCCTG    13740
TGCCTGCCTG TGGGTCCCGG GAGGACCTGA GGCTGCCCAT GTCACCCCCG GCATCTCATC    13800
CTGGGGACAG TTCAGCCGTG GGAGGGATCT GTAAGGACAG AATGCCGCTG AGCCTGGGGC    13860
```

```
TCCCCAGCTA GTCTCACACC CCGTGTCTGG GACCCAGAGA CCCTCGTGCA GGGCTCTGTT   13920
GCTTGGGGCC TGGCAGCCTC GTCCTGTATC AGAGGCTGCC ACCCCACCC  CTCGTGGGC    13980
CAGGGTTGTG GCCGGCCTCC CTGGCCCTCC CCATGGAAGT GGTAGGCGGA GCCAGCAGCC   14040
ATCTGCCCAG CCCGGGGCTG CACTGTTTTT TTTCAAATGA GCACCGTCCC AAACTGCAGC   14100
CCGTTAATTT AAACAGGATC ATTTCCGGCC CTGGAAGCCG CCTCACTCTC CTTAAATAGA   14160
AAGGAGCACA GCGCAGAGGG AAACAGATGA GGTCATGGCT CGGCTGGCCC AGCGAGGAAG   14220
GGGCCGCAGT GGGGGTGGCA CTGCCGCCTG TCCCTGTCC  TCTCCAGCGC CCACACTGCA   14280
GCCCATTTCC TCACCCTGGG CCTGCTCTCG GGAGGACGG  GCCTGGGGGT CCTCTTGCTG   14340
GGCGGAGGGG AACCAGCTCC TCCAGGAGAG GACGGGGCCT GGCAGGGGGC ATGGGCCTC    14400
CCTGGGTCTG GCGTCCTGTC CTGCCCCTGC CGAGGGAGGA GCGGTTACAT AAGCTCCGCA   14460
CGCGGCCCCT CCGAGCCGGT CCCCCAGCC  CAGTTTCCAG TGAGGCGGCC AGCGCGGGCG   14520
GGGGTGCCGG GCCTGGCGCA CACCCGCTGC TGACCACACG TGTCTGGAAT GTGCAGATGT   14580
TTCTTTGGGG GCTCCGTCCG GCCCCAGAC  CCCACTCAGC ATCTGGTCTG GGGAGTGGGC   14640
GCCTGGGGCA CTCAGCTCTG AGTGTGAGAC TCTGAGGCAG GTCTGGTTTG TCTGGGGCCA   14700
TTCCCTCTGC TGTGGATTGG GAGGGCCCCG GGAGCTGCCC CACACCCAGG GAAGTTCTCC   14760
TCAGTCCCAC TGTTGCATTC CCCGACCCCG GCTCCCCCGG CCCAGGAGCG CCTGTGGGGC   14820
AGAAGGCCCA GCCCCAAGAC TTCCCGGCCC TGCCAGCCTC AGGCTTCACC CACCCTCGCG   14880
CCAACTGTGG GCAGAGCCCA GGGGAGGGC  AGGAGAGCCA GCGCCTGGCT GGGAACACCC   14940
CTGAGGGGCC GAGGCTCCAG GGCGAGGGGG CCCGACCTGG GGTTCACACG CCCGGGTGGC   15000
GGGCAGACCC GCTGCAGCAT GAGACACGTG TCAGCTACCT CGGGCCGGCA GGCTGGCCCT   15060
GCTGCCCACA GCCCTGGGAC GTGGCCCCAC CTGTGACGGG TGTGGAGGGG CAGCCTCCAG   15120
GCCTGGCCAC ACCCTCTGCT GTTGCTGCTC CTGCTCCAGG ATTGGCAAGG GTGCTGGGAA   15180
GGGGTGAAGA CCCGTACTGT GGCCACACAC CTGGGACTTC CTTCTCCACC CAGTGGTGCC   15240
CCAGCAGCCG CTAACGAGCC CGCTGGGTCC CACGCTAGGA TGGTCCTAAC TCCTCCCGCC   15300
TTCCAGATCG GACGCTCGGC GCTGGGGACC CCTTGTGTCC CGGGGCTGGG GACCGTCCT    15360
GCCCCCATGG GGGTGTACTC CTCCCGACAA GCTTGGCTTC AGCTTCCCTG GGAGCACATC   15420
CTGGCCCTCG GCACCCATC  AGGCTGTCCC TGTGCACCTG GCTCCCACCC TTCCAGCTCA   15480
TAGCAGGAAC TGGGGTGAGG AGTGCGTGGG GCAGCAAGGG CCTGGACCC  CAGAGGACCC   15540
TGCACTCTGC TCTGTGCTCT TGCCTGGGCT TAGGGCCGCT CGGTGGTCCT GCTGCCAGAT   15600
```

```
GCCTGGGCCC TGCTGTGTCC CCCATCCTTG CAGGGAACCA GAACGTGGGG GCAGGGCATC   15660

AGACAGCGGC GATGATGTCA CCTGGCGGGT GCAGAGGAAG CCCGAGGGGC GGGGTGGGGG   15720

GGCTGGCGCG AGGCTGCCTG GCTAGGCCTT GGCGTTCCCC CAGAACGGCG ATGGCAAAAG   15780

CAGATGGAGA CGTGAAAAAG TACGGGAGCA AGCGAGGTGA GGACTCCACG GGACCCCTG    15840

TGCTGTTCCC TGTCCTGAA  GCCCACACCT GAGTCCTGCC CAGGGCAGAT GCTTCCACAC   15900

CCAGGGGGCA CCTGAGTCCT ACCCAGGGCA GACGCTTCCA CACCCTGGGG GCTGGGGAC    15960

TGCACCTGGC TCCTGTCTGG GCCCCAGCTT CATTCCACTG CCCTGGGCCC TGGGAGCTCG   16020

GCCGAGCGGG GTCCCCAAGA CCTTGCTGCA TTTCTGGGCC TTGGGCTGGG GTGAGGGCCG   16080

GGAGAAGGAG CCAGCCTGGA GCCTGGCACG CAGGGAGTGC ATGGCCAGAA CCGGTGACAG   16140

GCAGGGCTGC CTGCTGGCGT GGAAGAAGTG TCCATGGCAC CCCCAGGCCT GGTTCACAGT   16200

GGGATGGGCG GGGAGCCGGG GGGCTCTGGG GTCCTCGGCT GACCTGCCCC CACCCCTGCC   16260

CTGGCTTGTC AGCTCCCAGC AGCAGCCACT CTTGATGGAT TTTCCAGAAA ATGAGGTGTG   16320

GCCAAACATC TTCAGGCTTT TCCTTCTTTC CTTTCTCCCG TGGCCTGGGT GGGAGCTGCT   16380

CCCCATGCCT GGGGGCAGGT GCGAGAGCCT GTGCCCCTCC CTGGGGCAGT TTCACAGCTG   16440

TGTCCCTTCC AGGGGGCCTG CCTGTGTTCA CCGTGGCCTC TGCAGCACCT CTCGCCCCTT   16500

AGGGCTCCTG CGCCTCGGGT CCCGGTGCCT CATTTCTCCC TAAAGCATTG GTTCTGCTGC   16560

CGCCGCAGCC GCTGGAAAGT CCCTCCTCAG GTCTAACTGC AGTTCCTCAC GGCACAGTGT   16620

TCCCCCTCGG GCATGGTGCT TGGGCAGTGG GTGTGAGTCC AGCTGCCTCA CCCTGTCTCG   16680

AGAATGGCCT CTTGCTGGTC TCCCAGCCAC CACCCTGTCC CACCCCACGG CGGGGATGGT   16740

GTGGATGCCT AGCAGCGCGG CTGTGGGCCC ACCCATCCTT ATGGGCAGTG GGAGCACCT    16800

CAGCCCGTGT CCCTACCTTG GTGTAGAGGA GGGGACGGCA GAGAAGCAGG GTTCAGTTAG   16860

GGGGGAAGTG GTGGCCCTGC CGGAGGGGCC GTTCCCTGTG TGCCTGGCCC CCAGATCCTC   16920

TCCCCTCCCG GAGCCCAGGG CACAGGCATA GGCTCTCTGA GTGTCCCACA GCCCCTGGGG   16980

GAAGGGAACT GCACCCCCAA CCGTGCCCTC CATCCGCAGA TGGAACGAGA AGCTCCGGGA   17040

GCCAGTGCCC AGCGTCTCAT CTGTCTGGGC ACCCAGCCCA GGTGAGGGCC TGGCTCCACC   17100

GTCCGTGGCT GGTGCTGCTT CCTGGCACGG AGAAGGCCTC GGCTGCTCTG TCCCCTCAGC   17160

TGGGGTGGCC TCTGGTCCCC TTCTTTGTTG GTTCCCTTCT CAAGCTCTTG CCCTGGCCCC   17220

GGGCCCCACC GGGCAGCCTG TGTGTGCGTC TCTCCTGCGC CGGGTAGGCT CCTGTGGGAG   17280

CGGAGCTCCG GTGGGAGGAG CAGGGCTGGA GGCTGGCAGG GGCTGGGCGG GTGTTCAGGG   17340
```

| | | | | | |
|---|---|---|---|---|---|
| ATGGAGGCCG | CCCCGGCTTG | GGGCTGGCTG | CCGGGTGGTC | ATTGCTGGGA | AGAGCAAGTC | 17400
| TAGGCGGAGG | CACCTGCTGG | GTCACTCGTG | GGGAGGGTGA | CACCTGGGGA | AGTAGAGGCC | 17460
| CGTGGCAGGA | GGTGAGGCCT | CGGGGTCCTG | GGGAGCAGGG | GGGTGGTGTG | CAGACCTGCG | 17520
| GAGCCATAGT | CCTGTGCCAG | GAGCACTACT | GGGAGTGCGT | GGGACCAGGA | GGGGTGCCCA | 17580
| GGGTGGGCGG | CAGAGTGACC | CCCGAGGTGC | TTGAGGCCGA | GGGGAGGTGG | AGTTCTCGGT | 17640
| TTGCCCCAGC | TCTCTGTCTA | CTCACCTCCG | CATCACCAGC | TCCAGGACCT | GGTTTGTAAC | 17700
| TCGGGCAGCT | CTGAAAAGAG | AGACATGCTG | CCGCCCTGTG | GTTTCTGTTG | CTTTTTCTTC | 17760
| ACTGACTACT | GACATGGGAT | GTTTTTCCTA | CGGCTGTGAC | CAATTGTGCT | TCTTCTAATT | 17820
| GCCTGGTTTT | TCTTTTTTTG | TTTTTGGAGT | TTTCTCTTTC | TTTCCTCCCT | CCCTCTCACC | 17880
| CTCCATCCTT | TTTTTTTTTA | TTTTTATTTT | TTGAGATGGA | GCTTCACTCT | TGCAGGATGG | 17940
| GGTGCTGGAG | TGCAGGGGTG | CGATCTCAGC | TCACTGCAAC | CTCTGCCTCG | CGGGTTCAAG | 18000
| TGATTCTCCT | GCCTAAGCCT | CCTGAGTAGC | TGGAATTACA | GGTGCTTGCC | ACCACGCCCG | 18060
| ACTAATTCTG | TAGTTTTGGT | AGAGACAGGG | TGTCTCCGTG | TTGGTCGGTC | TGGTCTTGAA | 18120
| CTCCTGACCT | CAGGTGATGC | GCCCGCCTCA | GCCTCCCAAA | GTGCTGGGAT | TACAGGCAGG | 18180
| AGCCATTGCA | CCCGGCTCTT | TCCCCTTCTC | CTTTTCTTCT | CTCTCTCCTC | CCTTTCTTTC | 18240
| TTTTCTTTTC | TTTTTTTTTT | CTTTTGAGAT | GGAGTCTCGC | TCTGTCACCA | GGCTGGATTG | 18300
| CAGTGGCGTG | ATCTTGGCTC | ACTGCAACCT | TCGCCTCCCG | GGTTCACGTG | ATTCTCCTGC | 18360
| CTCAGCCTCC | TGAGTGGCTG | GCACTACAGG | CTCCCGCCGC | CATGCCCGGC | TAATTTTTGC | 18420
| ATTTTTAGTA | GAGACAGGGT | TTCACCCTGT | TGGCCAGGAT | GGTCTCGATC | TCTTGATCTC | 18480
| ATGATCCACC | CACCTTGGCC | TCCCAAAGTT | CTGGCATTAC | AGGAGTGAGC | CACCGTGCCC | 18540
| GGCCATCTTT | CTTTCCTTGC | TTTCTCTTTG | TTTTCTTTCG | AGACCGGGTC | TTGCTCTGTC | 18600
| GCCCAGGCTG | GACTGCAGTG | GCACAATCAT | AGCTCACTGC | AGCCTCGACT | TCCCTGGCTC | 18660
| AAGCGATCCT | TCCTCCTCAG | CCCCCCGAGT | AGCTGGAACT | ACAGTTACAC | ACTACCATGC | 18720
| CTGGCTGATT | CTTTTTTTCC | TTGTAGAGAT | GGGGTCTTGC | TATGCTGTCC | ATCCTGGTCT | 18780
| CAAACTCCTG | GCCTTCCCAA | AGCACTGGGT | TTACAGGCAT | AAGCCACCAC | ACCCAGTTTC | 18840
| CTTTTCTTCT | TTTTAACTGG | AATAGTTGAC | GTTTTCTTTA | TTAGCTGTGT | GTCAGGAGGG | 18900
| TATTTTTGGC | CTTTAGTATG | TCGTGTAAGT | TGCTAGTGCT | TTTCTGAGAT | TGTAGTTTGT | 18960
| TTTCTAATTT | TATTTATATT | TTGCGTAGAA | GTTGTGTATT | TTAGATGGAG | TTAGGTCGGC | 19020
| TGGTCTTTGA | TGTTTTATTT | ATTAATTATG | TATGTATTTA | TTTATTTTTG | AGGTAGAGTC | 19080

```
TCGCCGTTTC ACCCAGCCTG GAGTACAGTG ATGCGATCTC AGCTCCCTGT AGCCTTGACC    19140
TCTCTGGGCT CAAGTGATTT TTCTCTCCTC TACCTCCCGA GTACTTGGGA CCCCAGGCGC    19200
ATGCCGCCAT GCCTGGCTAA TGTGTATTTT TTGTAGATAC GGGGTCTCAC TGTGTTGCCC    19260
AGGGTGGTTT CAAAATCCTG GGCCCAGGCG ATCCTTCCGT CTCAGCTCCC ACGGTGCTGT    19320
GTTACCGGCG TGTGCCCAGT GCCTGGCCGT CTTGGAGGTC TTGTTTCTCT GGGTTTATGC    19380
CTCGAGGTGG CGCCTGCTCC CCTGTGCTCC CTGGTAGCCT GGTAGTGAGC CTGCTTCTCA    19440
CACAGTCATA CCTGGTTGTG GTCCCACAGT GGGACCACCC TGTTGGGTTC AGAACAGGAG    19500
ATGGGGCCC CTCGAGTCTG TGTGGGGCT GTGGACAGGG TTGGGAGACC TTGGCTCTGT      19560
GGGGACTGT GGACAGGGGA TGGGGGGCCT TGGCCCTGCG TGGGATGGGT TGGGGGTCCG     19620
TGCCCTTCCT GGCCCTGGGT GGACAGGTCC ATGTGGCACT CGGCATAGGG CTGAGATGGG    19680
TGCAGAGGGC TGAGGCCCCC AGGCCTCTCC TGGCTTGGTT TCCCCAGATG AGTGTTCATT    19740
TGGGTCTTCC ATCAGAAAGT CCCCTCCTGA CCTCTGGGAG TGGGGAGCTC AAGGGTGGGA    19800
GGCCATAGCT TGGGGATGCT GGCAATGTGT GGGATGGGCC CAGGGAAGGC CTCTGGCCTA    19860
CTAGGGGCTC TGGCCCTGAC CCACGGCCAC TCACTCCTCA GAGACGTCTC CCACAACCTG    19920
CTCCGGGCGC TGGACGTTGG GCTCCTGGCG AACCTCTCGG CGCTGGCAGA GCTGTGAGTG    19980
TCCCCCAGTC GTGCCAGCAT GCGGGCTCA CTCCGGGTGG GCTGGCGGCA CCGCCTCTTG     20040
CTGCTCAGCT GTGGGGGCTT CCATCAGCTT TGCCGAATCC CCGTCTCTT CCAGGGATAT     20100
AAGCAACAAC AAGATTTCTA CGTTAGAAGA AGGAATATTT GCTAATTTAT TTAATTTAAG    20160
TGAAATGTAA GTTGTGGTTC TTTGGGTGGG GTCCTGGCTG ACCCCAGGC CCCCAATATC     20220
CCTTCTGCCC TCCCAGTTGG TCCGTGTCCC CTTCCAGGCT TGAGACCAGA TCCTGGGGGC    20280
AGTTCACTGC CTGCTTGGAG CCCCCCAGTG CCGGCTTGGT TGGGCAGGG GAGGCGGTGC     20340
TGTCAGGGTG GCTCCAGGGC CTGGTTGCCA GTGGGGGCT GGCATAGACC CTTCCCACCA     20400
GACCTGGTCC CCAACACCTG CCCCTGCCCT GCAGAAACCT GAGTGGGAAC CCGTTTGAGT    20460
GTGACTGTGG CCTGGCGTGG CTGCCGCGAT GGGCGGAGGA GCAGCAGGTG CGGGTGGTGC    20520
AGCCCGAGGC AGCCACGTGT GCTGGGCCTG GCTCCCTGGC TGGCCAGCCT CTGCTTGGCA    20580
TCCCCTTGCT GGACAGTGGC TGTGGTGAGT GCCGGTGGGT GGGGCCAGCT CTGTCCTTCC    20640
CAGCCAGGTG GGACCTGGGC CCTGCAGACA CTGGGCAGGG CTCAGGAAGG CCTCTCTGGG    20700
GGGGGCCTCC GGGCCAAGGG AACAGCATGG GAGCCTGTGA GTGCGGCGGG CGGATGTGGG    20760
GGCGTGGGGT GGAGCCAGGA GGAGCAGAAC CCGGGGTCCA GTGGCTGCCT CTTCTAGGTG    20820
```

| | | | | | |
|---|---|---|---|---|---|
|AGGAGTATGT|CGCCTGCCTC|CCTGACAACA|GCTCAGGCAC|CGTGGCAGCA|GTGTCCTTTT 20880|
|CAGCTGCCCA|CGAAGGCCTG|CTTCAGCCAG|AGGCCTGCAG|CGCCTTCTGC|TTCTCCACCG 20940|
|GCCAGGGCCT|CGCAGCCCTC|TCGGAGCAGG|GCTGGTGCCT|GTGTGGGGCG|GCCCAGCCCT 21000|
|CCAGTGCCTC|CTTTGCCTGC|CTGTCCCTCT|GCTCCGGCCC|CCGCCACCT|CCTGCCCCA 21060|
|CCTGTAGGGG|CCCCACCCTC|CTCCAGCACG|TCTTCCCTGC|CTCCCAGGG|GCCACCCTGG 21120|
|TGGGGCCCCA|CCGACCTCTG|GCCTCTGGCC|AGCTAGCAGC|CTTCCACATC|GCTGCCCCGC 21180|
|TCCCTGTCAC|TGCCACACGC|TGGGACTTCG|GAGACGGCTC|CGCCGAGGTG|GATGCCGCTG 21240|
|GGCCGGCTGC|CTCGCATCGC|TATGTGCTGC|CTGGGCGCTA|TCACGTGACG|GCCGTGCTGG 21300|
|CCCTGGGGGC|CGGCTCAGCC|CTGCTGGGA|CAGACGTGCA|GGTGGAAGCG|GCACCTGCCG 21360|
|CCCTGGAGCT|CGTGTGCCCG|TCCTCGGTGC|AGAGTGACGA|GAGCCTCGAC|CTCAGCATCC 21420|
|AGAACCGCGG|TGGTTCAGGC|CTGGAGGCCG|CCTACAGCAT|CGTGGCCCTG|GGCGAGGAGC 21480|
|CGGCCCGAGG|TGAGTGTCTG|CTGCCCACTC|CCCTTCCTCC|CCAGGGCCAT|CCAGATGGGG 21540|
|CAGAGCCTGG|TACCCCGTC|TTGGGCCCAC|ACTGACCGTT|GACACCCTCG|TTCCCACCGG 21600|
|TCTCCAGCGG|TGCACCCGCT|CTGCCCCTCG|GACACGGAGA|TCTTCCCTGG|CAACGGGCAC 21660|
|TGCTACCGCC|TGGTGGTGGA|GAAGGCGGCC|TGGCTGCAGG|CGCAGGAGCA|GTGTCAGGCC 21720|
|TGGGCCGGGG|CCGCCCTGGC|AATGGTGGAC|AGTCCCGCCG|TGCAGCGCTT|CCTGGTCTCC 21780|
|CGGGTCACCA|GGTGCCTGCC|CCCACCCCCC|GAGGGGCCAT|AGGTTGGGAG|ATCTCTGAAG 21840|
|CACTGGGGCA|GAGACTGCGG|CTGGGGAGTC|TCAGGAGGAA|GGAGGTGGGA|GCTGGGCCGG 21900|
|CCCTGGTGAG|CAGGTGGCGC|CGGCCGGTGG|GGCCGTTCCT|GTCAGCTCTG|CAGATGCAGA 21960|
|GGTGGACATG|AGCTGGGGGC|AGCCTCCGGA|CACTCCTGGG|CACGCCATAC|GGGAGGTGGC 22020|
|CTGCACGGGG|ATCCCTGCCG|GTACCCACAG|GCCCCGTGGG|TGGGTGCTGC|TGTGAGCCTG 22080|
|GGCTGGTGGG|CCCTGGTCTC|CGGGCTCTGA|GCCTCAGTTT|CCCCATCTGG|AAAGGGGAC 22140|
|AGTGATGCCG|CTCCCAGCGG|GCTGCTGTGA|GGGTGGGAGG|ATGGAGGAGT|GCCCTGAGCC 22200|
|CCCTGCCATC|CCACACCCGC|CCCCAGGAGC|CTAGACGTGT|GGATCGGCTT|CTCGACTGTG 22260|
|CAGGGGGTGG|AGGTGGGCCC|AGCGCCGCAG|GGCGAGGCCT|TCAGCCTGGA|GAGCTGCCAG 22320|
|AACTGGCTGC|CCGGGGAGCC|ACACCCAGCC|ACAGCCGAGC|ACTGCGTCCG|GCTCGGGCCC 22380|
|ACCGGGTGGT|GTAACACCGA|CCTGTGCTCA|GCGCCGCACA|GCTACGTCTG|CGAGCTGCAG 22440|
|CCCGGAGGTG|TGCGGGGGGC|CAGGCAGGGG|CCTGAGACGC|TGGCTGTGGT|TAGGGGCCTG 22500|
|CCGAGCGCCC|GCGGTGGAGC|CTGGGCTGAG|GAGGAGGGGC|TGGTGGGGGG|GTTTTCGGGC 22560|

```
GGCTCGGTCC CCAGTCTGTT CGTCCTGGTG TCCTGGGCCC TGGCCCGGCG CCTCACTGTG    22620
CACTCGCCAC CCCAGGCCCA GTGCAGGATG CCGAGAACCT CCTCGTGGGA GCGCCCAGTG    22680
GGGACCTGCA GGGACCCCTG ACGCCTCTGG CACAGCAGGA CGGCCTCTCA GCCCCGCACG    22740
AGCCCGTGGA GGTAGTCGGC CCCCACGTT CTACAACCTG CCCTCCTGCC TGCCCCTGGA     22800
GGCCTTGCCT GCCCTGCCCA CTGTGGGTCT CGCCAAAAAA CTTGGGGGCC TTAATGTTGC    22860
TTGTGCCCAG TGAAGATGGT TGGGAAAATC CAGAGTGCAG AGAGGAAAGC GTTTACTCAC    22920
ATTACCTCCA GGCCTTTTCT CTGAGCGTGT GTGAGTTATT CCTGAAAGGC AGGTCAGGGG    22980
TCCTGCCCCC CATGGACAGT TTCCACCGGA GTCTTCCTCT CGAGCGACAG GAGCCAGGCC    23040
TGTGGGGGTC TGATGGCTCG CTCTCCTTCC CTCCCCTCTT CCTGGGAAGT TCGGGTAGGG    23100
GGAGTCTGGG CTTCAGGCTG GGATGGGGTC TGTGGAGCTG AGGCGGCCCC CTGCCCACCA    23160
GGTCATGGTA TTCCCGGGCC TGCGTCTGAG CCGTGAAGCC TTCCTCACCA CGGCCGAATT    23220
TGGGACCCAG GAGCTCCGGC GGCCCGCCCA GCTGCGGCTG CAGGTGTACC GGCTCCTCAG    23280
CACAGCAGGT GGGACTCTGG GTGGTGGGTG GTGGGTGGTG GGCGCCGCAG GACTCGGGGT    23340
GGCCTCTCTG AGCTTTCACG TCTGCTGGTC CTGTGGCCAC CAGAGTGGTT CCCAGTCTTA    23400
GGTGGACAGA GCAGGGGTTC CAGAGACACC AGCTCATTCC AGGTGTCCTG GGGGTGGATT    23460
GGGTGGGGCC TGCCTGGGGG CCGGCCTGGG TCAGTCGGCT GGCCGGAGAC GGACGCAGCA    23520
CTGGGCTGGG AGTGCTGCCC AGGTGGGGAG ACCTGTCCTC ACAGCAAGGC CAGGATTGCT    23580
GGTGCAGGCA GTTGGGCATC TCTGACGGTG GCCTGTGGGC AAATCAGGGC CCAACACCC    23640
TCCCCTCCTC ACAGGGACCC CGGAGAACGG CAGCGAGCCT GAGAGCAGGT CCCCGGACAA    23700
CAGGACCCAG CTGGCCCCCG CGTGCATGCC AGGGGACGC TGGTGCCCTG GAGCCAACAT     23760
CTGCTTGCCG CTGGACGCCT CCTGCCACCC CCAGGCCTGC GCCAATGGCT GCACGTCAGG    23820
GCCAGGGCTA CCCGGGGCCC CCTATGCGCT ATGGAGAGAG TTCCTCTTCT CCGTTCCCGC    23880
GGGGCCCCCC GCGCAGTACT CGGTGTGTGG CCCTGACCTG GGTCTGTTCC CTGCATCTCC    23940
TCAGGCCACC TTCCTGTCTC CTGCCCAGGG TCTGGGTCTG TGCACCAGAC ACACCCAGCC    24000
TGCAGGCCCC TCCCACGTCC TTGCCACCTC TGACCTCCGA CCTCTGCAGT GCCCTCGGCC    24060
CTCTCCCAGT GGGAGAAGCT CTCGCCTGGG CCCTTGGCAC GAGCTGTGCC TCCTCTTCCT    24120
CTCTCCCAGC ACAGCTGCTC CTTCCTGTCT GCCAGGTCTT GGCCTGTGTC CTCTCCCCGT    24180
GTGTCCCCCG GTCTGCAACT GTCCTGCCTG TCCTTGTCAC GAGCACTGTG GGGAGGCTCC    24240
TTGAGGTGTG GCTGACGAAG CGGGGAGCCC TGCGTGTCCA CCCTCATCCG TCGTGCGGGG    24300
```

```
GTCCACGGGC CATGACCGTG AGGACGTGAT GCAGCCCTGC CTCCCTCTCC ACAGGTCACC    24360

CTCCACGGCC AGGATGTCCT CATGCTCCCT GGTGACCTCG TTGGCTTGCA GCACGACGCT    24420

GGCCCTGGCG CCCTCCTGCA CTGCTCGCCG GCTCCCGGCC ACCCTGGTCC CCGGGCCCCG    24480

TACCTCTCCG CCAACGCCTC GTCATGGCTG CCCCACTTGC CAGCCCAGCT GGAGGGCACT    24540

TGGGCCTGCC CTGCCTGTGC CCTGCGGCTG CTTGCAGCCA CGGAACAGCT CACCGTGCTG    24600

CTGGGCTTGA GGCCCAACCC TGGACTGCGG CTGCCTGGGC GCTATGAGGT CCGGGCAGAG    24660

GTGGGCAATG GCGTGTCCAG GCACAACCTC TCCTGCAGCT TTGACGTGGT CTCCCCAGTG    24720

GCTGGGCTGC GGGTCATCTA CCCTGCCCCC CGCGACGGCC GCCTCTACGT GCCCACCAAC    24780

GGCTCAGCCT TGGTGCTCCA GGTGGACTCT GGTGCCAACG CCACGGCCAC GGCTCGCTGG    24840

CCTGGGGGCA GTGTCAGCGC CCGCTTTGAG AATGTCTGCC CTGCCCTGGT GGCCACCTTC    24900

GTGCCCGGCT GCCCCTGGGA GACCAACGAT ACCCTGTTCT CAGTGGTAGC ACTGCCGTGG    24960

CTCAGTGAGG GGGAGCACGT GGTGGACGTG GTGGTGGAAA ACAGCGCCAG CCGGGCCAAC    25020

CTCAGCCTGC GGGTGACGGC GGAGGAGCCC ATCTGTGGCC TCCGCGCCAC GCCCAGCCCC    25080

GAGGCCCGTG TACTGCAGGG AGTCCTAGTG GTGAGTATGG CCGAGGCTCC ACCACCAGCC    25140

CCCAGGCAGG TGCCTGCAGA CAGGGTGCTC ACACAGGGCG TGAGGCCTGG CTTCCCAGTG    25200

AGGGCAGCAG CCCAGTTACT GGGGACGTCG GCCCCGGGCA GGTCCTGCTG GCTGGCTCCT    25260

CGGGCTACCT GGTGGGCTTT AAATTCCTGG AAAGTCACGG CTCTGACAGT GGCTCCGCTA    25320

ACTCATTCCA CTGTCTCATT TCACAAAATG AATTTAAAAC TCTGCTCCCT GACCTCACAC    25380

GAGCCCCCGT GAGTCTCTCA CGCCCTCTGC TGTGTTCTCG CCTGGCTAAA GCGAGTGGCT    25440

TTTGAGGTGG AGTCTGAACC CCTGATGGGA AACTGCGGGC TGCCCGCGGT GCCACCATGC    25500

TGGGTACATG GGGGACAGGG CTGTCTCCAT CTTGCGGGTA CCTGCCTCTT CACCAGGGGC    25560

CTTGGGAGGG GCCATCAGAA ATGGCGTGAC CTGTGCAGCC TGTCCTGGGT TCTGTAAGCC    25620

AGTGTAGGTG CCTCCCCTCA CTGCTCCAG CTCTCTGGGT GAGGAGCTGG GGCAACAGCG    25680

CCGGGAGGGT CTGAGAAGAC TCAGAGAGAG GTGGACTCTT TGTAGCTGGT ACTAGGTTTG    25740

CTTTACAGAT GGGCAAACTG AGGCACAGAG AGGTTGAGGC ATTAGTAGTA CTACATGGCT    25800

GGCTGGAGAG CCGGACAGTG AGTGTCCCAG CCCGGGCTTG GCTCCCATGG CATGCAGAGC    25860

CCCGGGCACC TCCTCTCCTC TGTGCCCCGC GTGGGACTCT CCAGCCCGAC GGGAGGTGTG    25920

TCCAGGAGGC GACAGGCTAA GGGCAGAGTC CTCCACAGAG CCCAGGCTGA CACCATTCCC    25980

CCCGCAGAGG TACAGCCCCG TGGTGGAGGC CGGCTCGGAC ATGGTCTTCC GGTGGACCAT    26040
```

```
CAACGACAAG CAGTCCCTGA CCTTCCAGAA CGTGGTCTTC AATGTCATTT ATCAGAGCGC    26100
GGCGGTCTTC AAGCTCTCAG TAGGTGGGCG GGGGTGGGGA GGGGAGGGGA TGGGGCGGGG    26160
CAGGGCGGGG GCGGGCTCCA CCTTCACCTC TGCCTTCTGC TCTGCTTCAT GCTGCCCGAG    26220
GACGCTGCCA TGGCTGTGGG TGAGTGGAGG GAGGGACGCC AATCAGGGCC AGGCCTCTCA    26280
CCTGCCACCT GGGCTCACTG ACGCCTGTCC CTGCAGCTGA CGGCCTCCAA CCACGTGAGC    26340
AACGTCACCG TGAACTACAA CGTAACCGTG GAGCGGATGA ACAGGATGCA GGGTCTGCAG    26400
GTCTCCACAG TGCCGGCCGT GCTGTCCCCC AATGCCACGC TAGCACTGAC GGCGGGCGTG    26460
CTGGTGGACT CGGCCGTGGA GGTGGCCTTC CTGTGAGTGA CTCGGGGCC GGTTTGGGGT    26520
GGGCACCAGG CTCTTGTCCC AGCCCAGCC TCAGCCGAGG GACCCCACA TCACGGGGTT     26580
GCTTTTCTGA GCCTCGGTTT CCCTGTCTGT TGGGAGGTAA CTGGGTGCAC AGGAGCCCTG    26640
AGGCTGCACG GGAGCCGGGA GAGGCCTCAG CACAGCCGGG TGGGCCCTGA ATGGAGGCCC    26700
GGGGCGTGAC TGCAGAGTGG AGCCTCGGCT GGGTCCCAAG CACCCCTGC CCCGCCACCG     26760
CCCACCCCTG TCCCGGTTCA CTCACTGCGT CCCACCGCCC CGGCAGGTGG ACCTTTGGGG    26820
ATGGGGAGCA GGCCCTCCAC CAGTTCCAGC CTCCGTACAA CGAGTCCTTC CCGGTTCCAG    26880
ACCCCTCGGT GGCCCAGGTG CTGGTGGAGC ACAATGTCAT GCACACCTAC GCTGCCCCAG    26940
GTGAGGGATG AGGGGGTGAG GGGGCCACTG CCTTTCAGGC TCTGAGCACG GGTCCCCCA     27000
GCTCCCCAGT CAAGCTGCCC CCCTTCCTCC CCAACAGCCC TCACTGTGAC CTCACCTGGG    27060
CTGATGGCTT AGGCCCTACT GGGGTGAGGG AGGGGCCAGG CGTGGGGGA GTGGACAGGG     27120
AAGCTGGGCC CCTGAACTGC GCCCCCCGCC CTCCCCGGGC CTGGCTCTTG CTGCTCTGCT    27180
GCCCCGAGTG CAGCTGCACT TGGAGGCGGT GCGTCCTCGC CAGGCAGCCC TCAGTGCTGC    27240
TACACCTGTG CTCCGTCCCG CACGTGGCTT GGGAGCCTGG GACCCTTAAG GCTGGGCCGC    27300
AGGTGCAGCC GTTCACCCCG GCTCCTCAG GCGGGGGGCT TCTGCCGAGC GGGTGGGGAG     27360
CAGGTGGGGG TGCCGCGGCT GCCCCACTCG GGCCTGTCCC CACAGGTGAG TACCTCCTGA    27420
CCGTGCTGGC ATCTAATGCC TTCGACAACC GGACGCAGCA GGTGCCTGTG AGCGTGCGCG    27480
CCTCCCTGCC CTCCGTGGCT GTGGGTGTGA GTGACGGCGT CCTGGTGGCC GGCCGGCCCG    27540
TCACCTTCTA CCCGCACCCG CTGCCCTCGC CTGGGGTGT TCTTTACACG TGGGACTTCG     27600
GGACGGCTC CCCTGTCCTG ACCCAGAGCC AGCCGGCTGC CAACCACACC TATGCCTCGA     27660
GGGGCACCTA CCACGTGCGC CTGGAGGTCA ACAACACGGT GAGCGGTGCG GCGGCCCAGG    27720
CGGATGTGCG CGTCTTTGAG GAGCTCCGCG GACTCAGCGT GGACATGAGC CTGGCCGTGG    27780
```

```
AGCAGGGCGC CCCCGTGGTG GTCAGCGCCG CGGTGCAGAC GGGCGACAAC ATCACGTGGA    27840

CCTTCGACAT GGGGGACGGC ACCGTGCTGT CGGGCCCGGA GGCAACAGTG GAGCATGTGT    27900

ACCTGCGGGC ACAGAACTGC ACAGTGACCG TGGGTGCGGC CAGCCCCGCC GGCCACCTGG    27960

CCCGGAGCCT GCACGTGCTG GTCTTCGTCC TGGAGGTGCT GCGCGTTGAA CCCGCCGCCT    28020

GCATCCCCAC GCAGCCTGAC GCGCGGCTCA CGGCCTACGT CACCGGGAAC CCGGCCCACT    28080

ACCTCTTCGA CTGGACCTTC GGGGATGGCT CCTCCAACAC GACCGTGCGG GGGTGCCCGA    28140

CGGTGACACA CAACTTCACG CGGAGCGGCA CGTTCCCCCT GGCGCTGGTG CTGTCCAGCC    28200

GCGTGAACAG GGCGCATTAC TTCACCAGCA TCTGCGTGGA GCCAGAGGTG GGCAACGTCA    28260

CCCTGCAGCC AGAGAGGCAG TTTGTGCAGC TCGGGGACGA GGCCTGGCTG GTGGCATGTG    28320

CCTGGCCCCC GTTCCCCTAC CGCTACACCT GGACTTTGG CACCGAGGAA GCCGCCCCCA    28380

CCCGTGCCAG GGGCCCTGAG GTGACGTTCA TCTACCGAGA CCCAGGCTCC TATCTTGTGA    28440

CAGTCACCGC GTCCAACAAC ATCTCTGCTG CCAATGACTC AGCCCTGGTG GAGGTGCAGG    28500

AGCCCGTGCT GGTCACCAGC ATCAAGGTCA ATGGCTCCCT TGGGCTGGAG CTGCAGCAGC    28560

CGTACCTGTT CTCTGCTGTG GGCCGTGGGC GCCCCGCCAG CTACCTGTGG GATCTGGGGG    28620

ACGGTGGGTG GCTCGAGGGT CCGGAGGTCA CCCACGCTTA CAACAGCACA GGTGACTTCA    28680

CCGTTAGGTG GCCGGCTGGA ATGAGGTGAG CCGCAGCGAG GCCTGGCTCA ATGTGACGGT    28740

GAAGCGGCGC GTGCGGGGGC TCGTCGTCAA TGCAAGCCCC ACGGTGGTGC CCCTGAATGG    28800

CAGCGTGAGC TTCAGCACGT CGCTGGAGGC CGGCAGTGAT GTGCGCTATT CCTGGGTGCT    28860

CTGTGACCGC TGCACGCCCA TCCCTGGGGG TCCTACCATC TCTTACACCT TCCGCTCCGT    28920

GGGCACCTTC AATATCATCG TCACGGCTGA GAACGAGGTG GGCTCCGCCC AGGACAGCAT    28980

CTTCGTCTAT GTCCTGCAGC TCATAGAGGG GCTGCAGGTG GTGGGCGGTG CCGCTACTT    29040

CCCCACCAAC CACACGGTAC AGCTGCAGGC CGTGGTTAGG GATGGCACCA ACGTCTCCTA    29100

CAGCTGGACT GCCTGGAGGG ACAGGGGCCC GGCCCTGGCC GGCAGCGGCA AAGGCTTCTC    29160

GCTCACCGTC TCGAGGCCGG CACCTACCAT GTGCAGCTGC GGGCCACCAA CATGCTGGGC    29220

AGCGCCTGGG CCGACTGCAC CATGGACTTC GTGGAGCCTG TGGGGTGGCT GATGGTGGCC    29280

GCCTCCCCGA ACCCAGCTGC CGTCAACAAA AGCGTCACCC TCAGTGCCGA GCTGGCTGGT    29340

GGCAGTGGTG TCGTATACAC TTGGTCCTTG GAGGAGGGGC TGAGCTGGGA GACCTCCGAG    29400

CCATTTACCA CCCATAGCTT CCCCACACCC GGCCTGCACT TGGTCACCAT GACGGCAGGG    29460

AACCCGCTGG GCTCAGCCAA CGCCACCGTG GAAGTGGATG TGCAGGTGCC TGTGAGTGGC    29520
```

```
CTCAGCATCA GGGCCAGCGA GCCCGGAGGC AGCTTCGTGG CGGCCGGGTC CTCTGTGCCC    29580

TTTTGGGGGC AGCTGGCCAC GGGCACCAAT GTGAGCTGGT GCTGGGCTGT GCCCGGCGGC    29640

AGCAGCAAGC GTGGCCCTCA TGTCACCATG GTCTTCCCGG ATGCTGGCAC CTTCTCCATC    29700

CGGCTCAATG CCTCCAACGC AGTCAGCTGG GTCTCAGCCA CGTACAACCT CACGGCGGAG    29760

GAGCCCATCG TGGGCCTGGT GCTGTGGGCC AGCAGCAAGG TGGTGGCGCC CGGGCAGCTG    29820

GTCCATTTTC AGATCCTGCT GGCTGCCGGC TCAGCTGTCA CCTTCCGCCT GCAGGTCGGC    29880

GGGGCCAACC CCGAGGTGCT CCCCGGGCCC CGTTTCTCCC ACAGCTTCCC CCGCGTCGGA    29940

GACCACGTGG TGAGCGTGCG GGGCAAAAAC CACGTGAGCT GGGCCCAGGC GCAGGTGCGC    30000

ATCGTGGTGC TGGAGGCCGT GAGTGGGCTG CAGGTGCCCA ACTGCTGCGA GCCTGGCATC    30060

GCCACGGGCA CTGAGAGGAA CTTCACAGCC CGCGTGCAGC GCGGCTCTCG GGTCGCCTAC    30120

GCCTGGTACT TCTCGCTGCA GAAGGTCCAG GGCGACTCGC TGGTCATCCT GTCGGGCCGC    30180

GACGTCACCT ACACGCCCGT GGCCGCGGGG CTGTTGGAGA TCCAGGTGCG CGCCTTCAAC    30240

GCCCTGGGCA GTGAGAACCG CACGCTGGTG CTGGAGGTTC AGGACGCCGT CCAGTATGTG    30300

GCCCTGCAGA GCGGCCCCTG CTTCACCAAC CGCTCGGCGC AGTTTGAGGC CGCCACCAGC    30360

CCCAGCCCCC GGCGTGTGGC CTACCACTGG GACTTTGGGG ATGGGTCGCC AGGGCAGGAC    30420

ACAGATGAGC CCAGGGCCGA GCACTCCTAC CTGAGGCCTG GGACTACCG CGTGCAGGTG    30480

AACGCCTCCA ACCTGGTGAG CTTCTTCGTG GCGCAGGCCA CGGTGACCGT CCAGGTGCTG    30540

GCCTGCCGGG AGCCGGAGGT GGACGTGGTC CTGCCCCTGC AGGTGCTGAT GCGGCGATCA    30600

CAGCGCAACT ACTTGGAGGC CCACGTTGAC CTGCGCGACT GCGTCACCTA CCAGACTGAG    30660

TACCGCTGGG AGGTGTATCG CACCGCCAGC TGCCAGCGGC CGGGGCGCCC AGCGCGTGTG    30720

GCCCTGCCCG GCGTGGACGT GAGCCGGCCT CGGCTGGTGC TGCCGCGGCT GGCGCTGCCT    30780

GTGGGGCACT ACTGCTTTGT GTTTGTCGTG TCATTTGGGG ACACGCCACT GACACAGAGC    30840

ATCCAGGCCA ATGTGACGGT GGCCCCCGAG CGCCTGGTGC CCATCATTGA GGGTGGCTCA    30900

TACCGCGTGT GGTCAGACAC ACGGGACCTG GTGCTGGATG GGAGCGAGTC CTACGACCCC    30960

AACCTGGAGG ACGGCGACCA GACGCCGCTC AGTTTCCACT GGGCCTGTGT GGCTTCGACA    31020

CAGGTCAGTG CGTGGCAGGG CCGTCCTCCA TGCCCCTCAC CCGTCCACAC CCATGAGCCC    31080

AGAGAACACC CAGCTTGCCA CCAGGGCTGG CCCGTCCTCA GTGCCTGGTG GCCCCGTCC    31140

CAGCATGGGG AGGGGGTCTC CCGCGCTGTC TCCTGGGCCG GGCTCTGCTT TAAAACTGGA    31200

TGGGGCTCTC AGGCCACGTC GCCCCTTGTT CTCGGCCTGC AGAGGGAGGC TGGCGGGTGT    31260
```

| | | | | | |
|---|---|---|---|---|---|
| GCGCTGAACT | TTGGGCCCCG | CGGGAGCAGC | ACGGTCACCA | TTCCACGGGA | GCGGCTGGCG | 31320
| GCTGGCGTGG | AGTACACCTT | CAGCCTGACC | GTGTGGAAGG | CCGGCCGCAA | GGAGGAGGCC | 31380
| ACCAACCAGA | CGGTGGGTGC | CGCCCGCCCC | TCGGCCACTT | GCCTTGGACA | GCCCAGCCTC | 31440
| CCTGGTCATC | TACTGTTTTC | CGTGTTTTAG | TGCTGGTGGA | GGCCGCACGC | TCTCCCCTCT | 31500
| CTGTTTCTGA | TGCAAATTCT | ATGTAACACG | ACAGCCTGCT | TCAGCTTTGC | TTCCTTCCAA | 31560
| ACCTGCCACA | GTTCCACGTA | CAGTCTTCAA | GCCACATATG | CTCTAGTGGC | AAAAGCTACA | 31620
| CAGTCCCCTA | GCAATACCAA | CAGTGAGGAA | GAGCCCCTTC | CCACCCCAGA | GGTAGCCACT | 31680
| GTCCCCAGCC | CATGTCCCTG | TTGCTGGATG | TGGTGGGCCG | GTTCTCACCC | TCACGCTCCC | 31740
| CTCTCTGGAC | CGGCCAGGAG | GCTTGGTGAC | CCTGAGCCCG | TGGTGGCTGC | TCCTGCTGCT | 31800
| GTCAGGCGGG | GCCTGCTGGT | GCCCCAGAGT | GGGCGTCTGT | TCCCCAGTCC | CTGCTTTCCT | 31860
| CAGCTGGCCT | GATTGGGGGT | CTTCCCAGAG | GGGTCGTCTG | AGGGGAGGGT | GTGGGAGCAG | 31920
| GTTCCATCCC | AGCTCAGCCT | CCTGACCCAG | GCCCTGGCTA | AGGGCTGCAG | GAGTCTGTGA | 31980
| GTCAGGCCTA | CGTGGCAGCT | GCGGTCCTCA | CACCCACACA | TACGTCTCTT | CTCACACGCA | 32040
| TCCCCCCAGG | GGCCCTCAGT | GAGCATTGCC | TGCCTCCTGC | TAGGGTCCAG | CTGGGTCCAG | 32100
| TACACCAGAA | CGCACACTCC | AGTGTCCTCT | GCCCTGTGTA | TGCCCTTCCG | CCGTCCAAGT | 32160
| TGGAAGGTGG | CAAACCGGAT | GAGTATCCTG | GGAGGGAGTG | AGCTCACCGG | CAGTGGCCAG | 32220
| GCCCCTGGGA | AACCTGGAGT | TTGGGAGCAG | CATCCTCCAT | GGGTCCCCCA | GTCCTTCCAG | 32280
| CAGGCCAAAT | AGACCTGTGT | TGGAGGTAAC | CCCACTCCCA | CGCCAGGTGC | TGATCCGGAG | 32340
| TGGCCGGGTG | CCCATTGTGT | CCTTGGAGTG | TGTGTCCTGC | AAGGCACAGG | CCGTGTACGA | 32400
| AGTGAGCCGC | AGCTCCTACG | TGTACTTGGA | GGGCCGCTGC | CTCAATTGCA | GCAGCGGCTC | 32460
| CAAGCGAGGG | GTGAGTGTTG | AGCGGGGTGT | GGGCGGGCTG | GGGATGGGTC | CCATGGCCGA | 32520
| GGGGACGGGG | CCTGCAGGCA | GAAGTGGGGC | TGACAGGGCA | GAGGGTTGCG | CCCCCTCACC | 32580
| ACCCCTTCTG | CCTGCAGCGG | TGGGCTGCAC | GTACGTTCAG | CAACAAGACG | CTGGTGCTGG | 32640
| ATGAGACCAC | CACATCCACG | GGCAGTGCAG | GCATGCGACT | GGTGCTGCGG | CGGGGCGTGC | 32700
| TGCGGGACGG | CGAGGGATAC | ACCTTCACGC | TCACGGTGCT | GGGCCGCTCT | GGCGAGGAGG | 32760
| AGGGCTGCGC | CTCCATCCGC | CTGTCCCCCA | ACCGCCCGCC | GCTGGGGGGC | TCTTGCCGCC | 32820
| TCTTCCCACT | GGGCGCTGTG | CACGCCCTCA | CCACCAAGGT | GCACTTCGAA | TGCACGGGTG | 32880
| AGTGCAGGCC | TGCGTGGGGG | GAGCAGCGGG | ATCCCCGAC | TCTGTGACGT | CACGGAGCCC | 32940
| TCCCGTGATG | CCGTGGGGAC | CGTCCCTCAG | GCTGGCATGA | CGCGGAGGAT | GCTGGCGCCC | 33000

```
CGCTGGTGTA CGCCCTGCTG CTGCGGCGCT GTCGCCAGGG CCACTGCGAG GAGTTCTGTG    33060
TCTACAAGGG CAGCCTCTCC AGCTACGGAG CCGTGCTGCC CCCGGGTTTC AGGCCACACT    33120
TCGAGGTGGG CCTGGCCGTG GTGGTGCAGG ACCAGCTGGG AGCCGCTGTG GTCGCCCTCA    33180
ACAGGTGAGC CAGGCCGTGG GAGGGCGCCC CCGAGACTGC CACCTGCTCA CCACCCCCTC    33240
TGCTCGTAGG TCTTTGGCCA TCACCCTCCC AGAGCCCAAC GGCAGCGCAA CGGGGCTCAC    33300
AGTCTGGCTG CACGGGCTCA CCGCTAGTGT GCTCCCAGGG CTGCTGCGGC AGGCCGATCC    33360
CCAGCACGTC ATCGAGTACT CGTTGGCCCT GGTCACCGTG CTGAACGAGG TGAGTGCAGC    33420
CTGGGAGGGG ACGTCACATC TGCTGCATGC GTGCTTGGGA CCAAGACCTG TACCCCTGCC    33480
TGGAGCTTTG CAGAGGGCTC ATCCCGGGCC CAGAGATAA ATCCCAGTGA CCCTGAAGCA    33540
GCACCCCGAC CTTCCGCTCC CAGCAGCCAC ACCCACCGGG CCCTCTCCGG CGTCTGCTTT    33600
CCACAATGCA GCCCCGCCC AGGAGGGCCC ATGTGCTTAC CCTGTTTTGC CCATGAAGAA    33660
ACAGCTCAGT GTTGTGGGTC AGTGCCCGCA TCACACAGCG TCTAGCACGT AACTGCACCC    33720
CGGGAGTCGT GGGCATCTGC TGGCCTCCTG CCGGCCTCCT GCGCTGCTGA CAGCTTGCTG    33780
TGCCCCCTGC CTGCCCCAGT ACGAGCGGGC CCTGGACGTG GCGCAGAGCC CAAGCACGAG    33840
CGGCAGCACC GAGCCCAGAT ACGCAAGAAC ATCACGGAGA CTCTGGTGTC CCTGAGGGTC    33900
CACACTGTGG ATGACATCCA GCAGATCGCT GCTGCGCTGG CCCAGTGCAT GGTAGGATGG    33960
CCCCACCTGC TCACCCTGCC CCGCATGCCT GCCAGGGCAC TGGGTTCAGC CCCCCAGGGC    34020
AGACGGGCAG CTTGGCCGAG GAGCTGAGCC TCCAGCCTGG GCTCCTTCCT GCCATGGCGT    34080
TCCTCGGTCT CTGACCTGCT TCAGTAGCCT CAGCCGTTCT GTCCTGTGTG AACGCAGGGT    34140
GCCTCTCGGG GGACCCAGGG TGTAAAGAGG GGCCCAGATG TGGGGAGGGA CTAAGAAGAT    34200
GCTGCTCTGT GCCCTCCACT CTCCCCTCCC CTCCCCTCCC CCTTCCCTCC CCTAGCCCCT    34260
CCCCTCCTCC CCTCCCCTAG CCCTTCCCCT CCTCCCCTCC CCTAGCCCTT TCCCTTCTTC    34320
CCCCCAGCC CTTCCCCTCC TCCCCTCCCC TAGCCCTTCC CCTCCTCCCC TCCCCTACCC    34380
CTTCCCCTCC TCCCCTCCCC TAGACCTTCC CCTCACCTCC TCCCGCTGAG CCCCTCCACT    34440
CGTCCCCCAG CCCCTCCCTC CCCTAGCCCC TCCCCTCCCC CTTCCTCCCC TCCTCCCCCT    34500
CCCCTCCTCC CCTCCCTCT TCCTCCCCCT CCCCTCCTCC CCCTTCCTCC CCTCTCCTCC    34560
CCCTCCCCTC CTGTCCCCCC TCCTCCCCTC CTCCCTCCTC CCCTCCTCCC CCTCCTCCT    34620
CCCCCTCCTC CCTCCTCCCT CCTCCCCCTC CTCCTCCTCC CCTCCTCCCT CCTCCCCTCC    34680
TCCCCTCCCC TCCTCCCCCT CCCCCCTCCC TTCCTCCCCC TCCCCCCTCC CCTCCTCCCC    34740
```

```
CTCTCCTCCT CCCATCCCTC CTCCCATCCC TCCTCCCCGT TCCCATTCTC TCCCCTCCCC    34800

CTTCCATTTC TCCCTCCTCC CCCTGCCCTC CTCTCCTCCT CACCTCCCCT TCTCCGCTCC    34860

TTTCTTCTCC TCCCTCCCTT TCTCTCCTCC CTCCCCTTCT CCCCTTCTCC TCTTCTCCCC    34920

TTCTCCTCTC TTTTCATCCT TCCCTTCTTC CCTCCTTTCC TCCTCTTTTC CCTCTTCTCC    34980

CCCCTCCTCC CCTCCTTCCT CCTCCCATTC CCCCTCCTCC CCCCTCCCAT TCCCCCTCCT    35040

CCCCTCCTTC CTCCTCCCAT TACCCCTCCT CTCCTCCCCT CCTCCCACCC CCCTCTCCTC    35100

CCGGCTCCTC TCCTCCCCTC CTCATCCCCC TCCTCTCCTT CCCTCCTAAC CCCCCTCCTC    35160

TCCTCCCCTC CTCATCCCCC TCCTCTCCTT CCCTCCTCCT ATCCCCCCTC CTCTCCTCCC    35220

CTCCTCCTAT TCCCCCTCCT CTCCTCCCCT CCTTCCTCCT CCTCTCCTCC CATGCCCCCT    35280

CCTCCCCTCC TCCCATCCCC CTCCTCCCCT CCTCCCTCCT CCCATCCCAT CCCCCTCCTC    35340

TCCTCCCCTT CTCTCCCCTC CTCTCCTCCC CTCCTCTCCT CTCCTCCTCT CCTCCCCTCC    35400

TCCCATCCCC CCTCCTCCCA TCCCCCCTCC TCTCCTCCCC ACTCCTCTCC TCCCCACTCC    35460

TCTCCTCCCC TCATCCCCCT CCTCTCTCCT CCCCTCCCCC TCCTCTCCTT CCCTCCTCCT    35520

TTCCTCCCCT CCCCCTCCTT CCCCCTCCTC CCCCTCCTTC TCCCCATCCC CCTTCCCCTT    35580

CTCCTCCTCT CCCCTCCCCC TTCTCTTTTT CCCTCCTCCT CCCTTCCTCC TCCCCTCTTC    35640

TCCCCTTTTC CCTTTTCTCT TCCTCTCCTC CCCTTCTCCC CTCCTGTCCT CCCTCCCTTT    35700

CTCTCTTTCT TTCCTCCCTT TCCTTCTCCC CTGTTCTCCT CCCTTCCCTT CTCCCCTTTT    35760

CTTCCCTCCT CCTTTCCTCC CCTCCTCCTT TTCTCTGTTT CTCTTCCTTT CCCCTCCACT    35820

TTCCCCTTCC TTTCCCCTCT CCTTTCTCCT TCCTTTCCTC TCCCCTTCTC TTCCTTTTCC    35880

TCTCTCCCCT TCTTTTCCCT CTTCCCCTCC CCTCCTCTTC CCCTCCCCTC CTCTTCCCCT    35940

CCCCTCCTCT TCCCCTCCCC TCCTCTTCCC CTCTCCTCCT CTTCCCCTCC CCTCCTCTTT    36000

CCCTCCCCTC TTCTCCTCCC CTCCTCTCCC CTCTTCCCCT CCCCTCCTCT TCCCTCCCCT    36060

TCCCCTCCCC TCCTCTTCCC TCCCCTTCCC CTCCCCTCCT CTTCCCTCCC CTTCCCCTCC    36120

TCTTCCTTCC TCTCTTCCCC TCCCCTCCTC TTCCCTCCCC TCTTCCCCTC CCCTTCTCTT    36180

CTCCTCCCCT TCTCTTCCCC TCCCCTTTTC TTCCCTCTCC TTGTCTTCCC TGCCCTCCTC    36240

TTCCCTCCCC TCCTCTTCCC TCCCCTCTTC CCCTCTCCTC CTCTTCCCTC CCCTCTTCCT    36300

CTTTCCTCTT CCCCTCCCCT CCTCCTCCCT CCCCTTTCCC CTCTTCCCCT CCCCTCCGCT    36360

TCCCTCCCCT TTCTCCCCCT TCTCTCCCCT CCCCTCTCCC CCCTTCTCTC CCCTCCCCTC    36420

TCCCCCTTCT CTCCCCTCCC CTCTCCCCCT TCTCTCCCCT CTCCTCTCCC CCTTCTCTCC    36480
```

```
CCCTTCTCTC CCCCTTCTCT CTCCCCTTCT CTCCCCCTTC TCTCCCCTCC CCCCTTCTCT    36540
CCCCTCCCCT CTCCCCCTTC TCTCCCCTCC CCTCTCCCCT GTCCTCTCCT CTCCACCCTT    36600
CTCTCCCCTC CCCTCTCCTC TCCCCCTTCC CTCTCCTCTC CCCCTTCTCT CCCCTCCCCT    36660
CTCCTCTCCC CCCTTTTCTC CACTCCCCTC TCCTCTCTCC CCTCCTCCTC CGCTCTCATG    36720
TGAAGAGGTG CCTTGTGTGG TCGGTGGGCT GCATCACGTG GTCCCCAGGT GGAGGCCCTG    36780
GGTCATGCAG AGCCACAGAA AATGCTTAGT GAGGAGGCTG TGGGGGTCCA GTCAAGTGGG    36840
CTCTCCAGCT GCAGGGCTGG GGGTGGGAGC CAGGTGAGGA CCCGTGTAGA GAGGAGGGCG    36900
TGTGCAAGGA GTGGGGCCAG GAGCGGGGCT GGACACTGCT GGCTCCACAC AGGGGCCCAG    36960
CAGGGAGCTC GTATGCCGCT CGTGCCTGAA GCAGACGCTG CACAAGCTGG AGGCCATGAT    37020
GCTCATCCTG CAGGCAGAGA CCACCGCGGG CACCGTGACG CCCACCGCCA TCGGAGACAG    37080
CATCCTCAAC ATCACAGGTG CCGCGGCCCG TGCCCCATGC CACCCGCCCG CCCCGTGCGG    37140
CCCTTTCCTC TGCCTCCCTC CTCCCCCCAA CCGCGTCGCC TTTGCCCCAT CCCATCTTCG    37200
TCCCCCTCCC CTCCCCCCAA TTCCCATCCT CATCCCCCTC CCCCAATTCC CATTCTCCTC    37260
CCCCTCCCCC TTCCCTATTA CCATCCCTTT TCTCCATCTC TCTCCCCTTT TCTCCATTTC    37320
CCCCCCCGTC CTCCCCGTCC TTTTGTCCAT TCCCCTCATC TTCCTCATCC CCCTCATCCC    37380
CCTTCCCCTC CCTTATCCCC CTTCCCCTCC CTTTCCCCCT GCTCCTCTTC TTCTCCCTTC    37440
TCTTTTCTCT ACCCTTTTCC TTCCTTTTTC CTCCCTCTCC CCATCATCCC CCTCATCTTC    37500
GTCCTCATCC CCATCACCTT CCCCCTCCCC CCTCCACCAC TCTCTCTCCA GCTTCCCCCT    37560
TCCTTCTGCC TGCACCTCGC TCTCTGCCCC CTCAGGTTCC CCCTTTCTCC CAGCCCCCAC    37620
CCTCCGGCTC CCCCTTTTTG CCTGCCCCCA CCCTCCCTCT ACCTCCCTGT CTCTGCACTG    37680
ACCTCACGCA TGTCTGCAGG AGACCTCATC CACCTGGCCA GCTCGGACGT GCGGGCACCA    37740
CAGCCCTCAG AGCTGGGAGC CGAGTCACCA TCTCGGATGG TGGCGTCCCA GGCCTACAAC    37800
CTGACCTCTG CCCTCATGCG CATCCTCATG CGCTCCCGCG TGCTCAACGA GGAGCCCCTG    37860
ACGCTGGCGG GCGAGGAGAT CGTGGCCCAG GGCAAGCGCT CGGACCCGCG GAGCCTGCTG    37920
TGCTATGGCG GCGCCCCAGG GCCTGGCTGC CACTTCTCCA TCCCCGAGGC TTTCAGCGGG    37980
GCCCTGGCCA ACCTCAGTGA CGTGGTGCAG CTCATCTTTC TGGTGGACTC CAATCCCTTT    38040
CCCTTTGGCT ATATCAGCAA CTACACCGTC TCCACCAAGG TGGCCTCGAT GGCATTCCAG    38100
ACACAGGCCG GCGCCCAGAT CCCCATCGAG CGGCTGGCCT CAGAGCGCGC CATCACCGTG    38160
AAGGTGCCCA ACAACTCGGA CTGGGCTGCC CGGGGCCACC GCAGCTCCGC CAACTCCGCC    38220
```

```
AACTCCGTTG TGGTCCAGCC CCAGGCCTCC GTCGGTGCTG TGGTCACCCT GGACAGCAGC    38280
AACCCTGCGG CCGGGCTGCA TCTGCAGCTC AACTATACGC TGCTGGACGG TGCGTGCAGC    38340
GGGTGGGGCA CACGCGGCCC CCTGGCCTTG TTCTTCGGGG GAAGGCGTTT CTCGTAGGGC    38400
TTCCATGGGT GTCTCTGGTG AAATTTGCTT TCTGTTTCAT GGGCTGCTGG GGGCCTGGCC    38460
AGAGAGGAGC TGGGGGCCAC GGAGAAGCAG GTGCCAGCTC TGGTGCAGAG GCTCCTATGC    38520
TTTCAGGCCC GTGGCAGAGG GTGGGCTCAG GAGGGCCATC GTGGGTGTCC CCCGGGTGGT    38580
TGAGCTTCCC GGCAGGCGTG TGACCTGCGC GTTCTGCCCC AGCCACTAC CTGTCTGAGG     38640
AACCTGAGCC CTACCTGGCA GTCTACCTAC ACTCGGAGCC CCGGCCCAAT GAGCACAACT    38700
GCTCGGCTAG CAGGAGGATC CGCCCAGAGT CACTCCAGGG TGCTGACCAC CGGCCCTACA    38760
CCTTCTTCAT TTCCCCGGGG TGAGCTCTGC GGGCCAGCCT GGCAGGGCAG GGCAGGGCAT    38820
CATGGGTCAG CATTGCCTGG GTTACTGGCC CCATGGGGAC GGCAGGCAGC GAGGGGACTG    38880
GACCGGGTAT GGGCTCTGAG ACTGCGACAT CCAACCTGGC GGAGCCTGGG CTCACGTCCG    38940
CTACCCCTTC CCTGCCCAGG AGCAGAGACC CAGCGGGGAG TTACCATCTG AACCTCTCCA    39000
GCCACTTCCG CTGGTCGGCG CTGCAGGTGT CCGTGGGCCT GTACACGTCC CTGTGCCAGT    39060
ACTTCAGCGA GGAGGACATG GTGTGGCGGA CAGAGGGCT GCTGCCCCTG GAGGAGACCT     39120
CGCCCCGCCA GGCCGTCTGC CTCACCCGCC ACCTCACCGC CTTCGGCGCC AGCCTCTTCG    39180
TGCCCCCAAG CCATGTCCGC TTTGTGTTTC CTGTGAGTGA CCCTGTGCTC CTGGGAGCCT    39240
CTGCAGAGTC GAGGAGGGCC TGGGTGGGCT CGGCTCTATC CTGAGAAGGC ACAGCTTGCA    39300
CGTGACCTCC TGGGCCCGGC GGCTGTGTCC TCACAGGAGC CGACAGCGGA TGTAAACTAC    39360
ATCGTCATGC TGACATGTGC TGTGTGCCTG GTGACCTACA TGGTCATGGC CGCCATCCTG    39420
CACAAGCTGG ACCAGTTGGA TGCCAGCCGG GGCCGCGCCA TCCCTTTCTG TGGGCAGCGG    39480
GGCCGCTTCA AGTACGAGAT CCTCGTCAAG ACAGGCTGGG GCCGGGGCTC AGGTGAGGGG    39540
CGCAGCGGGG TGGCAGGGCC TCCCCTGCTC TCACTGGCTG TGCTGGTTGC ACCCTCTGGG    39600
AGTGAGTCTC GTCGCAGGCG TCAGAACAAG GCAGTTTTTG CAGTGCTGTG TGAAGGGCTC    39660
GTGTGTTCAT CCTGGGAATG ACCTCGTGAG CACTCACTGT CCCTGAGGAC TAGGACAGCT    39720
CCTAGCTGGA AGTAGGTGCC AGTCAGTCAG GGTGGGCAGC CCACGTTCTG CACAGTAGCG    39780
TGGCCCCACA AGTGACGTGA GCATCGCTAC CACTGTGGGA GACTGTGCAT CCACCCGCGA    39840
TCCTGACTGC ATAGCTCGTC TCTCAGACGG AGGCGCCAGC ACCCTCCCCG TGGCTGTTTC    39900
TTCAGTACCT CCATTTTCCT TTCATTGGAA TTGCCCTTCT GGCATTCCCT TTTTGTTTTC    39960
```

```
GTTTTTCTTT TTTTAGAGAC GGAGTCTCAC TCTGTTGCCC AGGCTGGAGT GCAATGGCAT  40020
GATCTTGGCT CACAGCAACT TCCAGCTCCC GGGTTAAGC CATTCCCCTT AAGCGATTCT  40080
CCTGAGTAGC TGGGAGTACA GGTGCACACC ACCACACCCA GTTAATTTTT CACCATGTCA  40140
GCCAGGCGAA CTCCTGACCT CAGGTGATCC GCCTGCCTCG GCCTGCCAGA GTGCTGGGAT  40200
GACAGGTGTG AGCCACCACA CCTGGCTGTG TTCCCATTTT TTATCTCTGT GCTGCTTTCC  40260
TCTTCATTGC CCAGTTCTTT CTTTTGATTA CCTACTTTTA AAAACTGTCG GCCGGGCGCG  40320
GTGGCTCACA CCTGTAATCC GAGCACTTTG GGAGGCCAGG CAGGCAAATC ACGGGGTCAG  40380
GAGATCGAGA CCATCCTGGC TAACGGTGAA ACCCTGTCTC TAATAAAAAG TACAAAAAAA  40440
TTAGCCCGGC GTAGTGGCAG GCGCCTGTAG TCCAGCTCC TTGGGAGACT GAGGCAGGAG  40500
AATGGCGTGA ACCCGGGAGG CGGAGCTTGC AGTGAGCTGA GATTGCGCCA CTGCACTCCA  40560
GCCTGGGTGA CACAGCAAGA CTCCATCTCA AAAAAAAAG AAAAAAATA CTGTCACCTG  40620
GGTCTGTCAC TGGGAGAGGA GGTGACACAG CTTCACGCTT TGCAGTCTGT GCATGAACTG  40680
AGGGACGGGT GTGTGGTGCG GGTCACCGGT TGTGGCATGA CTGAGGCGTG GACAGGTGTG  40740
CAGTGCGGGT CACTGGTTGT GGTGTGGACT GAGGCGTGTG CAGCCATGTT TGCATGTCAC  40800
AAGTTACAGT TCTTTCCATG TAACTTAATC ATGTCCTTGA GGTCCTGCTG TTAATTGGAC  40860
AAATTGCAGT AACCGCAGCT CCTTGTGTAT GGCAGAGCCG TGCAAAGCCG GGACTGCCTG  40920
TGTGGCTCCT TGAGTGCGCA CAGGCCAAAG CTGAGATGAC TTGCCTGGGA TGCCACACGT  40980
GTTGGGCAGC AGACCGAGCC TCCCACCCCT CCCTCTTGCC TCCCAGGTAC CACGGCCCAC  41040
GTGGGCATCA TGCTGTATGG GGTGGACAGC CGGAGCGGCC ACCGGCACCT GGACGGCGAC  41100
AGAGCCTTCC ACCGCAACAG CCTGGACATC TTCCGGATCG CCACCCCGCA CAGCCTGGGT  41160
AGCGTGTGGA AGATCCGAGT GTGGCACGAC AACAAAGGTT TGTGCGGACC CTGCCAAGCT  41220
CTGCCCCTCT GCCCCGCAT TGGGGCGCCC TGCGAGCCTG ACCTCCCTCC TGCGCCTCTG  41280
CAGGGCTCAG CCCTGCCTGG TTCCTGCAGC ACGTCATCGT CAGGGACCTG CAGACGGCAC  41340
GCAGCGCCTT CTTCCTGGTC AATGACTGGC TTTCGGTGGA GACGGAGGCC AACGGGGGCC  41400
TGGTGGAGAA GGAGGTGCTG GCCGCGAGTA AGGCCTCGTT CCATGGTCCC ACTCCGTGGG  41460
AGGTTGGGCA GGGTGGTCCT GCCCCGTGGC CTCCTGCAGT GCGGCCCTCC CTGCCTTCTA  41520
GGCGACGCAG CCCTTTTGCG CTTCCGGCGC CTGCTGGTGG CTGAGCTGCA GCGTGGCTTC  41580
TTTGACAAGC ACATCTGGCT CTCCATATGG GACCGGCCGC CTCGTAGCCG TTTCACTCGC  41640
ATCCAGAGGG CCACCTGCTG CGTTCTCCTC ATCTGCCTCT TCCTGGGCGC CAACGCCGTG  41700
```

```
TGGTACGGGG CTGTTGGCGA CTCTGCCTAC AGGTGGGTGC CGTAGGGGTC GGGGCAGCCT   41760
CTTCCTGCCC AGCCCTTCCT GCCCCTCAGC CTCACCTGTG TGGCCTCCTC TCCTCCACAC   41820
AGCACGGGGC ATGTGTCCAG GCTGAGCCCG CTGAGCGTCG ACACAGTCGC TGTTGGCCTG   41880
GTGTCCAGCG TGGTTGTCTA TCCCGTCTAC CTGGCCATCC TTTTTCTCTT CCGGATGTCC   41940
CGGAGCAAGG TGGGCTGGGG CTGGGGACCC GGGAGTACTG GAATGGAGC CTGGGCCTCG    42000
GCACCATGCC TAGGGCCGCC ACTTTCCAGT GCTGCAGCCA GAGGGAAAGG CGTCCACCAA   42060
AGGCTGCTCG GGAAGGGTCA ACACACTTGA GCAGCCTTAG CTAGACTGAC CAGGGAGAAA   42120
GAGAGAAGAC TCAGAAGCCA GAATGGTGAA AGAACGAGGG CACTTTGCTA AGCAGACGCC   42180
ACGGACGACT GCACAGCAGC ACGCCAGATA ACTCAGAAGA AGCAAGCACG CGGCTGTGCA   42240
CGCTTCCGAA ATGCACTCCA GAAGAAAATC TCAGTACATC TATAGGAAGT GAAGAGGCTG   42300
AGTTAGTCCC TTAGAAACGT CCCAGTGGCC GGGCCGGGTG TGGTGGCTCA CGCCTGTAAT   42360
CCCAACACTT CAGGTGGCCG AGGTGGGCGG ATCTGAGTCC AGGAGTTTGA GACCAGCCTG   42420
GGCAACATAG CAAGACCCCA TCTATATAAA ACATTAAAAA GGGCCAGGCG CGGTGGCTCA   42480
CGCCTGTAAT CCCAGCACTT TGGGAGGCCG AGGCGGGCAG ATCACTTGAG GTCAGGAGTT   42540
CGAGACCAGC CTGGCCAACA CAATGAAACC CCGACTCTAC TACAAATACA AAAACTTAGC   42600
TGGGCATGGT GGCGGGCGCC TGTAGTCCCA GCTACTCGAG AGGCTGAGGC AGGAGAATGG   42660
CATGAACCCA GGAGGCGGAG CTTGCAGTGA GCCGAGATTG CGCCACTGCA CTCCATCCTG   42720
GGCAACGGAG CAAGACTCCA TCTCCAAAAA AAAAAAAAAA AAATCCCACA AGAAAAGCT   42780
CAGGCTCAGA GCCTTCACGA TAGAATTTTT CTAAGCAGTT AAGGAAGAAT TAACACCAAT   42840
CCTTCACAGA CTCTTTCCAA GAATACAGCA GGTGGGAACG CTTCCCATTC ATACGGAAAC   42900
GGGAGGCCGC ACCCCTTAGG AATGCACACG TGGGGTCCTC AAGAGGTTAC ATGCAAACTA   42960
ACCCCAGCAG CACACAGAGA AGGCGCATAA GCCGCGACCA GGAGGGGTTG CTCCCGAGTC   43020
CGTGGCAGGA ACCAGAGGCC ACATGTGGCT GCTCGTATTT AAGTTAATTA AAATGGAACG   43080
ATGGCCGGGT GTGGTGGCTC ACACCTGTAA TCCCAGCACT TGGGAGGCG GAGGCGGGCA    43140
GATCACTTGA GGTCAGGAGT TCCAAGACCA GCCTGGCCAA CACAGTGAAA CCCCGTCTCT   43200
ACTAAAAATA CAAAAAATTA GCTGGGCATG GTGGCAGGCA CCTGTAATCC CAGCTACTCA   43260
GGAGGCTGAG CCAGGACAAT CGCCTGAACG CGGGAGGTGG AGGTTGCAGT GAGCTGAGAT   43320
TGCGCCATTG CACTCCAGCC TGGGTGACAG CGAGACTCCA TCTAAAAAAG AAAATATGAA   43380
ATTTAAAACT CTGTTCCTTA GCTGCACCAG TCTGCTGTCA AGTGTTCAGT GGCACACGTC   43440
```

```
GCGAGGGGCT GCCATCACGG ACGGTGCAGA TGTCCCATAT ATCCAGCATT CTAGGACATT    43500

CTGTCAGATG GCACCGGGCT CTGTCCTGTC TGCTGAGGAG GTGGCTTCTC ATCCCTGTCC    43560

TGAGCAGGTC TGAGCTGCCG CCCGCTGACC ACTGCCCTCG TCCTGCAGGT GGCTGGGAGC    43620

CCGAGCCCCA CACCTGCCGG GCAGCAGGTG CTGGACATCG ACAGCTGCCT GGACTCGTCC    43680

GTGCTGGACA GCTCCTTCCT CACGTTCTCA GGCCTCCACG CTGAGGTGAG GACTCTACTG    43740

GGGGTCCTCG GCTGGGCTGG GGTCCTGCC GCCTTGGCGC AGCTTGGACT CAAGACACTG    43800

TGCACCTCTC AGCAGGCCTT TGTTGGACAG ATGAAGAGTG ACTTGTTTCT GGATGATTCT    43860

AAGAGGTGGG TTCCCTAGAG AAACCTCGAG CCCTGGTGCA GGTCACTGTG TCTGGGGTGC    43920

CGGGGGTGTG CGGGCTGCGT GTCCTTGCTG GGTGTCTGTG GCTCCATGTG GTCACACCAC    43980

CCGGGAGCAG GTTTGCTCGG AAGCCCAGGG TGTCCGTGCG TGACTGGACG GGGGTGGGCT    44040

GTGTGTGTGA CACATCCCCT GGTACCTTGC TGACCCGCGC CACCTGCAGT CTGGTGTGCT    44100

GGCCCTCCGG CGAGGGAACG CTCAGTTGGC CGGACCTGCT CAGTGACCCG TCCATTGTGG    44160

GTAGCAATCT GCGGCAGCTG GCACGGGGCC AGGCGGGCCA TGGGCTGGGC CCAGAGGAGG    44220

ACGGCTTCTC CCTGGCCAGC CCCTACTCGC CTGCCAAATC CTTCTCAGCA TCAGGTGAGC    44280

TGGGGTGAGA GGAGGGGGCT CTGAAGCTCA CCCTTGCAGC TGGGCCCACC CTATGCCTCC    44340

TGTACCTCTA GATGAAGACC TGATCCAGCA GGTCCTTGCC GAGGGGGTCA GCAGCCCAGC    44400

CCCTACCCAA GACACCCACA TGGAAACGGA CCTGCTCAGC AGCCTGTGAG TGTCCGGCTC    44460

TCGGGGAGG GGGGATTGCC AGAGGAGGGG CCGGGACTCA GGCCAGGCAG CCGTGGTTCC    44520

CGCCTGGGGT AGGGTGGGGT GGGGTGCCAG GGCAGGGCTG TGGCTGCACC ACTTCACTTC    44580

TCTGAACCTC TGTTGTCTGT GGAAAGAGCC TCATGGGATC CCCAGGGCCC CAGAACCTTC    44640

CCTCTAGGGA GGGAGCAGGC TCATGGGGCT TTGTAGGAGC AGAAAGGCTC CTGTGTGAGG    44700

CTGGCCGGGG CCACGTTTTT ATCTTGGTCT CAGAGCAGTG AGAAATTATG GCGGGTTTT    44760

TAAATACCCC ATTTTTGGCC GGGCGCGGTG GCTCACACGT GTAATCCCAG CACTTTGGGA    44820

GGCCGAGGTG GGCAGATGAC CTGAGGTCAG CAGTTCGAGA CCAGCCTGGC CAACATGGCG    44880

AAACCCCGTC TCTACTAAAA ATACAAAAAA TTAGCCGGGC ATGCTGGCAG GCGCCTGTAG    44940

TCCCAGTTAC TCGGGAGACT GAGGTAGGAG AATCGATTGA ACCTGGTAGG TGAAGGTTGT    45000

AGTGAGCCGA GATCGCGCCA CTGCACTCCA GCCTGGGCAA CAAGAGCGAA ACTCCGTCTC    45060

AAAAACAAAA AAATTCCTCA ATTTCTTGGT TGTTTTGTAA CTTATCAACA AATGGTCATA    45120

TAGAGGTTAC CTTGTATGTA GTCACGCACA TAGTCACGCA CATGGCAGCC GGCGGCGGAG    45180
```

```
CGCACCCACG GCGTGTTCCC ACGCGTGTGA CCCCGGGCTC TGCCATGCCC TCCTATGCTC   45240
AGGTGTGCTG AGGTCCACAC GGCCCTGCCG TTGCACTGCA GCTGCCTGCA GGATTCAGTG   45300
CAGTGGCATG CAGTGCAGGT GCGGTGCCCC GGAGCCACAG GCCACACCAC AGGGCCTGCA   45360
TGCACAGGGG CTGCGGTGTC TGGGTTTGGG TAACTACGCC CTGTGACATT TGCACAGCAA   45420
CAGAATTACC TAATGACGCA TTTCTCAGAA CACATCCCTG GCACTAAGTG GTGCGTGACT   45480
GCTGCTTTTG CATCCACATC TAGTTTGATT TGTGTGTTAT TCCTTTGAGT GCTTCTCATT   45540
GTTAAGCAAC CAAGAACTAA AGAGGTATGA ACTGCCCCTG GACTCAAACA AAAAGGAAAA   45600
CTTCCTGATT TACAAAGGC AGATAACCAT CACATGAGGG CATCTTTATG AATAAATTGC   45660
TGGTTGGTTT TAAAAATACA GAGTATGGGG AAATCCAGGG GTAGTCACTA CATGCTGACC   45720
AGCCCCAGGT ATCTCCGGCC CAAAGCTCTG TGAAATCCAG ATTCAGTGCT TCCGCGGGGA   45780
TTTCTGACGG CAGCTCAGAC TCCGCATCCA CACAGAGCGC GTGGCCCTCA CCCTCCCGGC   45840
TTCCTCAACC CTTGGCCGTC CCTTGCTCGG ACAGTGCTTC GGGCTGACCA GGTCGGAGGC   45900
TTGGGTTTGT CCTGGACCCC TCTGCGTCCT TCCTCACTGC AGCCTCCAGC GCGTCCCGTG   45960
GCTCCTTTCC CAACGCAGAG CACGGCCTTC CCTGCGCCTG AGCCTGCACC CTCCGTCCTG   46020
GCGGCGCCTC TGCCCTGGCA TTCCCTGCCA CTCCATGCCT CCCTATTGGC CATTCTCCGT   46080
CTCTGCCAGC GAGAGCCTGC TCCCTGAGTC AGACCCTGAG TCATTTGTGT TGCTATAAAG   46140
GAATAGTTGA GGCTGGGTTA TTTTTTATTT TTATTTATTT TTTTGAGATG GAGTCTCTGT   46200
TGCCCAGACT GGAGTGCAGT CGCATGATCT CGGCTCACTG CAAAGTCTGC CTCCCACGTT   46260
CAAGCAGTTA TCTGCCTCAG CCTCCCAAGT AGCTAAGATT ACAGGCGCCC GCCGCCACAG   46320
CCCGCTAATT TTTTGTGTGT GTGTTTTAGT AGAGAGGAGG TTTCACCATC TTAGCCAGGC   46380
TGGTCTTGAA CTCCTGACCT CGTGATCCAC CCATCTCAGC CTCCCAAAAT GCTGAGATTA   46440
CAGGCGTGAG CCACCACGCC TGACCAAGTT GAGGCTAGGT CATTTTTAA TTTTTTGTAA   46500
AGACAGGGTC TCACTGTCTC CAACTCCTGA GCTCAAGTGA TCCTCCTGCC TCAGCCTCCT   46560
GAAGTGCTGG GATTACAGGC TTGAGACACT GCGCCCAGCC AAGAGTGTCT TTTATCCTCC   46620
GAGAGACAGC AAAACAGGAA GCATTCAGTG CAGTGTGACC CTGGGTCAGG CCGTTCTTTC   46680
GGTGATGGGC TGACGAGGC GCAGGTACGG GAGAGCGTCC TGAGAGCCCG GGACTCGGCG   46740
TCTCGCAGTT GGTCTCGTCC TCCCCCTCAA CGTGTCTTCG CTGCCTCTGT ACCTCTTCTC   46800
TAGCAGCTCT GGGACCGGGC ATATCAGCAT GGTGGCCCGA TGCAGTGGCA CAGCCTCGGT   46860
GGTCACTGGC TCCTGGAGAC ACAAGCAGAT CTCTGGCCTC AGGGAGCCCT ACACACTGTT   46920
```

```
GGGATTTGAA AGGCATTCAT ATGTTTCCTT GTCCAGAAGT TAATTTTAGG CCATAAACCT    46980
GCATGGGACA GACACACTGG CGTCTCTAGA TTGTAGAGAT GCTTGTTGGA TGGTTGAGAC    47040
CCAATCATAG TTTGCAGGGT TGAAGGGGGG CTCATTGCAC CCTGAGAGAC TGTGCACTGC    47100
TGTAAGGGCA GCTGGTCAGG CTGTGGGCGA TGGGTTTATC AGCAGCAAGC GGGCGGGAGA    47160
GGGACGCAGG CGGACGCCTG ACTTCGGTGC CTGGAGTGGC TCTTGGTTCC CTGGCTCCCA    47220
GCACCACTCC CACTCTCGTT TGGGGTAGGG TCTTCCGGCT TTTTGTCGGG GGGACCCTGT    47280
GACCCAAGAG GCTCAAGAAA CTGCCCGCCC AGGTTAACAT GGGCTTGGCT GCAACTGCCT    47340
CCTGGAGGCC GGGATGAATT CACAGCCTAC CATGTCCCTC AGGTCCAGCA CTCCTGGGA    47400
GAAGACAGAG ACGCTGGCGC TGCAGAGGCT GGGGGAGCTG GGCCACCCA GCCCAGGCCT    47460
GAACTGGGAA CAGCCCCAGG CAGCGAGGCT GTCCAGGACA GGTGTGCTTG CGTAGCCCCG    47520
GGATGCCCCT AGCCCCTCCC TGTGAGCTGC CTCTCACAGG TCTGTCTCTG CTTCCCCAGG    47580
ACTGGTGGAG GGTCTGCGGA AGCGCCTGCT GCCGGCCTGG TGTGCCTCCC TGGCCCACGG    47640
GCTCAGCCTG CTCCTGGTCG CTGTGGCTGT GGCTGTCTCA GGGTGGGTGG GTGCGAGCTT    47700
CCCCCCGGGC GTGAGTGTTG CGTGGCTCCT GTCCAGCAGC GCCAGCTTCC TGGCCTCATT    47760
CCTCGGCTGG GAGCCACTGA AGGTGAGGGG GCTGCCAGGG GTAGGCTACA GGCCTCCATC    47820
ACGGGGACC CCTCTGAAGC CACCCCCTCC CCAGGTCTTG CTGGAAGCCC TGTACTTCTC    47880
ACTGGTGGCC AAGCGGCTGC ACCCGGATGA AGATGACACC CTGGTAGAGA GCCCGGCTGT    47940
GACGCCTGTG AGCGCACGTG TGCCCCGCGT ACGGCCACCC CACGGCTTTG CACTCTTCCT    48000
GGCCAAGGAA GAAGCCCGCA AGGTCAAGAG GCTACATGGC ATGCTGCGGG TGAGCCTGGG    48060
TGCGGCCTGT GCCCCTGCCA CCTCCGTCTC TTGTCTCCCA CCTCCCACCC ATGCACGCAG    48120
GACACTCCTG TCCCCCTTTC CTCACCTCAG AAGGCCCTTA GGGGTTCAAT GCTCTGCAGC    48180
CTTTGCCCGG TCTCCCTCCT ACCCCACGCC CCCACTTGC TGCCCCAGTC CCTGCCAGGG    48240
CCCAGCTCCA ATGCCCACTC CTGCCTGGCC CTGAAGGCCC CTAAGCACCA CTGCAGTGGC    48300
CTGTGTGTCT GCCCCCAGGT GGGGTTCCGG GCAGGGTGTG TGCTGCCATT ACCCTGGCCA    48360
GGTAGAGTCT TGGGGCGCCC CCTGCCAGCT CACCTTCCTG CAGCCACACC TGCCGCAGCC    48420
ATGGCTCCAG CCGTTGCCAA AGCCCTGCTG TCACTGTGGG CTGGGGCCAG GCTGACCACA    48480
GGGCCCCCCC GTCCACCAGA GCCTCCTGGT GTACATGCTT TTTCTGCTGG TGACCCTGCT    48540
GGCCAGCTAT GGGGATGCCT CATGCCATGG GCACGCCTAC CGTCTGCAAA GCGCCATCAA    48600
GCAGGAGCTG CACAGCCGGG CCTTCCTGGC CATCACGCGG TACGGGCATC CGGTGCACTG    48660
```

```
GTCTGTCTTC TGGGCTTTAG TTTTGCCTTT AGTCCAGCCA GACCCTAGGG GACATGTGGA    48720
CATGTGTAGA TACCTTTGTG GCTGCTAGAA CTGGAGGTAG GTGCTGCTGG CATCAGTAGG    48780
CAGAGGGGAG GGACACAGGT CCGTGTCTTG CAGTGCACAG GACGGGCCCA TGACAGACAA    48840
CTGTCTGCCC CAGAACATCC CAGGATAAG GCTGAGAAGC CAGGTCTAG CCGTGGCCAG      48900
CAGGGCAGTG GGAGCCATGT TCCCTGGGTC TCTGGTGGCC GCTCACTCGA GGCGGGCATG    48960
GGGCAGTAGG GGCTGGAGCG TGTGACTGAT GCTGTGGCAG GTCTGAGGAG CTCTGGCCAT    49020
GGATGGCCCA CGTGCTGCTG CCCTACGTCC ACGGGAACCA GTCCAGCCCA GAGCTGGGGC    49080
CCCCACGGCT GCGGCAGGTG CGGCTGCAGG AAGGTGAGCT GGCAGGGCGT GCCCCAAGAC    49140
TTAAATCGTT CCTCTTGTTG AGAGAGCAGC CTTTAGCGGA GCTCTGGCAT CAGCCCTGCT    49200
CCCTAGCTGT GTGACCTTTG CCCTCTTAAC ACCGCCGTTT CCTTCTCTGT ATATGAGAGA    49260
TGGTAACGTT GTCTAATTCA TGGCTGCTGG GAGGGTTCCC TGGGGTGGCG CCGAACCAGA    49320
GCTCAGGCGA GCTGGCCAGC AGGAAACACT CCTGTTGGGT TTTGATGAGG CCCTGGCCCC    49380
GGCCTGGGGC TCTGTGTGTT TCAGCACTCT ACCCAGACCC TCCCGGCCCC AGGGTCCACA    49440
CGTGCTCGGC CGCAGGAGGC TTCAGCACCA GCGATTACGA CGTTGGCTGG GAGAGTCCTC    49500
ACAATGGCTC GGGGACGTGG GCCTATTCAG CGCCGGATCT GCTGGGGTGA GCAGAGCGAG    49560
GGCCCCGGGC GTCTACGCCA AGGACAAGGG AGTAGTTCTC CAGGAGTGCC GCGGCCTCCT    49620
GACCAGCCTG GCTCCGGGGT GCCGGAAGGG CTGGGGTGCG GCACCCACGC CACCCCTCTC    49680
CGGCAGGGCA TGGTCCTGGG GCTCCTGTGC CGTGTATGAC AGCGGGGGCT ACGTGCAGGA    49740
GCTGGGCCTG AGCCTGGAGG AGAGCCGCGA CCGGCTGCGC TTCCTGCAGC TGCACAACTG    49800
GCTGGACAAC AGGTGGGAGC TCCCTCCCCT GCCCTCTCCG GGTGGCCGC AGTCACCAGC     49860
CAGGAGCCCA CCCTCACTCC TCCGGCCCCC GCTGGCCTAG GCGGCTTCCA CAGCCCCTCA    49920
GCCACGCCTG CACTGCGCGG TCCCCGCAGC TCCCGCCCTG CCACCCGCTC CTACTGACCC    49980
GCACCCTCTG CGCAGGAGCC GCGCTGTGTT CCTGGAGCTC ACGCGCTACA GCCCGGCCGT    50040
GGGGCTGCAC GCCGCCGTCA CGCTGCGCCT CGAGTTCCCG GCGGCCGGCC GCGCCCTGGC    50100
CGCCCTCAGC GTCCGCCCCT TTGCGCTGCG CCGCCTCAGC GCGGGCCTCT CGCTGCCTCT    50160
GCTCACCTCG GTACGCCCGT CCCCGGCCAG ACCCCGCGCC TCCCACCGGC AGCGTCCCGC    50220
CCCCTCGCGG GGCCCCGCCC GGCAGCGTCT CACCCCTCGC AGCGCCCCGC CCCTCGCAG    50280
CGTCCCGCCC CCTCGCAGGG CCCCGCCCCG GCAGCGTCCC GCCCCCTCGT AGGGCCCCGC    50340
CCCGGCAGCG TCCCGCCCCC TCGCAGGGCC CCGCCCCGGC AGCGTCCCTC CGCCCTCCT    50400
```

```
GACCGCGCCC CCCACAGGTG TGCCTGCTGC TGTTCGCCGT GCACTTCGCC GTGGCCGAGG    50460
CCCGTACTTG GCACAGGGAA GGGCGCTGGC GCGTGCTGCG GCTCGGAGCC TGGGCGCGGT    50520
GGCTGCTGGT GGCGCTGACG GCGGCCACGG CACTGGTACG CCTCGCCCAG CTGGGTGCCG    50580
CTGACCGCCA GTGGACCCGT TTCGTGCGCG GCCGCCCGCG CCGCTTCACT AGCTTCGACC    50640
AGGTGGCGCA GCTGAGCTCC GCAGCCCGTG GCCTGGCGGC CTCGCTGCTC TTCCTGCTTT    50700
TGGTCAAGGT GAGGGCTGGG CCGGTGGGCG CGGGGCTGGG CGCACACCCC AGGGCTGCAA    50760
GCAGACAGAT TTCTCGTCCG CAGGCTGCCC AGCAGCTACG CTTCGTGCGC CAGTGGTCCG    50820
TCTTTGGCAA GACATTATGC CGAGCTCTGC CAGAGCTCCT GGGGTCACC TTGGGCCTGG     50880
TGGTGCTCGG GGTAGCCTAC GCCCAGCTGG CCATCCTGGT AGGTGACTGC GCGGCCCGCG    50940
AGGGCGTCTT AGCTCAGCTC AGCTCAGCTG TACGCCCTCA CTGGTGTCGC CTTCCCCGCA    51000
GCTCGTGTCT TCCTGTGTGG ACTCCCTCTG GAGCGTGGCC CAGGCCCTGT TGGTGCTGTG    51060
CCCTGGGACT GGGCTCTCTA CCCTGTGTCC TGCCGAGTCC TGGCACCTGT CACCCCTGCT    51120
GTGTGTGGGG CTCTGGGCAC TGCGGCTGTG GGGCGCCCTA CGGCTGGGGG CTGTTATTCT    51180
CCGCTGGCGC TACCACGCCT TGCGTGGAGA GCTGTACCGG CCGGCCTGGG AGCCCCAGGA    51240
CTACGAGATG GTGGAGTTGT TCCTGCGCAG GCTGCGCCTC TGGATGGGCC TCAGCAAGGT    51300
CAAGGAGGTG GGTACGGCCC AGTGGGGGGG AGAGGGACAC GCCCTGGGCT CTGCCCAGGG    51360
TGCAGCCGGA CTGACTGAGC CCCTGTGCCG CCCCCAGTTC CGCCACAAAG TCCGCTTTGA    51420
AGGGATGGAG CCGCTGCCCT CTCGCTCCTC CAGGGGCTCC AAGGTATCCC CGGATGTGCC    51480
CCCACCCAGC GCTGGCTCCG ATGCCTCGCA CCCCTCCACC TCCTCCAGCC AGCTGGATGG    51540
GCTGAGCGTG AGCCTGGGCC GGCTGGGGAC AAGGTGTGAG CCTGAGCCCT CCCGCCTCCA    51600
AGCCGTGTTC GAGGCCCTGC TCACCCAGTT TGACCGACTC AACCAGGCCA CAGAGGACGT    51660
CTACCAGCTG GAGCAGCAGC TGCACAGCCT GCAAGGCCGC AGGAGCAGCC GGGCGCCCGC    51720
CGGATCTTCC CGTGGCCCAT CCCCGGGCCT GCGGCCAGCA CTGCCCAGCC GCCTTGCCCG    51780
GGCCAGTCGG GGTGTGGACC TGGCCACTGG CCCCAGCAGG ACACCCCTTC GGGCCAAGAA    51840
CAAGGTCCAC CCCAGCAGCA CTTAGTCCTC CTTCCTGGCG GGGGTGGGCC GTGGAGTCGG    51900
AGTGGACACC GCTCAGTATT ACTTTCTGCC GCTGTCAAGG CCGAGGGCCA GGCAGAATGG    51960
CTGCACGTAG GTTCCCCAGA GAGCAGGCAG GGGCATCTGT CTGTCTGTGG GCTTCAGCAC    52020
TTTAAAGAGG CTGTGTGGCC AACCAGGACC CAGGGTCCCC TCCCCAGCTC CCTTGGGAAG    52080
GACACAGCAG TATTGGACGG TTTCTAGCCT CTGAGATGCT AATTTATTTC CCCGAGTCCT    52140
```

```
CAGGTACAGC GGGCTGTGCC CGGCCCCACC CCCTGGGCAG ATGTCCCCCA CTGCTAAGGC    52200
TGCTGGCTTC AGGGAGGGTT AGCCTGCACC GCCGCCACCC TGCCCCTAAG TTATTACCTC    52260
TCCAGTTCCT ACCGTACTCC CTGCACCGTC TCACTGTGTG TCTCGTGTCA GTAATTTATA    52320
TGGTGTTAAA ATGTGTATAT TTTTGTATGT CACTATTTTC ACTAGGGCTG AGGGGCCTGC    52380
GCCCAGAGCT GGCCTCCCCC AACACCTGCT GCGCTTGGTA GGTGTGGTGG CGTTATGGCA    52440
GCCCGGCTGC TGCTTGGATG CGAGCTTGGC CTTGGGCCGC TGCTGGGGGC ACAGCTGTCT    52500
GCCAGGCACT CTCATCACCC CAGAGGCCTT GTCATCCTCC CTTGCCCCAG GCCAGGTAGC    52560
AAGAGAGCAG CGCCCAGGCC TGCTGGCATC AGGTCTGGGC AAGTAGCAGG ACTAGGCATG    52620
TCAGAGGACC CCAGGGTGGT TAGAGGAAAA GACTCCTCCT GGGGGCTGGC TCCCAGGGTG    52680
GAGGAAGGTG ACTGTGTGTG TGTGTGTGTG CGCGCGCGCA CGCGCGAGTG TGCTGTATGG    52740
CCCAGGCAGC CTCAAGGCCC TCGGAGCTGG CTGTGCCTGC TTCTGTGTAC CACTTCTGTG    52800
GGCATGGCCG CTTCTAGAGC CTCGACACCC CCCCAACCCC CGCACCAAGC AGACAAAGTC    52860
AATAAAAGAG CTGTCTGACT GCAATCTGTG CCTCTATGTC TGTGCACTGG GGTCAGGACT    52920
TTATTTATTT CACTGACAGG CAATACCGTC CAAGGCCAGT GCAGGAGGGA GGGCCCCGGC    52980
CTCACACAAA CTCGGTGAAG TCCTCCACCG AGGAGATGAG GCGCTTCCGC TGCCCACCT    53040
CATAGCCAGG TGTGGGCTCG GCTGGAGTCT GTGCAGGGGC TTTGCTATGG GACGGAGGGT    53100
GCACCAGAGG TAGGCTGGGG TTGGAGTAGG CGGCTTCCTC GCAGATCTGA AGGCAGAGGC    53160
GGCTTGGGCA GTAAGTCTGG GAGGCGTGGC AACCGCTCTG CCCACACACC CGCCCACAG    53220
CTTGGGCAGC CAGCACACCC CGCCTGAGGG AGCCCCATAT TCCCTACCCG CTGGCGGAGC    53280
GCTTGATGTG GCGGAGCGGG CAATCCACTT GGAGGGGTAG ATATCGGTGG GGTTGGAGCG    53340
GCTATGATGC ACCTGTGAGG CCATCTGGGG ACGTAGGCAG GGGGTGAGCT CACTATCAGG    53400
TGGCACCTGG GCCTGTCCCA CCAGCTCACG CCTGGACCCA CCCCACTCA CATTTGCGTG    53460
CAGGGCCATC TGGCGGGCCA CGAAGGGCAG GTTGCGGTCA GACACGATCT TGGCCACGCT    53520
GGTGTCCACA AGGCCCTCCA TGTCTGGGGA GACTTGGTGG TCACGCCAGG CCCAGGG       53577
```

```
GGTGTGAGGGGTAGGGGCAGGGTGGGAGGTGGGCTCCGCGGGTGGGCTGGG        50
GTCATGAAGGGCCTCAGGCGCTCTGCTATTGGGTTCCAAGGCTATCCTGA        100
GAACAGGGTGAGGGGATTGCCGTGGGGGGTTAAAGCCTTGTCATGTT           150
CGCTTTCGGGAGAGATAAAAACAACAGGTGGCCTTTATGGAGACGCTGCCCA      200
GAGCCAGGTCTGTGCCAGGCTCCTGTTGGGGTCGTCATGCGGAATCCTG         250
ACTCTGACCATCCGAGGCATAGGGACCGTGGAGATTTGCATTTCACAGAT        300
GAGGAAACAGGTTTGGAGAGGTGACACGACCTGTCCCAGGCATCACAGCC        350
GGGATGTGCATAGCAGGGTTTGGAACTATGAGGTGCCCAGGACCCAGGG         400
TTGGATTGAAAAGGGCGGAGGGACTAAGATAAGCAGACAGTTGTCCCCA         450
GCGCTGGGGGAGAGTCTCGCCCAGTCTGATGCCTTGTATTTCCCAGGCT         500
CCAGGCTCCTCGCCCAGGACACAGTGTCTCCTTGGGCTGCTGGATCCCTG        550
GGGGACGCTGGCACATCCCCAGGTTGCTAAACATTGGGGTGGTTCTGGCA        600
TTTGGTTTTGTAACGTTTCTGGGTCACTCCCGCCCTGTGCCACCCTTCCT        650
TAGGGGAGCCGTGTGTCCTTGGGGCTTTGCTGGTGGTCTCGAGGGTGGG         700
AGAAGAATGGGTTCTCCTGGACCAATGGAGCCCGTGCCCCTCGGGGCCAC        750
ATTGCTCCTGCGCTCCCTGACTGCGGACGCGTGTGTCTCGCGGCTGTCTC        800
TGTGGAGATGCCTCCTCCTGGCAACAGCACCCACAGAATTGCATC             850
AGACCCTACCCCACCCGTTGTTTGTGATGCTGTAGCTGAGGGCTC             894
```

```
Homologue  5' GGAAACAGGT TTGGAGAGGT GACACGACCT GTCCCAGGCA TCACAGCCAG
Authentic  5' GGAAACAGGT TTGGAGAGGT GACACGACCT GTC:::::::: ::::::::::

Homologue     GACAGGACCT GTCCAGGCAT CACAGCCCGGG ATGTGCATAG CAGGGGTTTG
Authentic     :::::::::: ::CCAGGCAT CACAGCCCGGG ATGTGCATAG CAGGGGTTTG Homologue     GAACTATGAG GTGCCCAGGA CCCAGGGTTG GATTGAAAAG GGCGCAGGGG ACTAAGATAA-3' (SEQ ID NO:18)
Authentic     GAACTATGAG GTGCCCAGGA CCCAGGGTTG GATTGAAAAG GGCGCAGGGG ACTAAGATAA-3' (SEQ ID NO:19)
```

FIGURE 3B

5'-AGGACCTGTCCAGGCATC*-3'  (SEQ ID NO:10)

FIGURE 6

```
3601 CGCCCGCGGCCGCTTCACTAGCTTCGACCAGGTGGCCGCAcgTGAGCTCCGCAGCCGTGGC     3660   (SEQ ID NO:20)
1201  R  P  R  R  F  T  S  F  D  D  Q  V  A  h  v  S  S  A  A  R  G   1220   (SEQ ID NO:21)
      :  :  :  :  :  :  :  :  :  :  :  :  :  X  X  :  :  :  :  :  :
      R  P  R  R  F  T  S  F  D  Q  :  :  V  A  Q  L  S  S  A  A  R  G          (SEQ ID NO:23)
      CGCCCCGCGGCCGCTTCACTAGCTTCGACCAGGTGGCCGCAGGTGAGCTCCGCAGCCGTGGC              (SEQ ID NO:22)

3697 GCTGCCCAGCAcgTACGCTTCGTGCGCCAGTGGTCCGTCTTTGGCAAGACATTATGCCGA      3756   (SEQ ID NO:24)
1233  A  A  Q  H  V  R  F  V  R  Q  W  S  V  F  G  K  T  L  C  R      1252   (SEQ ID NO:25)
      :  :  :  X  X  :  :  :  :  :  :  :  :  :  :  :  :  :  :  :
      A  A  Q  L  R  F  V  R  Q  W  S  V  F  G  K  T  L  C  R                   (SEQ ID NO:27)
      GCTGCCCAGCAGCTACGCTTCGTGCGCCAGTGGTCCGTCTTTGGCAAGACATTATGCCGA                (SEQ ID NO:26)

4540 CTGGCCACTGGCCCCAGCAGGACACCTTCGGGCCAAGAACAAGGTCCACCCCAGCAGCACTTAGTCCTCCTTCCTGGCGGG  4620   (SEQ ID NO:28)
1514  L  A  T  G  P  S  R  T  P  L  R  A  K  N  K  V  H  P  S  S  T                       1540   (SEQ ID NO:29)
      :  :  :  :  :  :  :  :  :  :  :  :  :  :  :  :  :  :  :  :  :
      L  A  T  G  P  S  R  T  P  L  R  A  K  N  K  V  H  P  S  S  T                              (SEQ ID NO:31)
      CTGGCCACTGGCCCCCAGCAGGACACCCTTCGGGCCAAGAACAAGGTCCACCCCAGCAGCACTTAGTCCTCCTTCCTGGCG           (SEQ ID NO:30)
```

FIGURE 8

|  |  | SEQ ID NO: |
|---|---|---|
| Exon 3: | ALTHGHSLLRDVSHNLERAIDVGLEANESAEAEE | 32 |
| LRG: | LHGLKALGHLDLSGNRLRKLPPGLEANFTLLRTL | 33 |
| GPIX: | PALPARTRHLLLANNSLQSVPPGALDHLPQLQTL | 34 |
| GPIa: | GQTLPALTVLDVSFNRLTSLPLGALRGLGELQEL | 35 |
| GPIb: | TAFPVDTTELVLTGNNLTALPPGLLDALPALRTA | 36 |
| Toll (LRR 8): | LEHQVNLLSLDLSNNALTHLPDSELAHTTNLTDL | 37 |
| SLIT (LRR 4): | IRHLRSLTRLDLSNNQITILSNYTLANLTKLSTL | 38 |
| Chaoptin: | FGNMPHLQWLDLSYNWIHELDFDALKNTKQLQLV | 39 |
| CONSENSUS: | --------LDLS-N-LT-LP-GLLA-L--L-TL | 40 |
|  |           I      AF |  |

|  |  |  |
|---|---|---|
| Exon 4: | GPQHLPLLPCRNLSGNLFEGDGGLAWLPRLAEE | 41 |
| LRG: | QPNWDMRDGFDISGNLWICDQNLSDLYRWLQA | 42 |
| TRKA: | TVQGLSLQELVLSGNELHLSLALRWLQRWEEE | 43 |
| GPIX: | FDHLPQLQTLDVTQNLWHCDCSLTYLRLWLED | 44 |
| GPIa: | FFGSHLLPFAFLHENLWLLNLEILYLRRLLQD | 45 |
| GPIb: | LDALPALRTAHLGANLWRLDLRLVPLRALLAG | 46 |
| Toll: | LNRTMKWRSVKLSGNLWMLDLGTAKPLLLLTQD | 47 |
| Slit (4): | FEDLKSLTHIALGSNLLYLDLGLKWLSDLIKL | 48 |
| CONSENSUS: | -------L----LSGNPW-CDC-L-WL-RW--- | 49 |

|  |  |  |
|---|---|---|
| EXON 8: | TATRLDLGDLSLAEVDAAGLALSLRYVLLGRLHLTA | 50 |
| EXON 19: | VLLYTWDLGLGLPVLTQSQLALNLLYASRLTYHLRL | 51 |
| EXON 21: | VALHLYDLGDLSLPGQDTDELRLAELSLLRLCDLRLVL | 52 |
| Pmel-17: | LSLYTWDLGLSLGTLISRALVVTLLYLELGPVTA | 53 |
| RPE-1: | LSLYTWDLGLSTGTLISRALTVTHLYLESLPVTA | 54 |
| CONSENSUS: | --YTWDFGDGS--L----P-A-HTYL-PG-Y-VQV | 55 |

Exon Trapping of the PKD1 Locus

SEQUENCE LISTING (1) GENERAL INFORMATION:

(iii) NUMBER OF SEQUENCES: 42

(2) INFORMATION FOR SEQ ID NO:1:

(i) SEQUENCE CHARACTERISTICS:
       (A) LENGTH: 53577 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:1:

```
TGTAAACTTT TTGAGACAGC ATCTCACCCT GTTCCCCAGG CTGGAGTGCA GTGGTGTGAT      60
CATGGCTCAC TGCAGCGTCA ACCTCCTGGG TCTACTTGAT CTGTAAACTT CGAGGGAAGG     120
TGTAATAAAC CCTCCTGCAA TGTCTTTGTT TTTCAAAATC TTTGTATTTC ACAGTTTAGC     180
TTCGTGGGTT GATGTTCTAT TTTGTTTTTG TGTGTGTGTG TGTGTGTTTT GTGTTTTTTT     240
TTGAGACACA GTCTTGCTCT TGTTGCCCAG GCTGGAGTGC AATGGTGTGA TCTTGGCTCA     300
CTGCAACTTC CACCTCTTGG GTTCAAGAGA TTCTCCTGCC TCAGCCTTCC GAGTAGCTAG     360
GATTACAGGC GCCGCCACCA CACCCCGCTA ATTTTGTATT TTTAGTAGAG ATGGGGTTTC     420
TCCATATTGG TCAGGCTGGT CTCAAACTCC CGACCTCAGG TGATCCGCCC ACCTCAGCCT     480
CCCAAAATGC TGGGATTACA GGCGTGAGTC ACCGCACCTG GCCAATGTTC TATTTTTGAG     540
AACACAACAG TTCATAATAT ATTCTACATA GACCATACCT GTTATGTGTA GATAAACAGA     600
CTCTTTTCCC ATTTAACACC TTTTGCCTTA GGTTTATTTT TCTGGTATCA ATACTGGCAC     660
ACTTACTTTG TTTGCAGTTT CCTGTCTTTT TTTTTTTTTT TTTTTTTTTT GAGACAGAGT     720
CTCACTCTGT CACCCAGGCT GGAGTGAAGT GGCGGGATCT CGGCTCACTG CAACCTCTAC     780
CTCCTGGGTT CATGCGATTC TCCTGCCTCA GCTTCCCGAA TAGCTGAGAC CACAACTGTG     840
TGCCACCATG CCCAGCCAAT TTTTGTATTT TTAGTAGACA CGGGGTTTCA CCATACTGGC     900
CAGGATGGCT CAATCTCTTG ACCTCGTGAT CCACCTGCCT CCGCCTCCCA AAGTGCTGGG     960
ATTACAGGCA TGAGCCACTG TGCCTGGCCT TTTTTTTTCT TTTTGAGATG GAGTCTCACT    1020
CTGTCACCCA GGCTGGAGTG CAGTGGGGTA ACCTCAGGTC ACTGCGACCT CCGCCTCCCG    1080
GGTTCCAGTG ATTCTCCTGC CTCAGCCTCC CGAGTAGCTG GGATTACAGG CACCCACCAC    1140
CATGCCTGGC TAATTTTTGT ATTTTTAGTA GAGACGGGGT TTTGCCACGT TGGCCAGGTT    1200
GGTCTCGAAC TCTTGGCCTC ATGTGACCCG CCTGCCTTGG CCTCCCAAAG TGCTGGGATT    1260
ACAGGTGTGA GCCACTGTGC CTGGCCTGGC TTTCTTGTTT CTTTTCTCCT CTTCTAGTTT    1320
CCCCCTTTTA GGCTAACAAT TATTCACTGT TAATAAAAAC CCTCAGGTCT GTATTTTATC    1380
AAGAAACATT TCCCTCACGT CTTCTTCCCT GAACCAAACA AGATCTCTGG CACATTTTAT    1440
TTGCTCTGTC TCACCACATG GATTTTGTTT TTTTGTTTCT TTGTTTTTTG AGATGGAGTC    1500
TCACTCTTGT TGCCCAGGCT GGAGTGCCAT GGCACAATCT CAGCTCACTG CAACCTCCAC    1560
CTCCTGGGTT CAAGCGATTC TCCTGTCTCA GCCTCCTGAG TAGCTGGGAT TACAGGCGCG    1620
TGGCACCACC CCCAGCTAAT TTTTGTATTT TTAGTAGAGA CGGGGTTTCA CCATGTTGGT    1680
CAGGCTGGTC TCGAACTCCT GACCTTGTGA TCTGCCCACC TTGGCCTCCC AAAGTGCTGG    1740
GATTACAGGC ATGAGCCACC ACGCCCGGCC CCCATGGTTT TTCAAATAGT TTAGAATTTC    1800
```

```
ATTTCCAGGT AACTAATTTG CTTCTTTAAA CATATGTCTT TTCTATTTAA GAAATCCTTT    1860

CTAAACAATT GCATTTTATT CCACAACCGC CTTCAAACAA TCATTGAGAC TTGGTTAATC    1920

TGTTTTGCTC ATTTGGCAGC AGTTTCTTGT GGCTGTTTCT TCCCTCCACT GGAGTCCTTG    1980

AATCTTAAGT CTGTCATTTG ACTGCAATTA AAAGCTGGGT TTGGAATACA ATCGCAGCCT    2040

TACCATCCAC CTGCTGTGTG ACCTGGTAAA TTTCTTTTTT TTTTTTTGAG ACGGAGTCTT    2100

GCTCTGTTGC CCAGGCTGGA GTGCAGTGGC ACAACCTCTG CCTCCCAGGT TCAAGCGATT    2160

CTACTGCCTC AGGCTCCCTA GTAGCTGGGA TTATAGGTGC CTGCCACCAT GCCCAGCTGA    2220

TTTTTGTATT TTTAGTAGAG ATGAGGTTTC ACCATGTTGG CTAGGCTGGT CTCGAACTTC    2280

TGATCTTGTG ATCTGCCCGC CTCGGCCTCC CAAAGTGCTG GGATTACAGG CATGAGCCAC    2340

CACTCCCAGC CAGTTCTTTT TTTCTTTTTT CCATTTTTTT TTTTTCGAG ACAGGATCTT    2400

ACTCTTTTGC CCAGGCGGGA GTGCAGTGGC ACAATCACGG CTCAGCGCAG CCACTGCCTA    2460

CTGGGCTCAC ACGCTCCTCC GGCCTCAGCC TCTCGAGTAC CTGGGACTAC AAGCGTGAGC    2520

CAGTTTGGCT AATTTTGGCT AATTTTTGTA GAAACGGGGT CTCGCCATGT TGGCCAGGCT    2580

GGTCTCCAAC TCCTGGACTC AAGGGATCCA CCTTCCTCCC CCTCTCAAAG TTCTGGGATT    2640

ACCGGAGTGA GCCACTGTGC CCTGCTGGCA AATTTCTTAA ACTGTCTGTG CCTCAGTGAC    2700

CTCATTTAAT AAAGGGAATA ATTGTAGCAC ACTTTTTCTA GAGCTGTGAA GATTCAATGG    2760

AATAAATAAG GCAATAAATG AATGGATGGG GAATGAAGGA TGTGGGTTTC CTCCCTCTTG    2820

TCTTTCAATA AGCTCTCACC ATCAACCTCC CATTGCCTGT TCTCTCTCTT CCCCCTCTCT    2880

CCCTCTGTCT CTCTCTCAGC CAGGAAACCT GGGGTAGGGA GGCTTGGAGC CAGCGGGTGC    2940

GTCGGGAGGC TGCGGGTACT GACTCGGGCC GCGCACGGAG ATCGCGGGAG AAGGATCCAC    3000

AACCGCGGAA GAAGGATCAG GGTGGAGCCT GTGGCTGCTG CAGGAGGAGG AACCCGCCGC    3060

CTGGCCCACA CCACAGGAGA AGGGCGGAGC AGATGGCACC CTGCCCACCG CTTCCCGCCC    3120

ACGCACTTTA GCCTGCAGCG GGGCGGAGCG TGAAAAATAG CTCGTGCTCC TCGGCCGACT    3180

CTGCAGTGCG ACGGCGGTGC TTCCAGACGC TCCGCCCCAC GTCGCATGCG CCCCGGGAAC    3240

GCGTGGGGCG GAGCTTCCGG AGGCCCCGCC CTGCTGCCGA CCCTGTGGAG CGGAGGGTGA    3300

AGCCTCCGGA TGCCAGTCCC TCATCGCTGG CCCGGTCGCG CTGTGGCGAA GGGGCGGAG    3360

CCTGCACCCG CCCCGCCCCC CCTCGCCCCG TCCGCCCCGC GCCGCGCGGG GAGGAGGAGG    3420

AGGAGCCGCG GCGGGCCCG CACTGCAGCG CCAGCGTCCG AGCGGCGGC CGAGCTCCCG    3480

GAGCGGCCTG GCCCCGAGCC CCGAGCGGGC GTCGCTCAGC AGCAGGTCGC GGCCGCAGCC    3540

CCATCCAGCC CGCGCCCGCC ATGCCGTCCG GGGCCCCGC CTGAGCTGCG GCCTCCGCGC    3600

GCGGGCGGGC CTGGGGACGG CGGGGCCATG CGCGCGCTGC CCTAACGATG CCGCCCGCCG    3660

CGCCCGCCCG CCTGGCGCTG GCCCTGGGCC TGGGCCTGTG GCTCGGGCG CTGGCGGGGG    3720

GCCCCGGGCG CGGCTGCGGG CCCTGCGAGC CCCCCTGCCT CTGCGGCCCA GCGCCCGGCG    3780

CCGCCTGCCG CGTCAACTGC TCGGGCCGCG GGCTGCGGAC GCTCGGTCCC GCGCTGCGCA    3840

TCCCCGCGGA CGCCACAGCG CTGTGAGTAG CGGGCCCAGC GGCACCCGGG AGAGGCCGCG    3900

GGACGGGCGG GCGTGGGCGG GTTCCCTGGC CCGGGACGGG AAGCAGGACG CGGGCCAGGA    3960

CGCTCCCAGG GGCGAGGCTC CGGCGCGGCA CGGCGGGCCC TGCTAAATAA GGAACGCCTG    4020

GAGCCGCGGT TGGCACGGCC CCGGGGAGCC GAAAACCCC GGGTCTGGAG ACAGACGTCC    4080

CACCCGGGGG CTCTGCAGAC GCCAGCGGGG GCGGGGCGCG GAGGCCGCGC TCAGCTGGGA    4140
```

```
GGACAAACAG TCGCTAATTG GAGAGGAATT GGGATCGGCC TGGGGCTGCG GGTACCCGG     4200

AGAGGTGGGG ATGGCTGTAG GGGGCGGCAG GGAAGAGTTC CAGGAGGTGT CTGGAAAAGG    4260

ATTTGATGGA TGTGCAAGAA TTGGGCTGAT GCTTAGGAAG GGGCGATGAG GTGGGTCCAG    4320

AAGAAGGGGG GTGAACGGTG TGAGCAAAGA CCGTGAGGCT GGAGGCTGGC CACGGGAGGT    4380

GTGAGGGGTA GGGGCAGGGT GGGAGGTGGG CTCGCGGGTG GGCTGGGGTC ATGAAGGGCC    4440

TCAGGCGCTC TGCTATTGGG TTCCAAGGCT ATCCTGAGAA CAGGGGTGAG GGGGGATTGC    4500

CGTGGGGGGT TAAAGCCTTG TCATGTTCGC TTTCGGAGA TAAAAACAAC AGGTGGCCTT     4560

TATGGAGACG CTGCCCAGAG CCAGGTCTGT GCCAGGCTCC TGTTGGGGGT CGTCATGCGG    4620

AATCCTGACT CTGACCATCC GAGGCATAGG GACCGTGGAG ATTTGCATTT CACAGATGAG    4680

GAAACAGGTT TGGAGAGGTG ACACGACCTG TCCCAGGCAT CACAGCCGGG ATGTGCATAG    4740

CAGGGGTTTG GAACTATGAG GTGCCCAGGA CCCAGGGTTG GATTGAAAAG GGCGGAGGGG    4800

ACTAAGATAA GCAGACAGTT GTCCCCAGCG CTGGGGAGAG TCTTGGGACC AGTCTGATGC    4860

CTTGTATTTC CCAGGCTCCA GGCTCCTCGC CGGGACAGTG TCTCCTTGGG TGCGTGCTGG    4920

ATCCCTGGGG GACGTGGCAC ATCCCCAGGC TTGCTAAACA TTGGGTGGGT TCTGGCATTT    4980

GGTTTTGTAA CGTTTCTGGG TCACTCCCGC CTGTGGCCAC CCTTCCTTAG GGGAGCCGTG    5040

TGTCCTTGGG GCTTTGCTGG GTGGTCTCGA GGGTGGGAGA GAATGGGTT CTCCTGGACC     5100

AATGGAGCCC GTGCCCCTCG GGGCCACATT GCTCCTGCGC TCCCTGACTG CGGACGCGTG    5160

TGTCTCGCGG CTGTCTCTGT GGAGATGGCC TCCTCCTGCC TGGCAACAGC ACCCACAGAA    5220

TTGCATCAGA CCTACCCCAC CCGTTGTTTG TGATGCTGTA GCTGAGGGCT CCTCTGTCTG    5280

CCAGGCCGGT CACTGGGGAC TCTGTCCAGG GCCTGGTGGT TCCTGCTTCC CAGCACCTGA    5340

TGGTGTCCAT GAGAGCAGCC CCTCAGGAGC TGTCCGGGAG AGAAGGGCGC TGGTGGCTGC    5400

TGAGCGGAGA GCAAGGCCCG TGTTCTCCAG GCCCTTGGCA CAGCAGTGGA GCCCCCGCCC    5460

CTGCCTTGTG TTGTCCTCTT AGGCTCTGGT CCTGGGGTTT GGAGGAGGGG GACCCTGGGA    5520

GTTGGTGGCC TGTCCCAGCC TGAGCTGGCA AGATTCCGAA TGCCAGGCCC CCAAGTGTG     5580

CAACAGGGCA CAGGGTGACC TCATGTGGGC AGGTGGGTGC TGTTCTGTAC ACACCTGGGG    5640

CCGCCGCTGG GAGAGTTCTG GAAGGTGGGG TGAGGGGACC CATGGCAAAC TAGGGCCTTA    5700

GGAAGGATGT GAAGGCCCTG GCTGGCCCCC CAGGCCACCC TCTGTGCTGT GGGGCAGCCC    5760

AGCCATTTTG CTGTCTACCC TGCAAACTCC TCCTCGGGGA GACGGCTGGG TTTTCCCCAG    5820

GGAAGAGGGG TCAAGCTGGG AGAGGTGAAG GACACAGATC ACAGCTGCTG GCAGGTGTTC    5880

AAGGGTCCAA GAGCGTTGCT GTCTGGGTGT CACCAGTAGC CTTCCTGGGG GGCTCACGCA    5940

GGTGCCTCTC CACTTGTGGC TCCCTGGCTG CTGAAGCTCA GCAGGGACAG CTGTGTCCAG    6000

TTCCAGGTGG AGGACAGCCG GGGCTTCTGA GGCCACAGCC TGCCTTGGGT TAATGATGCT    6060

GCCGAGAGGT GGTGGCTTTT GGAAAAGATG GCGTACTGCA AAACGTGCTG CTCTGCGTGG    6120

CTCGAAGCTT CGTGGGGAGA CGTGGGCAGA GCCGTGGCTG ACTCACAGAC CCCCCACCCC    6180

AGAGCCTGCC CTGCCCTCCC TGCCCCGACC CTTCTCCCTC CTGACCCATG TGTTTTTTTT    6240

TTTTTTTTTT TTTTTTGAGA CAGAGTTCAC TCTTGTTGCC AAGGCTGGAG TGCAATGGCA    6300

CGATCTCGGC TCATGGCAAC CTCCGCCTCC TGGGTTCAAG CGCTTTTTCC TGCCTCAGCC    6360

TCCCGAGTAG CTGGGATTAC AGGCGTGCAC CACCATGCCT GGCTAATTTT GTATTTTTAG    6420

TAGAGACAGG GTTTCTCCAT ATTGGTCAGG CTGGTCTTGA ACTCCTGACC TCAGATGATC    6480

CGCCCGCCTC GGCCTCCCAA AGTGCTGGGA TTACAGGCAT GAGCCACCAC GCCCAGCCCT    6540
```

```
GACCCATGTT TTGAACCAAA TTCCAGCCAC CCTTTTATCT GCAAGCATTT TGGAGGGCAT      6600

CGCAATACTG CAGACCCACC TAACACAACA GACAGTTCCT TCATGCCACC GAAGGCCTGG      6660

TGTGTTCACA TTTTTGGTTT AATAGTTTGA ATTAAGAGCC AAATAAGGTC CACACACTGC      6720

AATTAGTTGA TGTCTTTTTT TTTTTCTTTT TTTTTTTTTT TTTGAGACGG AGTCTTGCTC      6780

TTGTCTCCAG GCCGCAGTGC AGTGGCATGA TCTCAGCTCA CCGCAACCTC CGACTCCCTG      6840

GTTCAAGCGA TTCTCCTGCC TCAGCCTCCC GAGTACCTGG TAGCTGGGTT TACAGGCATG      6900

CACCACCGTG CCCAGCTAAT TTTTGTATTT TTAGTAGAGA CGGGGTTTTA CTGTGTTGGC      6960

CAGGATGGTC TCGATCTCCT GACCTCGTGA TCTGCCCACC TCGGCCTCCC AAAGTGCTGG      7020

GATTACAGGG GTGAGCCACC GCACCCGGCC AATGTCTTTT AAAAATATAT ACTTTTTTTT      7080

TTTTTTTGAG ACGGAGTTTC GCTCTTGTTG CCCAGGCTGG AGTGCAGTGG CGCGATCTCA      7140

CCTCACGGCA ACCTCCGCCT CCCGGGTTCA AGTGATTCTC CTGCCTCAGC CTCTCCAGTA      7200

GCTGGGATTA CAGGCATGTG CCACCATGCC TGGCTAATTT TGTATTTTTA GGAGAGACGG      7260

GGTTTCTCCA CGTTGGTCAG GCTGGTCTCA AACTCCTGAC CTCAGGTGAT CCGCCTGCCT      7320

TGGCCTCCCA AAGTGTTGGG ATTACAGGTG TGAGCCAACG CGCCCAGACA AAAATATATG      7380

TGTGTCTTTA AGGCTGGTCA AGCAAAGCAG TAGGACTGGA GAAAGAATGA AGAATTCTAC      7440

CTGGCTGTGA TCAATTCGTT GTGAACACCA CTGTGCTTGG ACCAGCTAGC TGATGTCTTT      7500

TGTTTTGTTT TGTTTGAGAC GGAGTCTGGC TCTGTCACCC AGGCTGGAGG ACAATGGTGT      7560

GATCTCGGCT CACTGCAGCC TCCATCTCCC GGGTTCAAGC GATTCTCCTG CCTCAGCCTC      7620

CTGAGTAGCT GGGATTAGAG GCGCGCGCCA CCACGCCCGG CTAATTTTTA AAAATATTTT      7680

TAGTAGAGAT GGGGTTTCAC CATGTTGGTC AGGCTGGTCT TGAACTCTTG GCCTTAGGTG      7740

ATCTGCTTGC CTCGGCCTCC CAAAGTGCTG GGATTACAGG TGTGAGTGAT GTATTTTATT      7800

TATTTATTTA TTTATTTATT TTTATTATTT GAGATGGAGT CTCACTCTGT TGCCCAGGCT      7860

GGAGTGCAGC AGTGCCATCT CAGCTCACTG CAAGCTCCGC CTCCTGGGTT CACGCCATTC      7920

TCCTGCCTCA GCCTCCTGAG TAGCCTGGAC TGGTGCCCGC CACCATGCCC AGCTAATTTT      7980

TTGTATTTTT AGTAGAGACG GGGTTTCACC GTGTTAGCCA GGATGGTCTG GATCTCCTGA      8040

CCTCGTGATC CTCCCGCCTC AGCCTCCCAA AGTGCTGGGA TTACAGGCTT GAGCCACCGC      8100

CTGTCTTTTA AATGTCCGAT GATGTCTAGG AGCTTCCCTT CCTCTCTTTT TCCTTGTGCA      8160

ATTTGTTGAA GAAACTGGCT CCTGCAGCCT GGATTTCTCG CTGTGTCTTG GGGGTGCCAC      8220

CTCCATGGTG TCACCTCCGT GGTGCTGTGA GTGTGTGCTT TGTGTTTCTT GTAAATTGGT      8280

CGTTGGAGCC GACATCCCAT TGTCCCAGAG GTTGTCCTGG CTGGCACTGG CCTAGGTGTA      8340

GATGTCATCA GCTCAGGGCC CCCTGCTCTA AAGGCCACTT CTGGTGCTGG TTGCCACTCA      8400

CCCTGGCTGG GGGTCACCTG GGTCTGCTGC TGTCTCGCAA ATGCTGGGGT CCAGGACTGG      8460

GCACATCGAG GGACTTGGTA GGTGCTTGGT TCACTGATGT AAAATATAGG AGCACCCGGG      8520

GCCTTGCCCT TTCCCACCTG CATCCCTGAA TGACAGGAGA GTGTGGGAGA GTGTAGGGAC      8580

AGCAGGCGCA GACCCCGGGG CCCCTGCCTG GGATTGGCGT CGGGGAAGAC AGGCATTCTG      8640

GAGCGACCCC TAGGCCTGAT GCCTTAGAGC GCAACTGCCA GAGACACAGC TTCCTTGGGG      8700

GGCTGGCCAG GCCACGGAGG GGCCCTGGCT CCCATTTCTG GTCCCTGGAT CCTGAGAGCG      8760

AGGACTAGGG ATTGTCACCA AGGCCTCCAT GAGCCCTCAG CAGAAGGAGG GCCACCCTCG      8820

AGGGCTCCGT TATCACTGGA GCCCGCGTTC AACCAACACG CAGATGATTC TCCAAGGACA      8880
```

```
GAGATGGATG ATGGGGAGGG GGCTGGCCTG GAAGGACCCC CAGTGCAGGT GACATTGAAG    8940

CCAGGTTTCA AAGCTCCCAC AGGGAGCTGC CCAGAGAGAG TCCCCAAGGG GCAAGGTGAC    9000

TCGGGGCAG  GGGTAGGGCC TCTGTCAGGA GAGCCTAGGA GAGGCCTGTG TCTTCTAGGA    9060

AGAGCCCTGG CAGCCGAGCG GAGGCAGTGG TGAGGACCTG CATCCTGCAT GTCCAGCTGG    9120

CCTCACCCGG GGTCCCTGAG CCGGGTCTTA CGTGGCTCCC GCACTCGGGC GTTCAGAACG    9180

TGCCTGCGTG AGAAACGGTA GTTTCTTTAT TAGACGCGGA TGCAAACTCG CCAAACTTGT    9240

GGACAAAAAT GTGGACAAGA AGTCACACGC TCACTCCTGT ACGCGATTGC CGGCAGGGGT    9300

GGGGGAAGGG ATGGGGAGGC TTTGGTTGTG TCTGCAGCAG TTGGGAATGT GGGGCACCCG    9360

AGCTCCCACT GCAGAGGCGA CTGTGGAGAC AGAGAGCACC TGCAGGTCAT CCATGCAGTA    9420

TCGGCTTGCA TCCAGATCAT ACAGGGAACA CTATGATTCA ACAACAGACA GGGACCCCGT    9480

TTAAACATGG ACAAGGGGTC ACTCACGCCT GGAATCCCAG CAGTTTGGGA GGCCAGGGTG    9540

GGTGGATCGC TTGAGCCCAG GAGTTTGACA CCAGCCTGGG CAACAGGGTG AGACCCCGGT    9600

CTCTAAAAAA TAAAAGAACA TTGGCCGGGC GTGGTGGTAT GCATCTGTGG TCCCAGCTAT    9660

TCAGGAGACT GAGGTGGGAC ATCACTTGAG CCGAGGAGGT CAAGGCTGCA GTGAGCTGTG    9720

ATCACACCAC TGCACTCCAG GCTGGGTCAC AGAGCAAGAC CCTGTCTCAA AAAAAAAAA    9780

AAAAAAAAAA AAAAATCACA GGATCTGAAC AGAGATTTCT CCAAAGAAGA CGCACAGATG    9840

GCCAACAGCG TGTGAGAAGA TGGTCGGCCT CATTAGTCAT GAGGGAAACG TAAATCAAAA    9900

CCACTGTCCA GCCGGGCGCG GTGCCTCACG CCTGTAATCC CAGCACTTTA GGAGAGCAGA    9960

TGGCTTGAGG CCAGGAGTTT GAGGCCAGCC TGGGCAACAT AGCGAGACCA ATAAATAGAT   10020

ATTAGTGGTG GCGCCTGTAG TCCCAGCTAG TTGGGAGGCT GAGGGGGGAG GATTCCCTGA   10080

GTCTATGAGG TTGAGACTGC AGTTAGCTGT GATGGTGCCA CTGCACTCCA GCCTGGGCGA   10140

CTAGGAAACG GTCTTTAAAA AAAAAAAAAA AAAACAGGGT GGGCGCGGTG GTTCACGCCT   10200

GTAATCTCAG CACTTTGGGA GGCCAAGGTG GGGGATCAC  AAGGTCAGGA GTTTGTGACC   10260

AGCCTGACCA ACATGGTGAA ACCCCGTTCT ACTAAAAATA CAAAAATTAG CGAGGTGTGG   10320

TCGTGGGCGC CTGTAATCCC AGCTAATTAG GAGGCTGAGG CAGGAGAATC ACTTGAACCC   10380

GGGAGGCGGA GGTTGCAGTG AGCCAATATC ACACCACTGC ACTCTAGCCT GGTCAACAGA   10440

GCGAGACTCT GTCTCAAAAA AAAAAAATGC TGAGCGTGGT GGCGCATGCC TGTAGTCTCA   10500

GCTACTTTGG GGGCTGAGGC AGGAGAATCG CTTGAACCTG GGAGGCAGAG GTCGCAGTGA   10560

GGCAAGATTG CACCATTGCA CTCCAGCCTG GGAGACAGAG TGAAACTCTG TCTCAAAAAG   10620

AAAAGGTCTA GGAAGAGTCC GCACCCTCTC CCCGCGGTGG CCACGCCGGG CTCCGCGCTG   10680

AGCCCTCTGT GTTCTTGTCT CTCCATACCT CATCACGGCA CCGCAGGGTT GCAGCCACTC   10740

CTGGTCTCAT TTTACACACC AGGAAATTGA GGCTCTTTGA GAAGCCGTGG TGATGATTTC   10800

ATCAGCATGC TCTGGGCAG  ACCCCTGCAG CCGCACAGGG TGCCTGGGGC CCACACTAGT   10860

GCCCTGGTTT ATAGACAGAC AGAGGTGGCA GTGGCGCTTC CGAGTCGGGC TGCGATGTGC   10920

TTGCACTCCC CGAGGGGCTG AGGGGCCCTG CGCCCAGGTG CAGCTGCTTG GGTGCTGCCA   10980

GCCCCTCCCA CCTCTCCCTC CCTGCCAGCC CCTCCCACCT CTCCCTCCCT GCCAGCCCCT   11040

CCCACCTCTC CCTCCCTGCC AGCCCCTCCC ACCTCTCCCT CCCTGCCAGC CCTCCCACC   11100

TCTCCCTCCC TGCCAGCCCC TCCCACCTCT CCCTCCCTGC CAGCCCCTCC CACCTCTCCC   11160

TCCCTGCCAG CCCCTCCCAC CTCTCCCTCC CTCCAGCCCC TCCCACCTCT CCCTCCCTGC   11220

CAGCCCCTCC CACCTCTCCC TCCCTGCCAG CCCCTCCCAC CTCTCCCTCC CTGCCAGCCC   11280
```

```
CTCCCACCTC TCCCTCCCTG CCAGCCCCTC CCACCTCTCC CTCCCTGCCA GCCCCTCCCA   11340

CCTCTCCCTC CCTGCCAGCC CCTCCCACCT CTCCCTCCCT GGCTCATCCC TGCTGTGTCC   11400

CTTCTCTCTA GTTTCCTGTT CAGTTTCAGG AAGGAGGCTG GGAACCCAGA TGTAGGGAAT   11460

TTGCGCCCTG GAGTCAGACC TGGGTTCACG TCCCAGCGCC TCCACCTCTG GTGTGACCTT   11520

GGTCCAGTCT CTCAGCCTCA GTTTCCTCAC CTGTAAAGTG GGCTCCATGA TTAGATGCAC   11580

CCTGCAGGGC AGTGTAGCAG TGACCTGGCT CAGCCACTGG CAGCCCCAAC AATCATACCT   11640

TGTTAAAGTA GCTCTGTCGG TTCCCTCAGG GGTTCCGGGG GCCCATTCCC CTGTCCTCCA   11700

TGCACTGTGA GACCTGCCCT GCCACAGAGC AGAGTGTAAC AGCCTGAGGG TGAGAGCCAG   11760

ACACTGTGCC TGTGCTTAGA CCAGACACTG GACGACGGGA GCCAGTGCAG CCTGGGCGGG   11820

TGGACTCCTA TGGACCCCTC AGCACCCAGC CTCGGTGCCT TCAGCGCAGG GCCGCGTGGC   11880

TGTGGGGGCT CACAAGACCC GGCCCACTCC TGCTTGTGCC TACATCTGGG TGTTTGCCCA   11940

TTGGTGCCTT TTGACGCGTT CTGGTGTGTG TGAGACGTGC GGGGCTGGGA AGTGTTGGCA   12000

GAGCCGCGAG TACCGTCCTC ACTCCTTTTG TTCTTTTGAC GTAAGCTGGC GAGTGGCACT   12060

GCCTGAGTTC CGCTCAGTGC CCGCCCTGAT GTGCGGACCC CGCTGCATTC TTGCTGTTAG   12120

GTGGTGGCGG TGTGCGCTGT CGCTGGTGGG CACCGAGAGT CTTTGGGAGC TTTGGGGAGG   12180

TTGTGCCAAG CCTGAGCCTC GACGTCCCCC TTCCCGGCTT TCTGTTGGCT CTTCTGAGGC   12240

CAGGGCATCT CTATGAGGGC CTCCTGCTGG AGCCGTCTCT GTGGATCTCC TCTGCCATCC   12300

TGGCCCATGA GTGGGTGATG CGCTGGCCAC CATCTGGTGA CAGTGGCCGG GCACCGCTGC   12360

CAAATGTGGG TCCCGCATCT GCAAGCCCCT CCCTGGGTCC CCTAGGGTAT GGGGTGGTTC   12420

TGCCACTGCC CTCGCTCCCC CACCTTGGGG TGCCTCTCCC CCTGCTCGTG GGGGAGACCC   12480

TGCCTGGGAT CTGCTTTCCA GCAAGGAATA TACTTTGGAG GGAGACACAC ATGTTCTTTT   12540

CTGGAGCTCT GCAGTGGCCA CGGCAGCCCA GCCCGCCAAG CACCCTGGAA TGAAAACATC   12600

CCGCTGCTGT CTGGGCCTGG CCTGCACTCT GCTGCCTGCG CTCCAGCTGG CTGAGGCCGG   12660

GCACGTCTGC GGGCACAGCA GCGGGGGCGC CACAGTCTCC CTGCAGAGTG AGCGCAGCTG   12720

GAAAATGCAG CTCACGCCCT TTCCCAGAAC ACCTCGCTCT TCATGGCTTG GCAGCTGTCC   12780

TTGCCTAGGG GCCAGGGTGC CCAGGCACTG GTGGCAGGAG AAGGGCTACA TCTGGGGCTG   12840

AGGCGGGCTG GGTCCTTTTC TCCCTGCAGC TCCCGAGGCC CAGCCCTGGC CCAGCCTGGC   12900

ATTCCTGACC TTAGCAGCGC CATGATCTGA AGACAGGCTG GCTTCTGTGA GGCCACCTCA   12960

GAAAGGGCTT TGTGCCCAGG CAGAGGCGGA AGCCAGCTCT TCCTTCTGGT TGAGGCAGGA   13020

ATGAGGCCAG CGCTGGGCAA GCCCATGCCC AGGGAACGTC ACAGCTGTGG GAGTACAGGG   13080

GCTCCGGGTT CTGAGCCCGT CCACTGTGCA TCGTGGCCCT GGCCTCAGGA TGGCTCGTAC   13140

CATCATTGGC TGTGCCCACA GCCGAGTGGG TGATGGGATT CCGGCTGCCC CGCTGGATCT   13200

GTGCTGCTGC CCTCTCCAGG GCACTGCTGT GCCCGCACAG CCGGGCGCAG ATGGCCAGTT   13260

TGCTTGCCCC CCCCCCCACC ATCCTCTTCC TACCTTGGCT TCCTCCATTG ACACACTGGA   13320

CCCTGCTGGC TGCCCGGGGA GGTGTTTGGG GGATGGTGTT GGGGGAGGAG GAGGGCCCCT   13380

TGAGCCTCAG TGTGCCCATC AGGAGCGTAA GGTCAGTGCA GCACCTGCCC ACACAGGCTG   13440

TGAAGGGTGG GAGTGGAGAG GGATGCAAGG GGGTCACAAC GCCTGGCTCC ATGTCAGCTG   13500

CGTGCAGGGG CACCAGGAGC CGGCCCTCAT TCTCCCCTTG AACTGGAAGG GTGGCCCCGA   13560

CCCCAGCGGC AGGTAGCATA CGTATGAAGC GCTCTCCTTC CTACACCCCA CAGGTGGGCT   13620
```

-continued

```
CGTCTCCAGA CGGCCCTTTT TGAGCTGGCT GTGTTTTTCC ATCTGTGTAG GCAAGGACAT    13680
CGCAGACTCC CCTTTCTCAT CTCCCTCGTT CAGCCTCCGA GGCCGGAGTC TCCATCCCTG    13740
TGCCTGCCTG TGGGTCCCGG GAGGACCTGA GGCTGCCCAT GTCACCCCCG GCATCTCATC    13800
CTGGGGACAG TTCAGCCGTG GGAGGGATCT GTAAGGACAG AATGCCGCTG AGCCTGGGGC    13860
TCCCCAGCTA GTCTCACACC CCGTGTCTGG GACCCAGAGA CCCTCGTGCA GGGCTCTGTT    13920
GCTTGGGGCC TGGCAGCCTC GTCCTGTATC AGAGGCTGCC ACCCCCACCC CTCGTGGGGC    13980
CAGGGTTGTG GCCGGCCTCC CTGGCCCTCC CCATGGAAGT GGTAGGCGGA GCCAGCAGCC    14040
ATCTGCCCAG CCCGGGGCTG CACTGTTTTT TTTCAAATGA GCACCGTCCC AAACTGCAGC    14100
CCGTTAATTT AAACAGGATC ATTTCCGGCC CTGGAAGCCG CCTCACTCTC CTTAAATAGA    14160
AAGGAGCACA GCGCAGAGGG AAACAGATGA GGTCATGGCT CGGCTGGCCC AGCGAGGAAG    14220
GGGCCGCAGT GGGGGTGGCA CTGCCGCCTG TCCCCTGTCC TCTCCAGCGC CCACACTGCA    14280
GCCCATTTCC TCACCCTGGG CCTGCTCTCG GGAGGGACGG GCCTGGGGGT CCTCTTGCTG    14340
GGCGGAGGGG AACCAGCTCC TCCAGGAGAG GACGGGCCT GGCAGGGGGC ATGGGCCTC    14400
CCTGGGTCTG GCGTCCTGTC CTGCCCCTGC CGAGGGAGGA GCGGTTACAT AAGCTCCGCA    14460
GGCGGCCCCT CCGAGCCGGT CCCCCCAGCC CAGTTTCCAG TGAGGCGGCC AGCGCGGGCG    14520
GGGGTGCCGG GCCTGGCGCA CACCCGCTGC TGACCACACG TGTCTGGAAT GTGCAGATGT    14580
TTCTTTGGGG GCTCCGTCCG GCCCCAGAC CCCACTCAGC ATCTGGTCTG GGGAGTGGGC    14640
GCCTGGGCA CTCAGCTCTG AGTGTGAGAC TCTGAGGCAG GTCTGGTTTG TCTGGGCCA    14700
TTCCCTCTGC TGTGGATTGG GAGGGCCCG GGAGCTGCCC CACACCCAGG GAAGTTCTCC    14760
TCAGTCCCAC TGTTGCATTC CCCGACCCCG GCTCCCCCGG CCCAGGAGCG CCTGTGGGGC    14820
AGAAGGCCCA GCCCCAAGAC TTCCCGGCCC TGCCAGCCTC AGGCTTCACC CACCCTCGCG    14880
CCAACTGTGG GCAGAGCCCA GGGGGAGGGC AGGAGAGCCA GCGCCTGGCT GGGAACACCC    14940
CTGAGGGGCC GAGGCTCCAG GGCGAGGGGG CCCGACCTGG GGTTCACACG CCCGGGTGGC    15000
GGGCAGACCC GCTGCAGCAT GAGACACGTG TCAGCTACCT CGGGCCGGCA GGCTGGCCCT    15060
GCTGCCCACA GCCCTGGGAC GTGGCCCCAC CTGTGACGGG TGTGGAGGGG CAGCCTCCAG    15120
GCCTGGCCAC ACCCTCTGCT GTTGCTGCTC CTGCTCCAGG ATTGGCAAGG GTGCTGGGAA    15180
GGGGTGAAGA CCCGTACTGT GGCCACACAC CTGGGACTTC CTTCTCCACC CAGTGGTGCC    15240
CCAGCAGCCG CTAAGGAGCC CGCTGGGTCC CACGCTAGGA TGGTCCTAAC TCCTCCCGCC    15300
TTCCAGATCG GACGCTCGGC GCTGGGGACC CCTTGTGTCC CGGGGCTGGG GCACCGTCCT    15360
GCCCCCATGG GGGTGTACTC CTCCCGACAA GCTTGGCTTC AGCTTCCCTG GGAGCACATC    15420
CTGGCCCTCG GGCACCCATC AGGCTGTCCC TGTGCACCTG GCTCCCACCC TTCCAGCTCA    15480
TAGCAGGAAC TGGGGTGAGG AGTGCGTGGG GCAGCAAGGG CCTGGGACCC CAGAGGACCC    15540
TGCACTCTGC TCTGTGCTCT TGCCTGGGCT TAGGGCCGCT CGGTGGTCCT GCTGCCAGAT    15600
GCCTGGGCCC TGCTGTGTCC CCCATCCTTG CAGGGAACCA GAACGTGGGG CAGGGCATC    15660
AGACAGCGGC GATGATGTCA CCTGGCGGGT GCAGAGGAAG CCCGAGGGGC GGGGTGGGGG    15720
GGCTGGCGCG AGGCTGCCTG GCTAGGCCTT GGCGTTCCCC CAGAACGGCG ATGGCAAAAG    15780
CAGATGGAGA CGTGAAAAAG TACGGGAGCA AGCGAGGTGA GGACTCCACG GGACCCCTG    15840
TGCTGTTCCC TGTCCCTGAA GCCCACACCT GAGTCCTGCC CAGGGCAGAT GCTTCCACAC    15900
CCAGGGGCA CCTGAGTCCT ACCCAGGGCA GACGCTTCCA CACCCTGGGG GCTGGGGAC    15960
TGCACCTGGC TCCTGTCTGG GCCCCAGCTT CATTCCACTG CCCTGGGCCC TGGGAGCTCG    16020
```

```
GCCGAGCGGG GTCCCCAAGA CCTTGCTGCA TTTCTGGGCC TTGGGCTGGG GTGAGGGCCG    16080

GGAGAAGGAG CCAGCCTGGA GCCTGGCACG CAGGGAGTGC ATGGCCAGAA CCGGTGACAG    16140

GCAGGGCTGC CTGCTGGCGT GGAAGAAGTG TCCATGGCAC CCCCAGGCCT GGTTCACAGT    16200

GGGATGGGCG GGGAGCCGGG GGGCTCTGGG GTCCTCGGCT GACCTGCCCC CACCCCTGCC    16260

CTGGCTTGTC AGCTCCCAGC AGCAGCCACT CTTGATGGAT TTTCCAGAAA ATGAGGTGTG    16320

GCCAAACATC TTCAGGCTTT TCCTTCTTTC CTTTCTCCCG TGGCCTGGGT GGGAGCTGCT    16380

CCCCATGCCT GGGGGCAGGT GCGAGAGCCT GTGCCCTCC CTGGGCAGT TTCACAGCTG     16440

TGTCCCTTCC AGGGGGCCTG CCTGTGTTCA CCGTGGCCTC TGCAGCACCT CTCGCCCCTT    16500

AGGGCTCCTG CGCCTCGGGT CCCGGTGCCT CATTTCTCCC TAAAGCATTG GTTCTGCTGC    16560

CGCCGCAGCC GCTGGAAAGT CCCTCCTCAG GTCTAACTGC AGTTCCTCAC GGCACAGTGT    16620

TCCCCCTCGG GCATGGTGCT TGGGCAGTGG GTGTGAGTCC AGCTGCCTCA CCCTGTCTCG    16680

AGAATGGCCT CTTGCTGGTC TCCCAGCCAC CACCCTGTCC CACCCCACGG CGGGGATGGT    16740

GTGGATGCCT AGCAGCGCGG CTGTGGGCCC ACCCATCCTT ATGGGCAGTG GGAGCACCT     16800

CAGCCCGTGT CCCTACCTTG GTGTAGAGGA GGGGACGGCA GAGAAGCAGG GTTCAGTTAG    16860

GGGGGAAGTG GTGGCCCTGC CGGAGGGGCC GTTCCCTGTG TGCCTGGCCC CCAGATCCTC    16920

TCCCCTCCCG GAGCCCAGGG CACAGGCATA GGCTCTCTGA GTGTCCCACA GCCCCTGGGG    16980

GAAGGGAACT GCACCCCCAA CCGTGCCCTC CATCCGCAGA TGGAACGAGA AGCTCCGGGA    17040

GCCAGTGCCC AGCGTCTCAT CTGTCTGGGC ACCCAGCCCA GGTGAGGGCC TGGCTCCACC    17100

GTCCGTGGCT GGTGCTGCTT CCTGGCACGG AGAAGGCCTC GGCTGCTCTG TCCCCTCAGC    17160

TGGGGTGGCC TCTGGTCCCC TTCTTTGTTG GTTCCCTTCT CAAGCTCTTG CCCTGGCCCC    17220

GGGCCCCACC GGGCAGCCTG TGTGTGCGTC TCTCCTGCGC CGGGTAGGCT CCTGTGGGAG    17280

CGGAGCTCCG GTGGGAGGAG CAGGGCTGGA GGCTGGCAGG GGCTGGGCGG GTGTTCAGGG    17340

ATGGAGGCCG CCCCGGCTTG GGGCTGGCTG CCGGGTGGTC ATTGCTGGGA AGAGCAAGTC    17400

TAGGCGGAGG CACCTGCTGG GTCACTCGTG GGGAGGGTGA CACCTGGGGA AGTAGAGGCC    17460

CGTGGCAGGA GGTGAGGCCT CGGGGTCCTG GGGAGCAGGG GGGTGGTGTG CAGACCTGCG    17520

GAGCCATAGT CCTGTGCCAG GAGCACTACT GGGAGTGCGT GGGACCAGGA GGGGTGCCCA    17580

GGGTGGGCGG CAGAGTGACC CCCGAGGTGC TTGAGGCCGA GGGGAGGTGG AGTTCTCGGT    17640

TTGCCCCAGC TCTCTGTCTA CTCACCTCCG CATCACCAGC TCCAGGACCT GGTTTGTAAC    17700

TCGGGCAGCT CTGAAAAGAG AGACATGCTG CCGCCCTGTG GTTTCTGTTG CTTTTTCTTC    17760

ACTGACTACT GACATGGGAT GTTTTTCCTA CGGCTGTGAC CAATTGTGCT TCTTCTAATT    17820

GCCTGGTTTT TCTTTTTTTG TTTTTGGAGT TTTCTCTTTC TTTCCTCCCT CCCTCTCACC    17880

CTCCATCCTT TTTTTTTTTA TTTTTATTTT TTGAGATGGA GCTTCACTCT TGCAGGATGG    17940

GGTGCTGGAG TGCAGGGGTG CGATCTCAGC TCACTGCAAC CTCTGCCTCG CGGGTTCAAG    18000

TGATTCTCCT GCCTAAGCCT CCTGAGTAGC TGGAATTACA GGTGCTTGCC ACCACGCCCG    18060

ACTAATTCTG TAGTTTTGGT AGAGACAGGG TGTCTCCGTG TTGGTCGGTC TGGTCTTGAA    18120

CTCCTGACCT CAGGTGATGC GCCCGCCTCA GCCTCCCAAA GTGCTGGGAT TACAGGCAGG    18180

AGCCATTGCA CCCGGCTCTT TCCCCTTCTC CTTTTCTTCT CTCTCTCCTC CCTTTCTTTC    18240

TTTTCTTTTC TTTTTTTTTT CTTTTGAGAT GGAGTCTCGC TCTGTCACCA GGCTGGATTG    18300

CAGTGGCGTG ATCTTGGCTC ACTGCAACCT TCGCCTCCCG GGTTCACGTG ATTCTCCTGC    18360
```

```
CTCAGCCTCC TGAGTGGCTG GCACTACAGG CTCCCGCCGC CATGCCCGGC TAATTTTTGC    18420

ATTTTTAGTA GAGACAGGGT TTCACCCTGT TGGCCAGGAT GGTCTCGATC TCTTGATCTC    18480

ATGATCCACC CACCTTGGCC TCCCAAAGTT CTGGCATTAC AGGAGTGAGC CACCGTGCCC    18540

GGCCATCTTT CTTTCCTTGC TTTCTCTTTG TTTTCTTTCG AGACCGGGTC TTGCTCTGTC    18600

GCCCAGGCTG GACTGCAGTG GCACAATCAT AGCTCACTGC AGCCTCGACT TCCCTGGCTC    18660

AAGCGATCCT TCCTCCTCAG CCCCCCGAGT AGCTGGAACT ACAGTTACAC ACTACCATGC    18720

CTGGCTGATT CTTTTTTTCC TTGTAGAGAT GGGGTCTTGC TATGCTGTCC ATCCTGGTCT    18780

CAAACTCCTG GCCTTCCCAA AGCACTGGGT TTACAGGCAT AAGCCACCAC ACCCAGTTTC    18840

CTTTTCTTCT TTTTAACTGG AATAGTTGAC GTTTTCTTTA TTAGCTGTGT GTCAGGAGGG    18900

TATTTTTGGC CTTTAGTATG TCGTGTAAGT TGCTAGTGCT TTTCTGAGAT TGTAGTTTGT    18960

TTTCTAATTT TATTTATATT TTGCGTAGAA GTTGTGTATT TTAGATGGAG TTAGGTCGGC    19020

TGGTCTTTGA TGTTTTATTT ATTAATTATG TATGTATTTA TTTATTTTTG AGGTAGAGTC    19080

TCGCCGTTTC ACCCAGGCTG GAGTACAGTG ATGCGATCTC AGCTCCCTGT AGCCTTGACC    19140

TCTCTGGGCT CAAGTGATTT TTCTCTCCTC TACCTCCCGA GTACTTGGGA CCCCAGGCGC    19200

ATGCCGCCAT GCCTGGCTAA TGTGTATTTT TTGTAGATAC GGGGTCTCAC TGTGTTGCCC    19260

AGGGTGGTTT CAAAATCCTG GCCCAGGCG ATCCTTCCGT CTCAGCTCCC ACGGTGCTGT    19320

GTTACCGGCG TGTGCCCAGT GCCTGGCCGT CTTGGAGGTC TTGTTTCTCT GGGTTTATGC    19380

CTCGAGGTGG CGCCTGCTCC CCTGTGCTCC CTGGTAGCCT GGTAGTGAGC CTGCTTCTCA    19440

CACAGTCATA CCTGGTTGTG GTCCCACAGT GGGACCACCC TGTTGGGTTC AGAACAGGAG    19500

ATGGGGCCC CTCGAGTCTG TGTGGGGCT GTGGACAGGG TTGGGAGACC TTGGCTCTGT    19560

GGGGGACTGT GGACAGGGGA TGGGGGGCCT TGGCCCTGCG TGGGATGGGT TGGGGGTCCG    19620

TGCCCTTCCT GGCCCTGGGT GGACAGGTCC ATGTGGCACT CGGCATAGGG CTGAGATGGG    19680

TGCAGAGGGC TGAGGCCCCC AGGCCTCTCC TGGCTTGGTT TCCCCAGATG AGTGTTCATT    19740

TGGGTCTTCC ATCAGAAAGT CCCCTCCTGA CCTCTGGGAG TGGGGAGCTC AAGGGTGGGA    19800

GGCCATAGCT TGGGGATGCT GGCAATGTGT GGGATGGGCC CAGGGAAGGC CTCTGGCCTA    19860

CTAGGGCTC TGGCCCTGAC CCACGGCCAC TCACTCCTCA GAGACGTCTC CCACAACCTG    19920

CTCCGGGCGC TGGACGTTGG GCTCCTGGCG AACCTCTCGG CGCTGGCAGA GCTGTGAGTG    19980

TCCCCCAGTC GTGCCAGCAT GCGGGGCTCA CTCCGGGTGG GCTGGCGGCA CCGCCTCTTG    20040

CTGCTCAGCT GTGGGGCTT CCATCAGCTT TGCCGAATCC CCCGTCTCTT CCAGGGATAT    20100

AAGCAACAAC AAGATTTCTA CGTTAGAAGA AGGAATATTT GCTAATTTAT TAATTTAAG    20160

TGAAATGTAA GTTGTGGTTC TTTGGGTGGG GTCCTGGCTG GACCCCAGGC CCCCAATATC    20220

CCTTCTGCCC TCCCAGTTGG TCCGTGTCCC CTTCCAGGCT TGAGACCAGA TCCTGGGGGC    20280

AGTTCACTGC CTGCTTGGAG CCCCCCAGTG CCGGCTTGGT TGGGGCAGGG GAGGCGGTGC    20340

TGTCAGGGTG GCTCCAGGGC CTGGTTGCCA GTGGGGGGCT GGCATAGACC CTTCCCACCA    20400

GACCTGGTCC CCAACACCTG CCCCTGCCCT GCAGAAACCT GAGTGGGAAC CCGTTTGAGT    20460

GTGACTGTGG CCTGGCGTGG CTGCCGCGAT GGGCGGAGGA GCAGCAGGTG CGGGTGGTGC    20520

AGCCCGAGGC AGCCACGTGT GCTGGGCCTG GCTCCCTGGC TGGCCAGCCT CTGCTTGGCA    20580

TCCCCTTGCT GGACAGTGGC TGTGGTGAGT GCCGGTGGGT GGGGCCAGCT CTGTCCTTCC    20640

CAGCCAGGTG GGACCTGGGC CCTGCAGACA CTGGGCAGGG CTCAGGAAGG CCTCTCTGGG    20700

GGGGGCCTCC GGGCCAAGGG AACAGCATGG GAGCCTGTGA GTGCGGCGGG CGGATGTGGG    20760
```

```
GGCGTGGGGT GGAGCCAGGA GGAGCAGAAC CCGGGGTCCA GTGGCTGCCT CTTCTAGGTG    20820

AGGAGTATGT CGCCTGCCTC CCTGACAACA GCTCAGGCAC CGTGGCAGCA GTGTCCTTTT    20880

CAGCTGCCCA CGAAGGCCTG CTTCAGCCAG AGGCCTGCAG CGCCTTCTGC TTCTCCACCG    20940

GCCAGGGCCT CGCAGCCCTC TCGGAGCAGG GCTGGTGCCT GTGTGGGGCG CCCAGCCCT     21000

CCAGTGCCTC CTTTGCCTGC CTGTCCCTCT GCTCCGGCCC CCGCCACCT CCTGCCCCCA    21060

CCTGTAGGGG CCCCACCCTC CTCCAGCACG TCTTCCCTGC CTCCCCAGGG GCCACCCTGG    21120

TGGGGCCCCA CGGACCTCTG GCCTCTGGCC AGCTAGCAGC CTTCCACATC GCTGCCCCGC    21180

TCCCTGTCAC TGCCACACGC TGGGACTTCG GAGACGGCTC CGCCGAGGTG GATGCCGCTG    21240

GGCCGGCTGC CTCGCATCGC TATGTGCTGC CTGGGCGCTA TCACGTGACG GCCGTGCTGG    21300

CCCTGGGGGC CGGCTCAGCC CTGCTGGGGA CAGACGTGCA GGTGGAAGCG GCACCTGCCG    21360

CCCTGGAGCT CGTGTGCCCG TCCTCGGTGC AGAGTGACGA GAGCCTCGAC CTCAGCATCC    21420

AGAACCGCGG TGGTTCAGGC CTGGAGGCCG CCTACAGCAT CGTGGCCCTG GGCGAGGAGC    21480

CGGCCCGAGG TGAGTGTCTG CTGCCCACTC CCCTTCCTCC CCAGGGCCAT CCAGATGGGG    21540

CAGAGCCTGG TACCCCCGTC TTGGGCCCAC ACTGACCGTT GACACCCTCG TTCCCACCGG    21600

TCTCCAGCGG TGCACCCGCT CTGCCCCTCG GACACGGAGA TCTTCCCTGG CAACGGGCAC    21660

TGCTACCGCC TGGTGGTGGA GAAGGCGGCC TGGCTGCAGG CGCAGGAGCA GTGTCAGGCC    21720

TGGGCCGGGG CCGCCCTGGC AATGGTGGAC AGTCCCGCCG TGCAGCGCTT CCTGGTCTCC    21780

CGGGTCACCA GGTGCCTGCC CCCACCCCCC GAGGGGCCAT AGGTTGGGAG ATCTCTGAAG    21840

CACTGGGGCA GAGACTGCGG CTGGGGAGTC TCAGGAGGAA GGAGGTGGGA GCTGGGCCGG    21900

CCCTGGTGAG CAGGTGGCGC CGGCCGGTGG GGCCGTTCCT GTCAGCTCTG CAGATGCAGA    21960

GGTGGACATG AGCTGGGGGC AGCCTCCGGA CACTCCTGGG CACGCCATAC GGGAGGTGGC    22020

CTGCACGGGA TCCCTGCCCG GTACCCACAG GCCCCGTGGG TGGGTGCTGC TGTGAGCCTG    22080

GGCTGGTGGG CCCTGGTCTC CGGGCTCTGA GCCTCAGTTT CCCCATCTGG AAAGGGGAC    22140

AGTGATGGGG CTCCCAGCGG GCTGCTGTGA GGGTGGGAGG ATGGAGGAGT GCCCTGAGCC    22200

CCCTGCCATC CCACACCCGC CCCCAGGAGC CTAGACGTGT GGATCGGCTT CTCGACTGTG    22260

CAGGGGGTGG AGGTGGGCCC AGCGCCGCAG GGCGAGGCCT TCAGCCTGGA GAGCTGCCAG    22320

AACTGGCTGC CCGGGGAGCC ACACCCAGCC ACAGCCGAGC ACTGCGTCCG GCTCGGGCCC    22380

ACCGGGTGGT GTAACACCGA CCTGTGCTCA GCGCCGCACA GCTACGTCTG CGAGCTGCAG    22440

CCCGGAGGTG TGCGGGGGGC CAGGCAGGGG CCTGAGACGC TGGCTGTGGT TAGGGGCCTG    22500

CCGAGCGCCC GCGGTGGAGC CTGGGCTGAG GAGGAGGGGC TGGTGGGGGG GTTTTCGGGC    22560

GGCTCGGTCC CCAGTCTGTT CGTCCTGGTG TCCTGGGCCC TGGCCCGGCG CCTCACTGTG    22620

CACTCGCCAC CCCAGGCCCA GTGCAGGATG CCGAGAACCT CCTCGTGGGA GCGCCCAGTG    22680

GGGACCTGCA GGGACCCCTG ACGCCTCTGG CACAGCAGGA CGGCCTCTCA GCCCCGCACG    22740

AGCCCGTGGA GGTAGTCGGC CCCCCACGTT CTACAACCTG CCCTCCTGCC TGCCCCTGGA    22800

GGCCTTGCCT GCCCTGCCCA CTGTGGGTCT CGCCAAAAAA CTTGGGGGCC TTAATGTTGC    22860

TTGTGCCCAG TGAAGATGGT TGGGAAAATC CAGAGTGCAG AGAGGAAAGC GTTTACTCAC    22920

ATTACCTCCA GGCCTTTTCT CTGAGCGTGT GTGAGTTATT CCTGAAAGGC AGGTCAGGGG    22980

TCCTGCCCCC CATGGACAGT TTCCACCGGA GTCTTCCTCT CGAGCGACAG GAGCCAGGCC    23040

TGTGGGGGTC TGATGGCTCG CTCTCCTTCC CTCCCCTCTT CCTGGGAAGT TCGGGTAGGG    23100
```

```
GGAGTCTGGG CTTCAGGCTG GGATGGGGTC TGTGGAGCTG AGGCGGCCCC CTGCCCACCA    23160

GGTCATGGTA TTCCCGGGCC TGCGTCTGAG CCGTGAAGCC TTCCTCACCA CGGCCGAATT    23220

TGGGACCCAG GAGCTCCGGC GGCCCGCCCA GCTGCGGCTG CAGGTGTACC GGCTCCTCAG    23280

CACAGCAGGT GGGACTCTGG GTGGTGGGTG GTGGGTGGTG GGCGCCGCAG GACTCGGGGT    23340

GGCCTCTCTG AGCTTTCACG TCTGCTGGTC CTGTGGCCAC CAGAGTGGTT CCCAGTCTTA    23400

GGTGGACAGA GCAGGGGTTC CAGAGACACC AGCTCATTCC AGGTGTCCTG GGGGTGGATT    23460

GGGTGGGGCC TGCCTGGGGG CCGGCCTGGG TCAGTCGGCT GGCCGGAGAC GGACGCAGCA    23520

CTGGGCTGGG AGTGCTGCCC AGGTGGGGAG ACCTGTCCTC ACAGCAAGGC CAGGATTGCT    23580

GGTGCAGGCA GTTGGGCATC TCTGACGGTG GCCTGTGGGC AAATCAGGGC CCAACACCC     23640

TCCCCTCCTC ACAGGGACCC CGGAGAACGG CAGCGAGCCT GAGAGCAGGT CCCCGGACAA    23700

CAGGACCCAG CTGGCCCCCG CGTGCATGCC AGGGGACGC TGGTGCCCTG GAGCCAACAT     23760

CTGCTTGCCG CTGGACGCCT CCTGCCACCC CCAGGCCTGC GCCAATGGCT GCACGTCAGG    23820

GCCAGGGCTA CCCGGGGCCC CCTATGCGCT ATGGAGAGAG TTCCTCTTCT CCGTTCCCGC    23880

GGGGCCCCCC GCGCAGTACT CGGTGTGTGG CCCTGACCTG GGTCTGTTCC CTGCATCTCC    23940

TCAGGCCACC TTCCTGTCTG CTGCCCAGGG TCTGGGTCTG TGCACCAGAC ACACCCAGCC    24000

TGCAGGCCCC TCCCACGTCC TTGCCACCTC TGACCTCCGA CCTCTGCAGT GCCCTCGGCC    24060

CTCTCCCAGT GGGAGAAGCT CTCGCCTGGG CCCTTGGCAC GAGCTGTGCC TCCTCTTCCT    24120

CTCTCCCAGC ACAGCTGCTC CTTCCTGTCT GCCAGGTCTT GGCCTGTGTC CTCTCCCCGT    24180

GTGTCCCCCG GTCTGCAACT GTCCTGCCTG TCCTTGTCAC GAGCACTGTG GGGAGGCTCC    24240

TTGAGGTGTG GCTGACGAAG CGGGGAGCCC TGCGTGTCCA CCCTCATCCG TCGTGCGGGG    24300

GTCCACGGGC CATGACCGTG AGGACGTGAT GCAGCCCTGC CTCCCTCTCC ACAGGTCACC    24360

CTCCACGGCC AGGATGTCCT CATGCTCCCT GGTGACCTCG TTGGCTTGCA GCACGACGCT    24420

GGCCCTGGCG CCCTCCTGCA CTGCTCGCCG GCTCCCGGCC ACCCTGGTCC CCGGGCCCCG    24480

TACCTCTCCG CCAACGCCTC GTCATGGCTG CCCCACTTGC CAGCCCAGCT GGAGGGCACT    24540

TGGGCCTGCC CTGCCTGTGC CCTGCGGCTG CTTGCAGCCA CGGAACAGCT CACCGTGCTG    24600

CTGGGCTTGA GGCCCAACCC TGGACTGCGG CTGCCTGGGC GCTATGAGGT CCGGGCAGAG    24660

GTGGGCAATG GCGTGTCCAG GCACAACCTC TCCTGCAGCT TTGACGTGGT CTCCCCAGTG    24720

GCTGGGCTGC GGGTCATCTA CCCTGCCCCC CGCGACGGCC GCCTCTACGT GCCCACCAAC    24780

GGCTCAGCCT TGGTGCTCCA GGTGGACTCT GGTGCCAACG CCACGGCCAC GGCTCGCTGG    24840

CCTGGGGGCA GTGTCAGCGC CCGCTTTGAG AATGTCTGCC CTGCCCTGGT GGCCACCTTC    24900

GTGCCCGGCT GCCCCTGGGA GACCAACGAT ACCCTGTTCT CAGTGGTAGC ACTGCCGTGG    24960

CTCAGTGAGG GGGAGCACGT GGTGGACGTG GTGGTGGAAA ACAGCGCCAG CCGGGCCAAC    25020

CTCAGCCTGC GGGTGACGGC GGAGGAGCCC ATCGTGGCC TCCGCGCCAC GCCCAGCCCC     25080

GAGGCCCGTG TACTGCAGGG AGTCCTAGTG GTGAGTATGG CCGAGGCTCC ACCACCAGCC    25140

CCCAGGCAGG TGCCTGCAGA CAGGGTGCTC ACACAGGGCG TGAGGCCTGG CTTCCCAGTG    25200

AGGGCAGCAG CCCAGTTACT GGGGACGTCG GCCCCGGGCA GGTCCTGCTG GCTGGCTCCT    25260

CGGGCTACCT GGTGGGCTTT AAATTCCTGG AAAGTCACGG CTCTGACAGT GGCTCCGCTA    25320

ACTCATTCCA CTGTCTCATT TCACAAAATG AATTTAAAAC TCTGCTCCCT GACCTCACAC    25380

GAGCCCCGT GAGTCTCTCA CGCCCTCTGC TGTGTTCTCG CCTGGCTAAA GCGAGTGGCT     25440

TTTGAGGTGG AGTCTGAACC CCTGATGGGA AACTGCGGGC TGCCCGCGGT GCCACCATGC    25500
```

```
TGGGTACATG GGGGACAGGG CTGTCTCCAT CTTGCGGGTA CCTGCCTCTT CACCAGGGGC    25560

CTTGGGAGGG GCCATCAGAA ATGGCGTGAC CTGTGCAGCC TGTCCTGGGT TCTGTAAGCC    25620

AGTGTAGGTG CCTCCCCTCA CTGCTCCGAG CTCTCTGGGT GAGGAGCTGG GGCAAGAGCG    25680

CCGGGAGGGT CTGAGAAGAC TCAGAGAGAG GTGGACTCTT TGTAGCTGGT ACTAGGTTTG    25740

CTTTACAGAT GGGGAAACTG AGGCACAGAG AGGTTGAGGC ATTAGTAGTA CTACATGGCT    25800

GGCTGGAGAG CCGGACAGTG AGTGTCCCAG CCCGGGCTTG GCTCCCATGG CATGCAGAGC    25860

CCCGGGCACC TCCTCTCCTC TGTGCCCCGC GTGGGACTCT CCAGCCCGAC GGGAGGTGTG    25920

TCCAGGAGGC GACAGGCTAA GGGCAGAGTC CTCCACAGAG CCCAGGCTGA CACCATTCCC    25980

CCCGCAGAGG TACAGCCCCG TGGTGGAGGC CGGCTCGGAC ATGGTCTTCC GGTGGACCAT    26040

CAACGACAAG CAGTCCCTGA CCTTCCAGAA CGTGGTCTTC AATGTCATTT ATCAGAGCGC    26100

GGCGGTCTTC AAGCTCTCAG TAGGTGGGCG GGGGTGGGGA GGGGAGGGGA TGGGGCGGGG    26160

CAGGGCGGGG GCGGGCTCCA CCTTCACCTC TGCCTTCTGC TCTGCTTCAT GCTGCCCGAG    26220

GACGCTGCCA TGGCTGTGGG TGAGTGGAGG GAGGGACGCC AATCAGGGCC AGGCCTCTCA    26280

CCTGCCACCT GGGCTCACTG ACGCCTGTCC CTGCAGCTGA CGGCCTCCAA CCACGTGAGC    26340

AACGTCACCG TGAACTACAA CGTAACCGTG GAGCGGATGA ACAGGATGCA GGGTCTGCAG    26400

GTCTCCACAG TGCCGGCCGT GCTGTCCCCC AATGCCACGC TAGCACTGAC GGCGGGCGTG    26460

CTGGTGGACT CGGCCGTGGA GGTGGCCTTC CTGTGAGTGA CTCGGGGCC GGTTTGGGGT    26520

GGGCACCAGG CTCTTGTCCC AGCCCCAGCC TCAGCCGAGG GACCCCCACA TCACGGGGTT    26580

GCTTTTCTGA GCCTCGGTTT CCCTGTCTGT TGGGAGGTAA CTGGGTGCAC AGGAGCCCTG    26640

AGGCTGCACG GGAGCCGGGA GAGGCCTCAG CACAGCCGGG TGGGCCCTGA ATGGAGGCCC    26700

GGGGCGTGAC TGCAGAGTGG AGCCTCGGCT GGGTCCCAAG CACCCCCTGC CCGCCACCG    26760

CCCACCCCTG TCCCGGTTCA CTCACTGCGT CCCACCGCCC CGGCAGGTGG ACCTTTGGGG    26820

ATGGGGAGCA GGCCCTCCAC CAGTTCCAGC CTCCGTACAA CGAGTCCTTC CCGGTTCCAG    26880

ACCCCTCGGT GGCCCAGGTG CTGGTGGAGC ACAATGTCAT GCACACCTAC GCTGCCCCAG    26940

GTGAGGGATG AGGGGGTGAG GGGGCCACTG CCTTTCAGGC TCTGAGCACG GGTCCCCCCA    27000

GCTCCCCAGT CAAGCTGCCC CCCTTCCTCC CAACAGCCC TCACTGTGAC CTCACCTGGG    27060

CTGATGGCTT AGGCCCTACT GGGGTGAGGG AGGGGCCAGG CGTGGGGGGA GTGGACAGGG    27120

AAGCTGGGCC CCTGAACTGC GCCCCCCGCC CTCCCCGGGC CTGGCTCTTG CTGCTCTGCT    27180

GCCCCGAGTG CAGCTGCACT TGGAGGCGGT GCGTCCTCGC CAGGCAGCCC TCAGTGCTGC    27240

TACACCTGTG CTCCGTCCCG CACGTGGCTT GGGAGCCTGG GACCCTTAAG GCTGGGCCGC    27300

AGGTGCAGCC GTTCACCCCG GGCTCCTCAG GCGGGGGGCT TCTGCCGAGC GGGTGGGGAG    27360

CAGGTGGGGG TGCCGCGGCT GCCCCACTCG GGCCTGTCCC CACAGGTGAG TACCTCCTGA    27420

CCGTGCTGGC ATCTAATGCC TTCGAGAACC GGACGCAGCA GGTGCCTGTG AGCGTGCGCG    27480

CCTCCCTGCC CTCCGTGGCT GTGGGTGTGA GTGACGGCGT CCTGGTGGCC GGCCGGCCCG    27540

TCACCTTCTA CCCGCACCCG CTGCCCTCGC CTGGGGTGT TCTTTACACG TGGGACTTCG    27600

GGGACGGCTC CCCTGTCCTG ACCCAGAGCC AGCCGGCTGC CAACCACACC TATGCCTCGA    27660

GGGGCACCTA CCACGTGCGC CTGGAGGTCA ACAACACGGT GAGCGGTGCG GCGGCCCAGG    27720

CGGATGTGCG CGTCTTTGAG GAGCTCCGCG GACTCAGCGT GGACATGAGC CTGGCCGTGG    27780

AGCAGGGCGC CCCCGTGGTG GTCAGCGCCG CGGTGCAGAC GGGCGACAAC ATCACGTGGA    27840
```

```
CCTTCGACAT GGGGGACGGC ACCGTGCTGT CGGGCCCGGA GGCAACAGTG GAGCATGTGT   27900
ACCTGCGGGC ACAGAACTGC ACAGTGACCG TGGGTGCGGC CAGCCCCGCC GGCCACCTGG   27960
CCCGGAGCCT GCACGTGCTG GTCTTCGTCC TGGAGGTGCT GCGCGTTGAA CCCGCCGCCT   28020
GCATCCCCAC GCAGCCTGAC GCGCGGCTCA CGGCCTACGT CACCGGGAAC CCGGCCCACT   28080
ACCTCTTCGA CTGGACCTTC GGGGATGGCT CCTCCAACAC GACCGTGCGG GGGTGCCCGA   28140
CGGTGACACA CAACTTCACG CGGAGCGGCA CGTTCCCCCT GGCGCTGGTG CTGTCCAGCC   28200
GCGTGAACAG GGCGCATTAC TTCACCAGCA TCTGCGTGGA GCCAGAGGTG GGCAACGTCA   28260
CCCTGCAGCC AGAGAGGCAG TTTGTGCAGC TCGGGGACGA GGCCTGGCTG GTGGCATGTG   28320
CCTGGCCCCC GTTCCCCTAC CGCTACACCT GGGACTTTGG CACCGAGGAA GCCGCCCCCA   28380
CCCGTGCCAG GGGCCCTGAG GTGACGTTCA TCTACCGAGA CCCAGGCTCC TATCTTGTGA   28440
CAGTCACCGC GTCCAACAAC ATCTCTGCTG CCAATGACTC AGCCCTGGTG GAGGTGCAGG   28500
AGCCCGTGCT GGTCACCAGC ATCAAGGTCA ATGGCTCCCT TGGGCTGGAG CTGCAGCAGC   28560
CGTACCTGTT CTCTGCTGTG GGCCGTGGGC GCCCCGCCAG CTACCTGTGG GATCTGGGGG   28620
ACGGTGGGTG GCTCGAGGGT CCGGAGGTCA CCCACGCTTA CAACAGCACA GGTGACTTCA   28680
CCGTTAGGTG GCCGGCTGGA ATGAGGTGAG CCGCAGCGAG GCCTGGCTCA ATGTGACGGT   28740
GAAGCGGCGC GTGCGGGGGC TCGTCGTCAA TGCAAGCCCC ACGGTGGTGC CCCTGAATGG   28800
GAGCGTGAGC TTCAGCACGT CGCTGGAGGC CGGCAGTGAT GTGCGCTATT CCTGGGTGCT   28860
CTGTGACCGC TGCACGCCCA TCCCTGGGGG TCCTACCATC TCTTACACCT TCCGCTCCGT   28920
GGGCACCTTC AATATCATCG TCACGGCTGA GAACGAGGTG GGCTCCGCCC AGGACAGCAT   28980
CTTCGTCTAT GTCCTGCAGC TCATAGAGGG GCTGCAGGTG GTGGGCGGTG GCCGCTACTT   29040
CCCCACCAAC CACACGGTAC AGCTGCAGGC CGTGGTTAGG GATGGCACCA ACGTCTCCTA   29100
CAGCTGGACT GCCTGGAGGG ACAGGGGCCC GGCCCTGGCC GGCAGCGGCA AAGGCTTCTC   29160
GCTCACCGTC TCGAGGCCGG CACCTACCAT GTGCAGCTGC GGGCCACCAA CATGCTGGGC   29220
AGCGCCTGGG CCGACTGCAC CATGGACTTC GTGGAGCCTG TGGGGTGGCT GATGGTGGCC   29280
GCCTCCCCGA ACCCAGCTGC CGTCAACAAA AGCGTCACCC TCAGTGCCGA GCTGGCTGGT   29340
GGCAGTGGTG TCGTATACAC TTGGTCCTTG GAGGAGGGGC TGAGCTGGGA GACCTCCGAG   29400
CCATTTACCA CCCATAGCTT CCCCACACCC GGCCTGCACT TGGTCACCAT GACGGCAGGG   29460
AACCCGCTGG GCTCAGCCAA CGCCACCGTG GAAGTGGATG TGCAGGTGCC TGTGAGTGGC   29520
CTCAGCATCA GGGCCAGCGA GCCCGGAGGC AGCTTCGTGG CGGCCGGGTC CTCTGTGCCC   29580
TTTTGGGGGC AGCTGGCCAC GGGCACCAAT GTGAGCTGGT GCTGGGCTGT GCCCGGCGGC   29640
AGCAGCAAGC GTGGCCCTCA TGTCACCATG GTCTTCCCGG ATGCTGGCAC CTTCTCCATC   29700
CGGCTCAATG CCTCCAACGC AGTCAGCTGG GTCTCAGCCA CGTACAACCT CACGGCGGAG   29760
GAGCCCATCG TGGGCCTGGT GCTGTGGGCC AGCAGCAAGG TGGTGGCGCC CGGGCAGCTG   29820
GTCCATTTTC AGATCCTGCT GGCTGCCGGC TCAGCTGTCA CCTTCCGCCT GCAGGTCGGC   29880
GGGGCCAACC CCGAGGTGCT CCCCGGGCCC CGTTTCTCCC ACAGCTTCCC CCGCGTCGGA   29940
GACCACGTGG TGAGCGTGCG GGGCAAAAAC CACGTGAGCT GGGCCCAGGC GCAGGTGCGC   30000
ATCGTGGTGC TGGAGGCCGT GAGTGGGCTG CAGGTGCCCA ACTGCTGCGA GCCTGGCATC   30060
GCCACGGGCA CTGAGAGGAA CTTCACAGCC CGCGTGCAGC GCGGCTCTCG GGTCGCCTAC   30120
GCCTGGTACT TCTCGCTGCA GAAGGTCCAG GGCGACTCGC TGGTCATCCT GTCGGGCCGC   30180
GACGTCACCT ACACGCCCGT GGCCGCGGGG CTGTTGGAGA TCCAGGTGCG CGCCTTCAAC   30240
```

```
GCCCTGGGCA GTGAGAACCG CACGCTGGTG CTGGAGGTTC AGGACGCCGT CCAGTATGTG   30300

GCCCTGCAGA GCGGCCCCTG CTTCACCAAC CGCTCGGCGC AGTTTGAGGC CGCCACCAGC   30360

CCCAGCCCCC GGCGTGTGGC CTACCACTGG GACTTTGGGG ATGGGTCGCC AGGGCAGGAC   30420

ACAGATGAGC CCAGGGCCGA GCACTCCTAC CTGAGGCCTG GGGACTACCG CGTGCAGGTG   30480

AACGCCTCCA ACCTGGTGAG CTTCTTCGTG GCGCAGGCCA CGGTGACCGT CCAGGTGCTG   30540

GCCTGCCGGG AGCCGGAGGT GGACGTGGTC CTGCCCCTGC AGGTGCTGAT GCGGCGATCA   30600

CAGCGCAACT ACTTGGAGGC CCACGTTGAC CTGCGCGACT GCGTCACCTA CCAGACTGAG   30660

TACCGCTGGG AGGTGTATCG CACCGCCAGC TGCCAGCGGC CGGGGCGCCC AGCGCGTGTG   30720

GCCCTGCCCG GCGTGGACGT GAGCCGGCCT CGGCTGGTGC TGCCGCGGCT GGCGCTGCCT   30780

GTGGGGCACT ACTGCTTTGT GTTTGTCGTG TCATTTGGGG ACACGCCACT GACACAGAGC   30840

ATCCAGGCCA ATGTGACGGT GGCCCCCGAG CGCCTGGTGC CCATCATTGA GGGTGGCTCA   30900

TACCGCGTGT GGTCAGACAC ACGGGACCTG GTGCTGGATG GGAGCGAGTC CTACGACCCC   30960

AACCTGGAGG ACGGCGACCA GACGCCGCTC AGTTTCCACT GGGCCTGTGT GGCTTCGACA   31020

CAGGTCAGTG CGTGGCAGGG CCGTCCTCCA TGCCCCTCAC CCGTCCACAC CCATGAGCCC   31080

AGAGAACACC CAGCTTGCCA CCAGGGCTGG CCCGTCCTCA GTGCCTGGTG GGCCCCGTCC   31140

CAGCATGGGG AGGGGGTCTC CCGCGCTGTC TCCTGGGCCG GGCTCTGCTT TAAAACTGGA   31200

TGGGGCTCTC AGGCCACGTC GCCCCTTGTT CTCGGCCTGC AGAGGGAGGC TGGCGGGTGT   31260

GCGCTGAACT TTGGGCCCCG CGGGAGCAGC ACGGTCACCA TTCCACGGGA GCGGCTGGCG   31320

GCTGGCGTGG AGTACACCTT CAGCCTGACC GTGTGGAAGG CCGGCCGCAA GGAGGAGGCC   31380

ACCAACCAGA CGGTGGGTGC CGCCCGCCCC TCGGCCACTT GCCTTGGACA GCCCAGCCTC   31440

CCTGGTCATC TACTGTTTTC CGTGTTTTAG TGCTGGTGGA GGCCGACGC TCTCCCCTCT   31500

CTGTTTCTGA TGCAAATTCT ATGTAACACG ACAGCCTGCT TCAGCTTTGC TTCCTTCCAA   31560

ACCTGCCACA GTTCCACGTA CAGTCTTCAA GCCACATATG CTCTAGTGGC AAAAGCTACA   31620

CAGTCCCCTA GCAATACCAA CAGTGAGGAA GAGCCCCTTC CCACCCCAGA GGTAGCCACT   31680

GTCCCCAGCC CATGTCCCTG TTGCTGGATG TGGTGGGCCG GTTCTCACCC TCACGCTCCC   31740

CTCTCTGGAC CGGCCAGGAG GCTTGGTGAC CCTGAGCCCG TGGTGGCTGC TCCTGCTGCT   31800

GTCAGGCGGG GCCTGCTGGT GCCCCAGAGT GGGCGTCTGT TCCCCAGTCC CTGCTTTCCT   31860

CAGCTGGCCT GATTGGGGGT CTTCCCAGAG GGGTCGTCTG AGGGGAGGGT GTGGGAGCAG   31920

GTTCCATCCC AGCTCAGCCT CCTGACCCAG GCCCTGGCTA AGGGCTGCAG GAGTCTGTGA   31980

GTCAGGCCTA CGTGGCAGCT GCGGTCCTCA CACCCACACA TACGTCTCTT CTCACACGCA   32040

TCCCCCCAGG GGCCCTCAGT GAGCATTGCC TGCCTCCTGC TAGGGTCCAG CTGGGTCCAG   32100

TACACCAGAA CGCACACTCC AGTGTCCTCT GCCCTGTGTA TGCCCTTCCG CCGTCCAAGT   32160

TGGAAGGTGG CAAACCGGAT GAGTATCCTG GGAGGGAGTG AGCTCACCGG CAGTGGCCAG   32220

GCCCCTGGGA AACCTGGAGT TTGGGAGCAG CATCCTCCAT GGGTCCCCCA GTCCTTCCAG   32280

CAGGCCAAAT AGACCTGTGT TGGAGGTAAC CCCACTCCCA CGCCAGGTGC TGATCCGGAG   32340

TGGCCGGGTG CCCATTGTGT CCTTGGAGTG TGTGTCCTGC AAGGCACAGG CCGTGTACGA   32400

AGTGAGCCGC AGCTCCTACG TGTACTTGGA GGGCCGCTGC CTCAATTGCA GCAGCGGCTC   32460

CAAGCGAGGG GTGAGTGTTG AGCGGGGTGT GGGCGGGCTG GGGATGGGTC CCATGGCCGA   32520

GGGGACGGGG CCTGCAGGCA GAAGTGGGGC TGACAGGGCA GAGGGTTGCG CCCCCTCACC   32580
```

```
ACCCCTTCTG CCTGCAGCGG TGGGCTGCAC GTACGTTCAG CAACAAGACG CTGGTGCTGG    32640

ATGAGACCAC CACATCCACG GGCAGTGCAG GCATGCGACT GGTGCTGCGG CGGGGCGTGC    32700

TGCGGGACGG CGAGGGATAC ACCTTCACGC TCACGGTGCT GGGCCGCTCT GGCGAGGAGG    32760

AGGGCTGCGC CTCCATCCGC CTGTCCCCCA ACCGCCCGCC GCTGGGGGC TCTTGCCGCC    32820

TCTTCCCACT GGGCGCTGTG CACGCCCTCA CCACCAAGGT GCACTTCGAA TGCACGGGTG    32880

AGTGCAGGCC TGCGTGGGGG GAGCAGCGGG ATCCCCCGAC TCTGTGACGT CACGGAGCCC    32940

TCCCGTGATG CCGTGGGGAC CGTCCCTCAG GCTGGCATGA CGCGGAGGAT GCTGGCGCCC    33000

CGCTGGTGTA CGCCCTGCTG CTGCGGCGCT GTCGCCAGGG CCACTGCGAG GAGTTCTGTG    33060

TCTACAAGGG CAGCCTCTCC AGCTACGGAG CCGTGCTGCC CCCGGGTTTC AGGCCACACT    33120

TCGAGGTGGG CCTGGCCGTG GTGGTGCAGG ACCAGCTGGG AGCCGCTGTG GTCGCCCTCA    33180

ACAGGTGAGC CAGGCCGTGG GAGGGCGCCC CCGAGACTGC CACCTGCTCA CCACCCCTC    33240

TGCTCGTAGG TCTTTGGCCA TCACCCTCCC AGAGCCCAAC GGCAGCGCAA CGGGGCTCAC    33300

AGTCTGGCTG CACGGGCTCA CCGCTAGTGT GCTCCCAGGG CTGCTGCGGC AGGCCGATCC    33360

CCAGCACGTC ATCGAGTACT CGTTGGCCCT GGTCACCGTG CTGAACGAGG TGAGTGCAGC    33420

CTGGGAGGGG ACGTCACATC TGCTGCATGC GTGCTTGGGA CCAAGACCTG TACCCCTGCC    33480

TGGAGCTTTG CAGAGGGCTC ATCCCGGGCC CCAGAGATAA ATCCCAGTGA CCCTGAAGCA    33540

GCACCCCGAC CTTCCGCTCC CAGCAGCCAC ACCCACCGGG CCCTCTCCGG CGTCTGCTTT    33600

CCACAATGCA GCCCCCGCCC AGGAGGGCCC ATGTGCTTAC CCTGTTTTGC CCATGAAGAA    33660

ACAGCTCAGT GTTGTGGGTC AGTGCCCGCA TCACACAGCG TCTAGCACGT AACTGCACCC    33720

CGGGAGTCGT GGGCATCTGC TGGCCTCCTG CCGGCCTCCT GCGCTGCTGA CAGCTTGCTG    33780

TGCCCCCTGC CTGCCCCAGT ACGAGCGGGC CCTGGACGTG GCGCAGAGCC AAGCACGAG    33840

CGGCAGCACC GAGCCCAGAT ACGCAAGAAC ATCACGGAGA CTCTGGTGTC CCTGAGGGTC    33900

CACACTGTGG ATGACATCCA GCAGATCGCT GCTGCGCTGG CCCAGTGCAT GGTAGGATGG    33960

CCCCACCTGC TCACCCTGCC CCGCATGCCT GCCAGGGCAC TGGGTTCAGC CCCCCAGGGC    34020

AGACGGGCAG CTTGGCCGAG GAGCTGAGCC TCCAGCCTGG GCTCCTTCCT GCCATGGCGT    34080

TCCTCGGTCT CTGACCTGCT TCAGTAGCCT CAGCCGTTCT GTCCTGTGTG AACGCAGGGT    34140

GCCTCTCGGG GGACCCAGGG TGTAAAGAGG GGCCCAGATG TGGGGAGGGA CTAAGAAGAT    34200

GCTGCTCTGT GCCCTCCACT CTCCCCTCCC CTCCCCTCCC CCTTCCCTCC CCTAGCCCCT    34260

CCCCTCCTCC CCTCCCCTAG CCCTTCCCCT CCTCCCCTCC CCTAGCCCTT TCCCTTCTTC    34320

CCCCCCAGCC CTTCCCCTCC TCCCCTCCCC TAGCCCTTCC CCTCCTCCCC TCCCCTACCC    34380

CTTCCCCTCC TCCCCTCCCC TAGACCTTCC CCTCACCTCC TCCCGCTGAG CCCCTCCACT    34440

CGTCCCCCAG CCCCTCCCTC CCCTAGCCCC TCCCCTCCCC CTTCCTCCCC TCCTCCCCCT    34500

CCCCTCCTCC CCCTCCCTCT TCCTCCCCCT CCCCTCCTCC CCCTTCCTCC CCTCTCCTCC    34560

CCCTCCCCTC CTGTCCCCCC TCCTCCCCTC CTCCCTCCTC CCCTCCTCCC CCTCCTCCT    34620

CCCCCTCCTC CCTCCTCCCT CCTCCCCCTC CTCCTCCTCC CCTCCTCCCT CCTCCCCTCC    34680

TCCCCTCCCC TCCTCCCCCT CCCCCTCCC TTCCTCCCCC TCCCCCCTCC CCTCCTCCCC    34740

CTCTCCTCCT CCCATCCCTC CTCCCATCCC TCCTCCCCGT TCCCATTCTC TCCCCTCCCC    34800

CTTCCATTTC TCCCTCCTCC CCCTGCCCTC CTCTCCTCCT CACCTCCCCT TCTCCGCTCC    34860

TTTCTTCTCC TCCCTCCCTT TCTCTCCTCC CTCCCCTTCT CCCCTTCTCC TCTTCTCCCC    34920

TTCTCCTCTC TTTTCATCCT TCCCTTCTTC CCTCCTTTCC TCCTCTTTTC CCTCTTCTCC    34980
```

```
CCCCTCCTCC CCTCCTTCCT CCTCCCATTC CCCCTCCTCC CCCCTCCCAT TCCCCCTCCT    35040

CCCCTCCTTC CTCCTCCCAT TACCCCTCCT CTCCTCCCCT CCTCCCACCC CCCTCTCCTC    35100

CCGGCTCCTC TCCTCCCCTC CTCATCCCCC TCCTCTCCTT CCCTCCTAAC CCCCCTCCTC    35160

TCCTCCCCTC CTCATCCCCC TCCTCTCCTT CCCTCCTCCT ATCCCCCTC CTCTCCTCCC     35220

CTCCTCCTAT TCCCCCTCCT CTCCTCCCCT CCTTCCTCCT CCTCTCCTCC CATGCCCCCT    35280

CCTCCCCTCC TCCCATCCCC CTCCTCCCCT CCTCCCTCCT CCCATCCCAT CCCCCTCCTC    35340

TCCTCCCCTT CTCTCCCCTC CTCTCCTCCC CTCCTCTCCT CTCCTCCTCT CCTCCCCTCC    35400

TCCCATCCCC CCTCCTCCCA TCCCCCCTCC TCTCCTCCCC ACTCCTCTCC TCCCCACTCC    35460

TCTCCTCCCC TCATCCCCCT CCTCTCTCCT CCCCTCCCCC TCCTCTCCTT CCCTCCTCCT    35520

TTCCTCCCCT CCCCCTCCTT CCCCCTCCTC CCCCTCCTTC TCCCCATCCC CCTTCCCCTT    35580

CTCCTCCTCT CCCCTCCCCC TTCTCTTTTT CCCTCCTCCT CCCTTCCTCC TCCCCTCTTC    35640

TCCCCTTTTC CCTTTTCTCT TCCTCTCCTC CCCTTCTCCC CTCCTGTCCT CCCTCCCTTT    35700

CTCTCTTTCT TTCCTCCCTT TCCTTCTCCC CTGTTCTCCT CCCTTCCCTT CTCCCCTTTT    35760

CTTCCCTCCT CCTTTCCTCC CCTCCTCCTT TTCTCTGTTT CTCTTCCTTT CCCCTCCACT    35820

TTCCCCTTCC TTTCCCTCT CCTTTCTCCT TCCTTTCCTC TCCCCTTCTC TTCCTTTTCC     35880

TCTCTCCCCT TCTTTTCCCT CTTCCCCTCC CCTCCTCTTC CCCTCCCCTC CTCTTCCCCT    35940

CCCCTCCTCT TCCCCTCCCC TCCTCTTCCC CTCTCCTCCT CTTCCCCTCC CCTCCTCTTT    36000

CCCTCCCCTC TTCTCCTCCC CTCCTCTCCC CTCTTCCCCT CCCCTCCTCT TCCCTCCCCT    36060

TCCCCTCCCC TCCTCTTCCC TCCCCTTCCC CTCCCCTCCT CTTCCCTCCC CTTCCCCTCC    36120

TCTTCCTTCC TCTCTTCCCC TCCCCTCCTC TTCCCTCCCC TCTTCCCCTC CCCTTCTCTT    36180

CTCCTCCCCT TCTCTTCCCC TCCCCTTTTC TTCCCTCTCC TTGTCTTCCC TGCCCTCCTC    36240

TTCCCTCCCC TCCTCTTCCC TCCCCTCTTC CCCTCTCCTC CTCTTCCCTC CCCTCTTCCT    36300

CTTTCCTCTT CCCCTCCCCT CCTCCTCCCT CCCCTTTCCC CTCTTCCCCT CCCCTCCGCT    36360

TCCCTCCCCT TTCTCCCCCT TCTCTCCCCT CCCCTCTCCC CCCTTCTCTC CCCTCCCCTC    36420

TCCCCCTTCT CTCCCCTCCC CTCTCCCCCT TCTCTCCCCT CTCCTCTCCC CCTTCTCTCC    36480

CCCTTCTCTC CCCCTTCTCT CTCCCCTTCT CTCCCCCTTC TCTCCCCTCC CCCCTTCTCT    36540

CCCCTCCCCT CTCCCCCTTC TCTCCCCTCC CCTCTCCCCT GTCCTCTCCT CTCCACCCTT    36600

CTCTCCCCTC CCCTCTCCTC TCCCCCTTCC CTCTCCTCTC CCCCTTCTCT CCCCTCCCCT    36660

CTCCTCTCCC CCCTTTTCTC CACTCCCCTC TCCTCTCTCC CCTCCTCCTC CGCTCTCATG    36720

TGAAGAGGTG CCTTGTGTGG TCGGTGGGCT GCATCACGTG GTCCCCAGGT GGAGGCCCTG    36780

GGTCATGCAG AGCCACAGAA AATGCTTAGT GAGGAGGCTG TGGGGGTCCA GTCAAGTGGG    36840

CTCTCCAGCT GCAGGGCTGG GGGTGGGAGC CAGGTGAGGA CCCGTGTAGA GAGGAGGGCG    36900

TGTGCAAGGA GTGGGCCAG GAGCGGGGCT GGACACTGCT GGCTCCACAC AGGGGCCCAG     36960

CAGGGAGCTC GTATGCCGCT CGTGCCTGAA GCAGACGCTG CACAAGCTGG AGGCCATGAT    37020

GCTCATCCTG CAGGCAGAGA CCACCGCGGG CACCGTGACG CCCACCGCCA TCGGAGACAG    37080

CATCCTCAAC ATCACAGGTG CCGCGGCCCG TGCCCCATGC CACCCGCCCG CCCCGTGCGG    37140

CCCTTTCCTC TGCCTCCCTC CTCCCCCCAA CCGCGTCGCC TTTGCCCCAT CCCATCTTCG    37200

TCCCCCTCCC CTCCCCCCAA TTCCCATCCT CATCCCCCTC CCCCAATTCC CATTCTCCTC    37260

CCCCTCCCCC TTCCCTATTA CCATCCCTTT TCTCCATCTC TCTCCCCTTT TCTCCATTTC    37320
```

```
CCCCCCCGTC CTCCCCGTCC TTTTGTCCAT TCCCCTCATC TTCCTCATCC CCCTCATCCC    37380

CCTTCCCCTC CCTTATCCCC CTTCCCCTCC CTTTCCCCCT GCTCCTCTTC TTCTCCCTTC    37440

TCTTTTCTCT ACCCTTTTCC TTCCTTTTTC CTCCCTCTCC CCATCATCCC CCTCATCTTC    37500

GTCCTCATCC CCATCACCTT CCCCCTCCCC CCTCCACCAC TCTCTCTCCA GCTTCCCCCT    37560

TCCTTCTGCC TGCACCTCGC TCTCTGCCCC CTCAGGTTCC CCCTTTCTCC CAGCCCCCAC    37620

CCTCCGGCTC CCCCTTTTTG CCTGCCCCCA CCCTCCCTCT ACCTCCCTGT CTCTGCACTG    37680

ACCTCACGCA TGTCTGCAGG AGACCTCATC CACCTGGCCA GCTCGGACGT GCGGGCACCA    37740

CAGCCCTCAG AGCTGGGAGC CGAGTCACCA TCTCGGATGG TGGCGTCCCA GGCCTACAAC    37800

CTGACCTCTG CCCTCATGCG CATCCTCATG CGCTCCCGCG TGCTCAACGA GGAGCCCCTG    37860

ACGCTGGCGG GCGAGGAGAT CGTGGCCCAG GGCAAGCGCT CGGACCCGCG GAGCCTGCTG    37920

TGCTATGGCG GCGCCCCAGG GCCTGGCTGC CACTTCTCCA TCCCCGAGGC TTTCAGCGGG    37980

GCCCTGGCCA ACCTCAGTGA CGTGGTGCAG CTCATCTTTC TGGTGGACTC CAATCCCTTT    38040

CCCTTTGGCT ATATCAGCAA CTACACCGTC TCCACCAAGG TGGCCTCGAT GGCATTCCAG    38100

ACACAGGCCG GCGCCCAGAT CCCCATCGAG CGGCTGGCCT CAGAGCGCGC CATCACCGTG    38160

AAGGTGCCCA ACAACTCGGA CTGGGCTGCC CGGGGCCACC GCAGCTCCGC CAACTCCGCC    38220

AACTCCGTTG TGGTCCAGCC CCAGGCCTCC GTCGGTGCTG TGGTCACCCT GGACAGCAGC    38280

AACCCTGCGG CCGGGCTGCA TCTGCAGCTC AACTATACGC TGCTGGACGG TGCGTGCAGC    38340

GGGTGGGGCA CACGCGGCCC CCTGGCCTTG TTCTTGGGGG GAAGGCGTTT CTCGTAGGGC    38400

TTCCATGGGT GTCTCTGGTG AAATTTGCTT TCTGTTTCAT GGGCTGCTGG GGGCCTGGCC    38460

AGAGAGGAGC TGGGGGCCAC GGAGAAGCAG GTGCCAGCTC TGGTGCAGAG GCTCCTATGC    38520

TTTCAGGCCC GTGGCAGAGG GTGGGCTCAG GAGGGCCATC GTGGGTGTCC CCCGGGTGGT    38580

TGAGCTTCCC GGCAGGCGTG TGACCTGCGC GTTCTGCCCC AGGCCACTAC CTGTCTGAGG    38640

AACCTGAGCC CTACCTGGCA GTCTACCTAC ACTCGGAGCC CCGGCCCAAT GAGCACAACT    38700

GCTCGGCTAG CAGGAGGATC CGCCCAGAGT CACTCCAGGG TGCTGACCAC CGGCCCTACA    38760

CCTTCTTCAT TTCCCCGGGG TGAGCTCTGC GGGCCAGCCT GGCAGGGCAG GGCAGGGCAT    38820

CATGGGTCAG CATTGCCTGG GTTACTGGCC CCATGGGGAC GGCAGGCAGC GAGGGGACTG    38880

GACCGGGTAT GGGCTCTGAG ACTGCGACAT CCAACCTGGC GGAGCCTGGG CTCACGTCCG    38940

CTACCCCTTC CCTGCCCAGG AGCAGAGACC CAGCGGGGAG TTACCATCTG AACCTCTCCA    39000

GCCACTTCCG CTGGTCGGCG CTGCAGGTGT CCGTGGGCCT GTACACGTCC CTGTGCCAGT    39060

ACTTCAGCGA GGAGGACATG GTGTGGCGGA CAGAGGGGCT GCTGCCCCTG AGGAGACCT    39120

CGCCCCGCCA GGCCGTCTGC CTCACCCGCC ACCTCACCGC CTTCGGCGCC AGCCTCTTCG    39180

TGCCCCCAAG CCATGTCCGC TTTGTGTTTC CTGTGAGTGA CCCTGTGCTC CTGGGAGCCT    39240

CTGCAGAGTC GAGGAGGGCC TGGGTGGGCT CGGCTCTATC CTGAGAAGGC ACAGCTTGCA    39300

CGTGACCTCC TGGGCCCGGC GGCTGTGTCC TCACAGGAGC CGACAGCGGA TGTAAACTAC    39360

ATCGTCATGC TGACATGTGC TGTGTGCCTG GTGACCTACA TGGTCATGGC CGCCATCCTG    39420

CACAAGCTGG ACCAGTTGGA TGCCAGCCGG GGCCGCGCCA TCCCTTTCTG TGGGCAGCGG    39480

GGCCGCTTCA AGTACGAGAT CCTCGTCAAG ACAGGCTGGG GCCGGGGCTC AGGTGAGGGG    39540

CGCAGCGGGG TGGCAGGGCC TCCCCTGCTC TCACTGGCTG TGCTGGTTGC ACCCTCTGGG    39600

AGTGAGTCTC GTCGCAGGCG TCAGAACAAG GCAGTTTTTG CAGTGCTGTG TGAAGGGCTC    39660

GTGTGTTCAT CCTGGGAATG ACCTCGTGAG CACTCACTGT CCCTGAGGAC TAGGACAGCT    39720
```

```
CCTAGCTGGA AGTAGGTGCC AGTCAGTCAG GGTGGGCAGC CCACGTTCTG CACAGTAGCG    39780
TGGCCCCACA AGTGACGTGA GCATCGCTAC CACTGTGGGA GACTGTGCAT CCACCCGCGA    39840
TCCTGACTGC ATAGCTCGTC TCTCAGACGG AGGCGCCAGC ACCCTCCCCG TGGCTGTTTC    39900
TTCAGTACCT CCATTTTCCT TTCATTGGAA TTGCCCTTCT GGCATTCCCT TTTTGTTTTC    39960
GTTTTTCTTT TTTTAGAGAC GGAGTCTCAC TCTGTTGCCC AGGCTGGAGT GCAATGGCAT    40020
GATCTTGGCT CACAGCAACT TCCAGCTCCC GGGTTTAAGC CATTCCCCTT AAGCGATTCT    40080
CCTGAGTAGC TGGGAGTACA GGTGCACACC ACCACACCCA GTTAATTTTT CACCATGTCA    40140
GCCAGGCGAA CTCCTGACCT CAGGTGATCC GCCTGCCTCG GCCTGCCAGA GTGCTGGGAT    40200
GACAGGTGTG AGCCACCACA CCTGGCTGTG TTCCCATTTT TTATCTCTGT GCTGCTTTCC    40260
TCTTCATTGC CCAGTTCTTT CTTTTGATTA CCTACTTTTA AAAACTGTCG GCCGGGCGCG    40320
GTGGCTCACA CCTGTAATCC GAGCACTTTG GGAGGCCAGG CAGCAAATC ACGGGGTCAG     40380
GAGATCGAGA CCATCCTGGC TAACGGTGAA ACCCTGTCTC TAATAAAAAG TACAAAAAAA    40440
TTAGCCCGGC GTAGTGGCAG CGCCTGTAG TCCCAGCTCC TTGGGAGACT GAGGCAGGAG     40500
AATGGCGTGA ACCCGGGAGG CGGAGCTTGC AGTGAGCTGA GATTGCGCCA CTGCACTCCA    40560
GCCTGGGTGA CACAGCAAGA CTCCATCTCA AAAAAAAAG AAAAAAAATA CTGTCACCTG     40620
GGTCTGTCAC TGGGAGAGGA GGTGACACAG CTTCACGCTT TGCAGTCTGT GCATGAACTG    40680
AGGGACGGGT GTGTGGTGCG GGTCACCGGT TGTGGCATGA CTGAGGCGTG GACAGGTGTG    40740
CAGTGCGGGT CACTGGTTGT GGTGTGGACT GAGGCGTGTG CAGCCATGTT TGCATGTCAC    40800
AAGTTACAGT TCTTTCCATG TAACTTAATC ATGTCCTTGA GGTCCTGCTG TTAATTGGAC    40860
AAATTGCAGT AACCGCAGCT CCTTGTGTAT GGCAGAGCCG TGCAAAGCCG GGACTGCCTG    40920
TGTGGCTCCT TGAGTGCGCA CAGGCCAAAG CTGAGATGAC TTGCCTGGGA TGCCACACGT    40980
GTTGGGCAGC AGACCGAGCC TCCCACCCCT CCCTCTTGCC TCCCAGGTAC CACGGCCCAC    41040
GTGGGCATCA TGCTGTATGG GGTGGACAGC CGGAGCGGCC ACCGGCACCT GGACGGCGAC    41100
AGAGCCTTCC ACCGCAACAG CCTGGACATC TTCCGGATCG CCACCCCGCA CAGCCTGGGT    41160
AGCGTGTGGA AGATCCGAGT GTGGCACGAC AACAAAGGTT TGTGCGGACC CTGCCAAGCT    41220
CTGCCCCTCT GCCCCCGCAT TGGGGCGCCC TGCGAGCCTG ACCTCCCTCC TGCGCCTCTG    41280
CAGGGCTCAG CCCTGCCTGG TTCCTGCAGC ACGTCATCGT CAGGGACCTG CAGACGGCAC    41340
GCAGCGCCTT CTTCCTGGTC AATGACTGGC TTTCGGTGGA GACGGAGGCC AACGGGGGCC    41400
TGGTGGAGAA GGAGGTGCTG GCCGCGAGTA AGGCCTCGTT CCATGGTCCC ACTCCGTGGG    41460
AGGTTGGGCA GGGTGGTCCT GCCCCGTGGC CTCCTGCAGT GCGGCCCTCC CTGCCTTCTA    41520
GGCGACGCAG CCCTTTTGCG CTTCCGGCGC CTGCTGGTGG CTGAGCTGCA GCGTGGCTTC    41580
TTTGACAAGC ACATCTGGCT CTCCATATGG GACCGGCCGC CTCGTAGCCG TTTCACTCGC    41640
ATCCAGAGGG CCACCTGCTG CGTTCTCCTC ATCTGCCTCT TCCTGGGCGC CAACGCCGTG    41700
TGGTACGGGG CTGTTGGCGA CTCTGCCTAC AGGTGGGTGC CGTAGGGGTC GGGGCAGCCT    41760
CTTCCTGCCC AGCCCTTCCT GCCCCTCAGC CTCACCTGTG TGGCCTCCTC TCCTCCACAC    41820
AGCACGGGGC ATGTGTCCAG GCTGAGCCCG CTGAGCGTCG ACACAGTCGC TGTTGGCCTG    41880
GTGTCCAGCG TGGTTGTCTA TCCCGTCTAC CTGGCCATCC TTTTTCTCTT CCGGATGTCC    41940
CGGAGCAAGG TGGGCTGGGG CTGGGGACCC GGGAGTACTG GGAATGGAGC CTGGGCCTCG    42000
GCACCATGCC TAGGGCCGCC ACTTTCCAGT GCTGCAGCCA GAGGGAAAGG CGTCCACCAA    42060
```

```
AGGCTGCTCG GGAAGGGTCA ACACACTTGA GCAGCCTTAG CTAGACTGAC CAGGGAGAAA    42120

GAGAGAAGAC TCAGAAGCCA GAATGGTGAA AGAACGAGGG CACTTTGCTA AGCAGACGCC    42180

ACGGACGACT GCACAGCAGC ACGCCAGATA ACTCAGAAGA AGCAAGCACG CGGCTGTGCA    42240

CGCTTCCGAA ATGCACTCCA GAAGAAAATC TCAGTACATC TATAGGAAGT GAAGAGGCTG    42300

AGTTAGTCCC TTAGAAACGT CCCAGTGGCC GGGCCGGGTG TGGTGGCTCA CGCCTGTAAT    42360

CCCAACACTT CAGGTGGCCG AGGTGGGCGG ATCTGAGTCC AGGAGTTTGA GACCAGCCTG    42420

GGCAACATAG CAAGACCCCA TCTATATAAA ACATTAAAAA GGGCCAGGCG CGGTGGCTCA    42480

CGCCTGTAAT CCCAGCACTT TGGGAGGCCG AGGCGGGCAG ATCACTTGAG GTCAGGAGTT    42540

CGAGACCAGC CTGGCCAACA CAATGAAACC CCGACTCTAC TACAAATACA AAAACTTAGC    42600

TGGGCATGGT GGCGGGCGCC TGTAGTCCCA GCTACTCGAG AGGCTGAGGC AGGAGAATGG    42660

CATGAACCCA GGAGGCGGAG CTTGCAGTGA GCCGAGATTG CGCCACTGCA CTCCATCCTG    42720

GGCAACGGAG CAAGACTCCA TCTCCAAAAA AAAAAAAAA AAATCCCACA AGAAAAGCT     42780

CAGGCTCAGA GCCTTCACGA TAGAATTTTT CTAAGCAGTT AAGGAAGAAT TAACACCAAT    42840

CCTTCACAGA CTCTTTCCAA GAATACAGCA GGTGGGAACG CTTCCCATTC ATACGGAAAC    42900

GGGAGGCCGC ACCCCTTAGG AATGCACACG TGGGGTCCTC AAGAGGTTAC ATGCAAACTA    42960

ACCCCAGCAG CACACAGAGA AGGCGCATAA GCCGCGACCA GGAGGGGTTG CTCCCGAGTC    43020

CGTGGCAGGA ACCAGAGGCC ACATGTGGCT GCTCGTATTT AAGTTAATTA AAATGGAACG    43080

ATGGCCGGGT GTGGTGGCTC ACACCTGTAA TCCCAGCACT TGGGAGGCG GAGGCGGGCA     43140

GATCACTTGA GGTCAGGAGT TCCAAGACCA GCCTGGCCAA CACAGTGAAA CCCCGTCTCT    43200

ACTAAAAATA CAAAAAATTA GCTGGGCATG GTGGCAGGCA CCTGTAATCC CAGCTACTCA    43260

GGAGGCTGAG CCAGGACAAT CGCCTGAACG CGGGAGGTGG AGGTTGCAGT GAGCTGAGAT    43320

TGCGCCATTG CACTCCAGCC TGGGTGACAG CGAGACTCCA TCTAAAAAAG AAAATATGAA    43380

ATTTAAAACT CTGTTCCTTA GCTGCACCAG TCTGCTGTCA AGTGTTCAGT GGCACACGTC    43440

GCGAGGGGCT GCCATCACGG ACGGTGCAGA TGTCCCATAT ATCCAGCATT CTAGGACATT    43500

CTGTCAGATG GCACCGGGCT CTGTCCTGTC TGCTGAGGAG GTGGCTTCTC ATCCCTGTCC    43560

TGAGCAGGTC TGAGCTGCCG CCCGCTGACC ACTGCCCTCG TCCTGCAGGT GGCTGGGAGC    43620

CCGAGCCCCA CACCTGCCGG GCAGCAGGTG CTGGACATCG ACAGCTGCCT GGACTCGTCC    43680

GTGCTGGACA GCTCCTTCCT CACGTTCTCA GGCCTCCACG CTGAGGTGAG GACTCTACTG    43740

GGGGTCCTGG GCTGGGCTGG GGGTCCTGCC GCCTTGGCGC AGCTTGGACT CAAGACACTG    43800

TGCACCTCTC AGCAGGCCTT TGTTGGACAG ATGAAGAGTG ACTTGTTTCT GGATGATTCT    43860

AAGAGGTGGG TTCCCTAGAG AAACCTCGAG CCCTGGTGCA GGTCACTGTG TCTGGGGTGC    43920

CGGGGGTGTG CGGGCTGCGT GTCCTTGCTG GGTGTCTGTG GCTCCATGTG GTCACACCAC    43980

CCGGGAGCAG GTTTGCTCGG AAGCCCAGGG TGTCCGTGCG TGACTGGACG GGGTGGGCT    44040

GTGTGTGTGA CACATCCCCT GGTACCTTGC TGACCCGCGC CACCTGCAGT CTGGTGTGCT    44100

GGCCCTCCGG CGAGGGAACG CTCAGTTGGC CGGACCTGCT CAGTGACCCG TCCATTGTGG    44160

GTAGCAATCT GCGGCAGCTG GCACGGGGCC AGGCGGGCCA TGGGCTGGGC CCAGAGGAGG    44220

ACGGCTTCTC CCTGGCCAGC CCCTACTCGC CTGCCAAATC CTTCTCAGCA TCAGGTGAGC    44280

TGGGGTGAGA GGAGGGGGCT CTGAAGCTCA CCCTTGCAGC TGGGCCCACC CTATGCCTCC    44340

TGTACCTCTA GATGAAGACC TGATCCAGCA GGTCCTTGCC GAGGGGGTCA GCAGCCCAGC    44400

CCCTACCCAA GACACCCACA TGGAAACGGA CCTGCTCAGC AGCCTGTGAG TGTCCGGCTC    44460
```

```
TCGGGGAGG GGGGATTGCC AGAGGAGGGG CCGGGACTCA GGCCAGGCAG CCGTGGTTCC    44520

CGCCTGGGGT AGGGTGGGGT GGGGTGCCAG GGCAGGGCTG TGGCTGCACC ACTTCACTTC    44580

TCTGAACCTC TGTTGTCTGT GGAAAGAGCC TCATGGGATC CCCAGGGCCC CAGAACCTTC    44640

CCTCTAGGGA GGGAGCAGGC TCATGGGGCT TTGTAGGAGC AGAAAGGCTC CTGTGTGAGG    44700

CTGGCCGGGG CCACGTTTTT ATCTTGGTCT CAGAGCAGTG AGAAATTATG GGCGGGTTTT    44760

TAAATACCCC ATTTTTGGCC GGGCGCGGTG GCTCACACGT GTAATCCCAG CACTTTGGGA    44820

GGCCGAGGTG GGCAGATGAC CTGAGGTCAG CAGTTCGAGA CCAGCCTGGC CAACATGGCG    44880

AAACCCCGTC TCTACTAAAA ATACAAAAAA TTAGCCGGGC ATGCTGGCAG GCGCCTGTAG    44940

TCCCAGTTAC TCGGGAGACT GAGGTAGGAG AATCGATTGA ACCTGGTAGG TGAAGGTTGT    45000

AGTGAGCCGA GATCGCGCCA CTGCACTCCA GCCTGGGCAA CAAGAGCGAA ACTCCGTCTC    45060

AAAAACAAAA AAATTCCTCA ATTTCTTGGT TGTTTTGTAA CTTATCAACA AATGGTCATA    45120

TAGAGGTTAC CTTGTATGTA GTCACGCACA TAGTCACGCA CATGGCAGCC GGCGGCGGAG    45180

CGCACCCACG GCGTGTTCCC ACGCGTGTGA CCCCGGGCTC TGCCATGCCC TCCTATGCTC    45240

AGGTGTGCTG AGGTCCACAC GGCCCTGCCG TTGCACTGCA GCTGCCTGCA GGATTCAGTG    45300

CAGTGGCATG CAGTGCAGGT GCGGTGCCCC GGAGCCACAG GCCACACCAC AGGGCCTGCA    45360

TGCACAGGGG CTGCGGTGTC TGGGTTTGGG TAACTACGCC CTGTGACATT TGCACAGCAA    45420

CAGAATTACC TAATGACGCA TTTCTCAGAA CACATCCCTG GCACTAAGTG GTGCGTGACT    45480

GCTGCTTTTG CATCCACATC TAGTTTGATT TGTGTGTTAT TCCTTTGAGT GCTTCTCATT    45540

GTTAAGCAAC CAAGAACTAA AGAGGTATGA ACTGCCCCTG GACTCAAACA AAAAGGAAAA    45600

CTTCCTGATT TACAAAAGGC AGATAACCAT CACATGAGGG CATCTTTATG AATAAATTGC    45660

TGGTTGGTTT TAAAAATACA GAGTATGGG AAATCCAGGG GTAGTCACTA CATGCTGACC      45720

AGCCCCAGGT ATCTCCGGCC CAAAGCTCTG TGAAATCCAG ATTCAGTGCT TCCGCGGGGA    45780

TTTCTGACGG CAGCTCAGAC TCCGCATCCA CACAGAGCGC GTGGCCCTCA CCCTCCCGGC    45840

TTCCTCAACC CTTGGCCGTC CCTTGCTCGG ACAGTGCTTC GGGCTGACCA GGTCGGAGGC    45900

TTGGGTTTGT CCTGGACCCC TCTGCGTCCT TCCTCACTGC AGCCTCCAGC GCGTCCCGTG    45960

GCTCCTTTCC CAACGCAGAG CACGGCCTTC CCTGCGCCTG AGCCTGCACC CTCCGTCCTG    46020

GCGGCGCCTC TGCCCTGGCA TTCCCTGCCA CTCCATGCCT CCCTATTGGC CATTCTCCGT    46080

CTCTGCCAGC GAGAGCCTGC TCCCTGAGTC AGACCCTGAG TCATTTGTGT TGCTATAAAG    46140

GAATAGTTGA GGCTGGGTTA TTTTTTATTT TTATTTATTT TTTTGAGATG GAGTCTCTGT    46200

TGCCCAGACT GGAGTGCAGT CGCATGATCT CGGCTCACTG CAAAGTCTGC CTCCCACGTT    46260

CAAGCAGTTA TCTGCCTCAG CCTCCCAAGT AGCTAAGATT ACAGGCGCCC GCCGCCACAG    46320

CCGGCTAATT TTTTGTGTGT GTGTTTTAGT AGAGAGGAGG TTTCACCATC TTAGCCAGGC    46380

TGGTCTTGAA CTCCTGACCT CGTGATCCAC CCATCTCAGC CTCCCAAAAT GCTGAGATTA    46440

CAGGCGTGAG CCACCACGCC TGACCAAGTT GAGGCTAGGT CATTTTTTAA TTTTTTGTAA    46500

AGACAGGGTC TCACTGTCTC CAACTCCTGA GCTCAAGTGA TCCTCCTGCC TCAGCCTCCT    46560

GAAGTGCTGG GATTACAGGC TTGAGACACT GCGCCCAGCC AAGAGTGTCT TTTATCCTCC    46620

GAGAGACAGC AAAACAGGAA GCATTCAGTG CAGTGTGACC CTGGGTCAGG CCGTTCTTTC    46680

GGTGATGGGC TGACGAGGGC GCAGGTACGG GAGAGCGTCC TGAGAGCCCG GGACTCGGCG    46740

TCTCGCAGTT GGTCTCGTCC TCCCCCTCAA CGTGTCTTCG CTGCCTCTGT ACCTCTTCTC    46800
```

```
TAGCAGCTCT GGGACCGGGC ATATCAGCAT GGTGGCCCGA TGCAGTGGCA CAGCCTCGGT   46860
GGTCACTGGC TCCTGGAGAC ACAAGCAGAT CTCTGGCCTC AGGGAGCCCT ACACACTGTT   46920
GGGATTTGAA AGGCATTCAT ATGTTTCCTT GTCCAGAAGT TAATTTTAGG CCATAAACCT   46980
GCATGGGACA GACACACTGG CGTCTCTAGA TTGTAGAGAT GCTTGTTGGA TGGTTGAGAC   47040
CCAATCATAG TTTGCAGGGT TGAAGGGGGG CTCATTGCAC CCTGAGAGAC TGTGCACTGC   47100
TGTAAGGGCA GCTGGTCAGG CTGTGGGCGA TGGGTTTATC AGCAGCAAGC GGGCGGGAGA   47160
GGGACGCAGG CGGACGCCTG ACTTCGGTGC CTGGAGTGGC TCTTGGTTCC CTGGCTCCCA   47220
GCACCACTCC CACTCTCGTT TGGGGTAGGG TCTTCCGGCT TTTTGTCGGG GGGACCCTGT   47280
GACCCAAGAG GCTCAAGAAA CTGCCCGCCC AGGTTAACAT GGGCTTGGCT GCAACTGCCT   47340
CCTGGAGGCC GGGATGAATT CACAGCCTAC CATGTCCCTC AGGTCCAGCA CTCCTGGGGA   47400
GAAGACAGAG ACGCTGGCGC TGCAGAGGCT GGGGGAGCTG GGCCACCCA GCCCAGGCCT   47460
GAACTGGGAA CAGCCCCAGG CAGCGAGGCT GTCCAGGACA GGTGTGCTTG CGTAGCCCCG   47520
GGATGCCCCT AGCCCCTCCC TGTGAGCTGC CTCTCACAGG TCTGTCTCTG CTTCCCCAGG   47580
ACTGGTGGAG GGTCTGCGGA AGCGCCTGCT GCCGGCCTGG TGTGCCTCCC TGGCCCACGG   47640
GCTCAGCCTG CTCCTGGTGG CTGTGGCTGT GGCTGTCTCA GGGTGGGTGG GTGCGAGCTT   47700
CCCCCCGGGC GTGAGTGTTG CGTGGCTCCT GTCCAGCAGC GCCAGCTTCC TGGCCTCATT   47760
CCTCGGCTGG GAGCCACTGA AGGTGAGGGG GCTGCCAGGG GTAGGCTACA GGCCTCCATC   47820
ACGGGGGACC CCTCTGAAGC CACCCCCTCC CCAGGTCTTG CTGGAAGCCC TGTACTTCTC   47880
ACTGGTGGCC AAGCGGCTGC ACCCGGATGA AGATGACACC CTGGTAGAGA GCCCGGCTGT   47940
GACGCCTGTG AGCGCACGTG TGCCCCGCGT ACGGCCACCC CACGGCTTTG CACTCTTCCT   48000
GGCCAAGGAA GAAGCCCGCA AGGTCAAGAG GCTACATGGC ATGCTGCGGG TGAGCCTGGG   48060
TGCGGCCTGT GCCCCTGCCA CCTCCGTCTC TTGTCTCCCA CCTCCCACCC ATGCACGCAG   48120
GACACTCCTG TCCCCCTTTC CTCACCTCAG AAGGCCCTTA GGGGTTCAAT GCTCTGCAGC   48180
CTTTGCCCGG TCTCCCTCCT ACCCCACGCC CCCCACTTGC TGCCCCAGTC CCTGCCAGGG   48240
CCCAGCTCCA ATGCCCACTC CTGCCTGGCC CTGAAGGCCC CTAAGCACCA CTGCAGTGGC   48300
CTGTGTGTCT GCCCCCAGGT GGGGTTCCGG GCAGGGTGTG TGCTGCCATT ACCCTGGCCA   48360
GGTAGAGTCT TGGGGCGCCC CCTGCCAGCT CACCTTCCTG CAGCCACACC TGCCGCAGCC   48420
ATGGCTCCAG CCGTTGCCAA AGCCCTGCTG TCACTGTGGG CTGGGGCCAG GCTGACCACA   48480
GGGCCCCCCC GTCCACCAGA GCCTCCTGGT GTACATGCTT TTTCTGCTGG TGACCCTGCT   48540
GGCCAGCTAT GGGGATGCCT CATGCCATGG GCACGCCTAC CGTCTGCAAA GCGCCATCAA   48600
GCAGGAGCTG CACAGCCGGG CCTTCCTGGC CATCACGCGG TACGGGCATC CGGTGCACTG   48660
GTCTGTCTTC TGGGCTTTAG TTTTGCCTTT AGTCCAGCCA GACCCTAGGG GACATGTGGA   48720
CATGTGTAGA TACCTTTGTG GCTGCTAGAA CTGGAGGTAG GTGCTGCTGG CATCAGTAGG   48780
CAGAGGGGAG GGACACAGGT CCGTGTCTTG CAGTGCACAG GACGGGCCCA TGACAGACAA   48840
CTGTCTGCCC CAGAACATCC CCAGGATAAG GCTGAGAAGC CCAGGTCTAG CCGTGGCCAG   48900
CAGGGCAGTG GGAGCCATGT TCCCTGGGTC TCTGGTGGCC GCTCACTCGA GGCGGGCATG   48960
GGGCAGTAGG GGCTGGAGCG TGTGACTGAT GCTGTGGCAG GTCTGAGGAG CTCTGGCCAT   49020
GGATGGCCCA CGTGCTGCTG CCCTACGTCC ACGGGAACCA GTCCAGCCCA GAGCTGGGGC   49080
CCCCACGGCT GCGGCAGGTG CGGCTGCAGG AAGGTGAGCT GGCAGGGCGT GCCCCAAGAC   49140
TTAAATCGTT CCTCTTGTTG AGAGAGCAGC CTTTAGCGGA GCTCTGGCAT CAGCCCTGCT   49200
```

```
CCCTAGCTGT GTGACCTTTG CCCTCTTAAC ACCGCCGTTT CCTTCTCTGT ATATGAGAGA    49260

TGGTAACGTT GTCTAATTGA TGGCTGCTGG GAGGGTTCCC TGGGGTGGCG CCGAACCAGA    49320

GCTCAGGCGA GCTGGCCAGC AGGAAACACT CCTGTTGGGT TTTGATGAGG CCCTGGCCCC    49380

GGCCTGGGGC TCTGTGTGTT TCAGCACTCT ACCCAGACCC TCCCGGCCCC AGGGTCCACA    49440

CGTGCTCGGC CGCAGGAGGC TTCAGCACCA GCGATTACGA CGTTGGCTGG GAGAGTCCTC    49500

ACAATGGCTC GGGGACGTGG GCCTATTCAG CGCCGGATCT GCTGGGGTGA GCAGAGCGAG    49560

GGCCCCGGGC GTCTACGCCA AGGACAAGGG AGTAGTTCTC CAGGAGTGCC GCGGCCTCCT    49620

GACCAGCCTG GCTCCGGGGT GCCGGAAGGG CTGGGTGCG GCACCCACGC CACCCCTCTC    49680

CGGCAGGGCA TGGTCCTGGG GCTCCTGTGC CGTGTATGAC AGCGGGGCT ACGTGCAGGA    49740

GCTGGGCCTG AGCCTGGAGG AGAGCCGCGA CCGGCTGCGC TTCCTGCAGC TGCACAACTG    49800

GCTGGACAAC AGGTGGGAGC TCCCTCCCCT GCCCTCTCCG GGGTGGCCGC AGTCACCAGC    49860

CAGGAGCCCA CCCTCACTCC TCCGGCCCCC GCTGGCCTAG GCGGCTTCCA CAGCCCCTCA    49920

GCCACGCCTG CACTCGCGGG TCCCCGCAGC TCCCGCCCTG CCACCCGCTC CTACTGACCC    49980

GCACCCTCTG CGCAGGAGCC GCGCTGTGTT CCTGGAGCTC ACGCGCTACA GCCCGGCCGT    50040

GGGGCTGCAC GCCGCCGTCA CGCTGCGCCT CGAGTTCCCG GCGGCCGGCC GCGCCCTGGC    50100

CGCCCTCAGC GTCCGCCCCT TTGCGCTGCG CCGCCTCAGC GCGGGCCTCT CGCTGCCTCT    50160

GCTCACCTCG GTACGCCCGT CCCCGGCCAG ACCCCGCGCC TCCCACCGGC AGCGTCCCGC    50220

CCCCTCGCGG GGCCCCGCCC GGCAGCGTCT CACCCCTCGC AGCGCCCCGC CCCCTCGCAG    50280

CGTCCCGCCC CCTCGCAGGG CCCCGCCCCG GCAGCGTCCC GCCCCCTCGT AGGGCCCCGC    50340

CCCGGCAGCG TCCCGCCCCC TCGCAGGGCC CCGCCCGGC AGCGTCCCTC CCGCCCTCCT    50400

GACCGCGCCC CCCACAGGTG TGCCTGCTGC TGTTCGCCGT GCACTTCGCC GTGGCCGAGG    50460

CCCGTACTTG GCACAGGGAA GGGCGCTGGC GCGTGCTGCG GCTCGGAGCC TGGGCGCGGT    50520

GGCTGCTGGT GGCGCTGACG GCGGCCACGG CACTGGTACG CCTCGCCCAG CTGGGTGCCG    50580

CTGACCGCCA GTGGACCCGT TTCGTGCGCG GCCGCCCGCG CCGCTTCACT AGCTTCGACC    50640

AGGTGGCGCA GCTGAGCTCC GCAGCCCGTG GCCTGGCGGC CTCGCTGCTC TTCCTGCTTT    50700

TGGTCAAGGT GAGGGCTGGG CCGGTGGGCG CGGGGCTGGG CGCACACCCC AGGGCTGCAA    50760

GCAGACAGAT TTCTCGTCCG CAGGCTGCCC AGCAGCTACG CTTCGTGCGC CAGTGGTCCG    50820

TCTTTGGCAA GACATTATGC CGAGCTCTGC CAGAGCTCCT GGGGGTCACC TTGGGCCTGG    50880

TGGTGCTCGG GGTAGCCTAC GCCCAGCTGG CCATCCTGGT AGGTGACTGC GCGGCCGGGG    50940

AGGGCGTCTT AGCTCAGCTC AGCTCAGCTG TACGCCCTCA CTGGTGTCGC CTTCCCCGCA    51000

GCTCGTGTCT TCCTGTGTGG ACTCCCTCTG GAGCGTGGCC CAGGCCCTGT TGGTGCTGTG    51060

CCCTGGGACT GGGCTCTCTA CCCTGTGTCC TGCCGAGTCC TGGCACCTGT CACCCCTGCT    51120

GTGTGTGGGG CTCTGGGCAC TGCGGCTGTG GGGCGCCCTA CGGCTGGGGG CTGTTATTCT    51180

CCGCTGGCGC TACCACGCCT TGCGTGGAGA GCTGTACCGG CCGGCCTGGG AGCCCCAGGA    51240

CTACGAGATG GTGGAGTTGT TCCTGCGCAG GCTGCGCCTC TGGATGGGCC TCAGCAAGGT    51300

CAAGGAGGTG GGTACGGCCC AGTGGGGGGG AGAGGACAC GCCCTGGGCT CTGCCCAGGG    51360

TGCAGCCGGA CTGACTGAGC CCCTGTGCCG CCCCCAGTTC CGCCACAAAG TCCGCTTTGA    51420

AGGGATGGAG CCGCTGCCCT CTCGCTCCTC CAGGGGCTCC AAGGTATCCC CGGATGTGCC    51480

CCCACCCAGC GCTGGCTCCG ATGCCTCGCA CCCCTCCACC TCCTCCAGCC AGCTGGATGG    51540
```

```
GCTGAGCGTG AGCCTGGGCC GGCTGGGGAC AAGGTGTGAG CCTGAGCCCT CCCGCCTCCA    51600

AGCCGTGTTC GAGGCCCTGC TCACCCAGTT TGACCGACTC AACCAGGCCA CAGAGGACGT    51660

CTACCAGCTG GAGCAGCAGC TGCACAGCCT GCAAGGCCGC AGGAGCAGCC GGGCGCCCGC    51720

CGGATCTTCC CGTGGCCCAT CCCCGGGCCT GCGGCCAGCA CTGCCCAGCC GCCTTGCCCG    51780

GGCCAGTCGG GGTGTGGACC TGGCCACTGG CCCCAGCAGG ACACCCCTTC GGGCCAAGAA    51840

CAAGGTCCAC CCCAGCAGCA CTTAGTCCTC CTTCCTGGCG GGGGTGGGCC GTGGAGTCGG    51900

AGTGGACACC GCTCAGTATT ACTTTCTGCC GCTGTCAAGG CCGAGGGCCA GGCAGAATGG    51960

CTGCACGTAG GTTCCCCAGA GAGCAGGCAG GGGCATCTGT CTGTCTGTGG GCTTCAGCAC    52020

TTTAAAGAGG CTGTGTGGCC AACCAGGACC CAGGGTCCCC TCCCCAGCTC CCTTGGGAAG    52080

GACACAGCAG TATTGGACGG TTTCTAGCCT CTGAGATGCT AATTTATTTC CCCGAGTCCT    52140

CAGGTACAGC GGGCTGTGCC CGGCCCCACC CCCTGGGCAG ATGTCCCCCA CTGCTAAGGC    52200

TGCTGGCTTC AGGGAGGGTT AGCCTGCACC GCCGCCACCC TGCCCCTAAG TTATTACCTC    52260

TCCAGTTCCT ACCGTACTCC CTGCACCGTC TCACTGTGTG TCTCGTGTCA GTAATTTATA    52320

TGGTGTTAAA ATGTGTATAT TTTTGTATGT CACTATTTTC ACTAGGGCTG AGGGGCCTGC    52380

GCCCAGAGCT GGCCTCCCCC AACACCTGCT GCGCTTGGTA GGTGTGGTGG CGTTATGGCA    52440

GCCCGGCTGC TGCTTGGATG CGAGCTTGGC CTTGGGCCGG TGCTGGGGGC ACAGCTGTCT    52500

GCCAGGCACT CTCATCACCC CAGAGGCCTT GTCATCCTCC CTTGCCCCAG GCCAGGTAGC    52560

AAGAGAGCAG CGCCCAGGCC TGCTGGCATC AGGTCTGGGC AAGTAGCAGG ACTAGGCATG    52620

TCAGAGGACC CCAGGGTGGT TAGAGGAAAA GACTCCTCCT GGGGGCTGGC TCCCAGGGTG    52680

GAGGAAGGTG ACTGTGTGTG TGTGTGTGTG CGCGCGCGCA CGCGCGAGTG TGCTGTATGG    52740

CCCAGGCAGC CTCAAGGCCC TCGGAGCTGG CTGTGCCTGC TTCTGTGTAC CACTTCTGTG    52800

GGCATGGCCG CTTCTAGAGC CTCGACACCC CCCAACCCC CGCACCAAGC AGACAAAGTC    52860

AATAAAAGAG CTGTCTGACT GCAATCTGTG CCTCTATGTC TGTGCACTGG GGTCAGGACT    52920

TTATTTATTT CACTGACAGG CAATACCGTC CAAGGCCAGT GCAGGAGGGA GGGCCCCGGC    52980

CTCACACAAA CTCGGTGAAG TCCTCCACCG AGGAGATGAG GCGCTTCCGC TGGCCCACCT    53040

CATAGCCAGG TGTGGGCTCG GCTGGAGTCT GTGCAGGGGC TTTGCTATGG GACGGAGGGT    53100

GCACCAGAGG TAGGCTGGGG TTGGAGTAGG CGGCTTCCTC GCAGATCTGA AGGCAGAGGC    53160

GGCTTGGGCA GTAAGTCTGG GAGGCGTGGC AACCGCTCTG CCCACACACC CGCCCCACAG    53220

CTTGGGCAGC CAGCACACCC CGCCTGAGGG AGCCCCATAT TCCCTACCCG CTGGCGGAGC    53280

GCTTGATGTG GCGGAGCGGG CAATCCACTT GGAGGGGTAG ATATCGGTGG GGTTGGAGCG    53340

GCTATGATGC ACCTGTGAGG CCATCTGGGG ACGTAGGCAG GGGGTGAGCT CACTATCAGG    53400

TGGCACCTGG GCCTGTCCCA CCAGCTCACG CCTGGACCCA CCCCCACTCA CATTTGCGTG    53460

CAGGGCCATC TGGCGGGCCA CGAAGGGCAG GTTGCGGTCA GACACGATCT TGGCCACGCT    53520

GGTGTCCACA AGGCCCTCCA TGTCTGGGGA GACTTGGTGG TCACGCCAGG CCCAGGG      53577
```

(2) INFORMATION FOR SEQ ID NO:2:

(i) SEQUENCE CHARACTERISTICS:
        (A) LENGTH: 894 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

```
GGTGTGAGGG GTAGGGGCAG GGTGGGAGGT GGGCTCGCGG GTGGGCTGGG GTCATGAAGG      60

GCCTCAGGCG CTCTGCTATT GGGTTCCAAG GCTATCCTGA GAACAGGGGT GAGGGGGGAT     120

TGCCGTGGGG GGTTAAAGCC TTGTCATGTT CGCTTTCGGG AGATAAAAAC AACAGGTGGC     180

CTTTATGGAG ACGCTGCCCA GAGCCAGGTC TGTGCCAGGC TCCTGTTGGG GGTCGTCATG     240

CGGAATCCTG ACTCTGACCA TCCGAGGCAT AGGGACCGTG GAGATTTGCA TTTCACAGAT     300

GAGGAAACAG GTTTGGAGAG GTGACACGAC CTGTCCCAGG CATCACAGCC GGGATGTGCA     360

TAGCAGGGGT TTGGAACTAT GAGGTGCCCA GGACCCAGGG TTGGATTGAA AAGGGCGGAG     420

GGGACTAAGA TAAGCAGACA GTTGTCCCCA GCGCTGGGGA GAGTCTTGGG ACCAGTCTGA     480

TGCCTTGTAT TTCCCAGGCT CCAGGCTCCT CGCCGGGACA GTGTCTCCTT GGGTGCGTGC     540

TGGATCCCTG GGGGACGTGG CACATCCCCA GGCTTGCTAA ACATTGGGTG GGTTCTGGCA     600

TTTGGTTTTG TAACGTTTCT GGGTCACTCC CGCCTGTGGC CACCCTTCCT TAGGGGAGCC     660

GTGTGTCCTT GGGGCTTTGC TGGGTGGTCT CGAGGGTGGG AGAAGAATGG GTTCTCCTGG     720

ACCAATGGAG CCCGTGCCCC TCGGGGCCAC ATTGCTCCTG CGCTCCCTGA CTGCGGACGC     780

GTGTGTCTCG CGGCTGTCTC TGTGGAGATG GCCTCCTCCT GCCTGGCAAC AGCACCCACA     840

GAATTGCATC AGACCTACCC CACCCGTTGT TTGTGATGCT GTAGCTGAGG GCTC          894
```

(2) INFORMATION FOR SEQ ID NO:3:

(i) SEQUENCE CHARACTERISTICS:
        (A) LENGTH: 160 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

```
GGAAACAGGT TTGGAGAGGT GACACGACCT GTCCCAGGCA TCACAGCCAG GACAGGACCT      60

GTCCAGGCAT CACAGCCGGG ATGTGCATAG CAGGGGTTTG GAACTATGAG GTGCCCAGGA     120

CCCAGGGTTG GATTGAAAAG GGCGCAGGGG ACTAAGATAA                           160
```

(2) INFORMATION FOR SEQ ID NO:4:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

```
AGGACCTGTC CAGGCATC                                                    18
```

(2) INFORMATION FOR SEQ ID NO:5:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS (B) LOCATION: 1..60

(xi) SEQUENCE DESCRIPTION: SEQ ID NO:5:

```
CGC CCG CGC CGC TTC ACT AGC TTC GAC CAG GTG GCG CAC GTG AGC TCC      48
Arg Pro Arg Arg Phe Thr Ser Phe Asp Gln Val Ala His Val Ser Ser
 1               5                  10                  15

GCA GCC CGT GGC                                                      60
Ala Ala Arg Gly
            20
```

(2) INFORMATION FOR SEQ ID NO:6:

(i) SEQUENCE CHARACTERISTICS:
        (A) LENGTH: 20 amino acids
        (B) TYPE: amino acid
        (D) TOPOLOGY: linear (ii) MOLECULE TYPE: protein (xi) SEQUENCE DESCRIPTION: SEQ ID NO:6:

```
Arg Pro Arg Arg Phe Thr Ser Phe Asp Gln Val Ala His Val Ser Ser
 1               5                  10                  15

Ala Ala Arg Gly
            20
```

(2) INFORMATION FOR SEQ ID NO:7:

(i) SEQUENCE CHARACTERISTICS:
        (A) LENGTH: 20 amino acids
        (B) TYPE: amino acid
        (D) TOPOLOGY: linear (ii) MOLECULE TYPE: protein (xi) SEQUENCE DESCRIPTION: SEQ ID NO:7:

```
Arg Pro Arg Arg Phe Thr Ser Phe Asp Gln Val Ala Gln Leu Ser Ser
 1               5                  10                  15

Ala Ala Arg Gly
            20
```

(2) INFORMATION FOR SEQ ID NO:8:

(i) SEQUENCE CHARACTERISTICS:
        (A) LENGTH: 34 amino acids
        (B) TYPE: amino acid
        (D) TOPOLOGY: linear (ii) MOLECULE TYPE: peptide (xi) SEQUENCE DESCRIPTION: SEQ ID NO:8:

```
Ala Leu Thr His Gly His Ser Leu Leu Arg Asp Val Ser His Asn Leu
 1               5                  10                  15

Leu Arg Ala Leu Asp Val Gly Leu Leu Ala Asn Leu Ser Ala Leu Ala
            20                  25                  30

Glu Leu
```

(2) INFORMATION FOR SEQ ID NO:9:

(i) SEQUENCE CHARACTERISTICS:
        (A) LENGTH: 34 amino acids
        (B) TYPE: amino acid
        (D) TOPOLOGY: linear (ii) MOLECULE TYPE: peptide (xi) SEQUENCE DESCRIPTION: SEQ ID NO:9:

```
Leu His Gly Leu Lys Ala Leu Gly His Leu Asp Leu Ser Gly Asn Arg
1               5                   10                  15

Leu Arg Lys Leu Pro Pro Gly Leu Leu Ala Asn Phe Thr Leu Leu Arg
            20                  25                  30

Thr Leu
```

(2) INFORMATION FOR SEQ ID NO:10:

(i) SEQUENCE CHARACTERISTICS:
        (A) LENGTH: 34 amino acids
        (B) TYPE: amino acid
        (D) TOPOLOGY: linear (ii) MOLECULE TYPE: peptide (xi) SEQUENCE DESCRIPTION: SEQ ID NO:10:

```
Pro Ala Leu Pro Ala Arg Thr Arg His Leu Leu Ala Asn Asn Ser
1               5                   10                  15

Leu Gln Ser Val Pro Pro Gly Ala Phe Asp His Leu Pro Gln Leu Gln
            20                  25                  30

Thr Leu
```

(2) INFORMATION FOR SEQ ID NO:11:

(i) SEQUENCE CHARACTERISTICS:
        (A) LENGTH: 34 amino acids
        (B) TYPE: amino acid
        (D) TOPOLOGY: linear (ii) MOLECULE TYPE: protein (xi) SEQUENCE DESCRIPTION: SEQ ID NO:11:

```
Gly Gln Thr Leu Pro Ala Leu Thr Val Leu Asp Val Ser Phe Asn Arg
1               5                   10                  15

Leu Thr Ser Leu Pro Leu Gly Ala Leu Arg Gly Leu Gly Glu Leu Gln
            20                  25                  30

Glu Leu
```

(2) INFORMATION FOR SEQ ID NO:12:

(i) SEQUENCE CHARACTERISTICS:
        (A) LENGTH: 34 amino acids
        (B) TYPE: amino acid
        (D) TOPOLOGY: linear (ii) MOLECULE TYPE: peptide (xi) SEQUENCE DESCRIPTION: SEQ ID NO:12:

```
Thr Ala Phe Pro Val Asp Thr Thr Glu Leu Val Leu Thr Gly Asn Asn
1               5                   10                  15

Leu Thr Ala Leu Pro Pro Gly Leu Leu Asp Ala Leu Pro Ala Leu Arg
            20                  25                  30

Thr Ala
```

(2) INFORMATION FOR SEQ ID NO:13:

(i) SEQUENCE CHARACTERISTICS:
        (A) LENGTH: 34 amino acids
        (B) TYPE: amino acid
        (D) TOPOLOGY: linear (ii) MOLECULE TYPE: peptide (xi) SEQUENCE DESCRIPTION: SEQ ID NO:13:

Leu Glu His Gln Val Asn Leu Leu Ser Leu Asp Leu Ser Asn Asn Ala
1               5                   10                  15

Leu Thr His Leu Pro Asp Ser Leu Phe Ala His Thr Thr Asn Leu Thr
            20                  25                  30

Asp Leu (2) INFORMATION FOR SEQ ID NO:14:

(i) SEQUENCE CHARACTERISTICS:
        (A) LENGTH: 34 amino acids
        (B) TYPE: amino acid
        (D) TOPOLOGY: linear (ii) MOLECULE TYPE: peptide (xi) SEQUENCE DESCRIPTION: SEQ ID NO:14:

Ile Arg His Leu Arg Ser Leu Thr Arg Leu Asp Leu Ser Asn Asn Gln
1               5                   10                  15

Ile Thr Ile Leu Ser Asn Tyr Thr Phe Ala Asn Leu Thr Lys Leu Ser
            20                  25                  30

Thr Leu (2) INFORMATION FOR SEQ ID NO:15:

(i) SEQUENCE CHARACTERISTICS:
        (A) LENGTH: 34 amino acids
        (B) TYPE: amino acid
        (D) TOPOLOGY: linear (ii) MOLECULE TYPE: peptide (xi) SEQUENCE DESCRIPTION: SEQ ID NO:15:

Phe Gly Asn Met Pro His Leu Gln Trp Leu Asp Leu Ser Tyr Asn Trp
1               5                   10                  15

Ile His Glu Leu Asp Phe Asp Ala Phe Lys Asn Thr Lys Gln Leu Gln
            20                  25                  30

Leu Val (2) INFORMATION FOR SEQ ID NO:16:

(i) SEQUENCE CHARACTERISTICS:
        (A) LENGTH: 32 amino acids
        (B) TYPE: amino acid
        (D) TOPOLOGY: linear (ii) MOLECULE TYPE: peptide (xi) SEQUENCE DESCRIPTION: SEQ ID NO:16:

Gly Pro Gln His Leu Pro Leu Pro Cys Arg Asn Leu Ser Gly Asn Pro
1               5                   10                  15

Phe Glu Cys Asp Cys Gly Leu Ala Trp Leu Pro Arg Trp Ala Glu Glu
            20                  25                  30

(2) INFORMATION FOR SEQ ID NO:17:

(i) SEQUENCE CHARACTERISTICS:
        (A) LENGTH: 32 amino acids
        (B) TYPE: amino acid
        (D) TOPOLOGY: linear (ii) MOLECULE TYPE: peptide (xi) SEQUENCE DESCRIPTION: SEQ ID NO:17:

```
Gln Pro Asn Trp Asp Met Arg Asp Gly Phe Asp Ile Ser Gly Asn Pro
1               5                   10                  15

Trp Ile Cys Asp Gln Asn Leu Ser Asp Leu Tyr Arg Trp Leu Gln Ala
            20                  25                  30
```

(2) INFORMATION FOR SEQ ID NO:18:

(i) SEQUENCE CHARACTERISTICS:
        (A) LENGTH: 32 amino acids
        (B) TYPE: amino acid
        (D) TOPOLOGY: linear (ii) MOLECULE TYPE: peptide (xi) SEQUENCE DESCRIPTION: SEQ ID NO:18:

```
Thr Val Gln Gly Leu Ser Leu Gln Glu Leu Val Leu Ser Gly Asn Pro
1               5                   10                  15

Leu His Cys Ser Cys Ala Leu Arg Trp Leu Gln Arg Trp Glu Glu Glu
            20                  25                  30
```

(2) INFORMATION FOR SEQ ID NO:19:

(i) SEQUENCE CHARACTERISTICS:
        (A) LENGTH: 32 amino acids
        (B) TYPE: amino acid
        (D) TOPOLOGY: linear (ii) MOLECULE TYPE: peptide (xi) SEQUENCE DESCRIPTION: SEQ ID NO:19:

```
Phe Asp His Leu Pro Gln Leu Gln Thr Leu Asp Val Thr Gln Asn Pro
1               5                   10                  15

Trp His Cys Asp Cys Ser Leu Thr Tyr Leu Arg Leu Trp Leu Glu Asp
            20                  25                  30
```

(2) INFORMATION FOR SEQ ID NO:20:

(i) SEQUENCE CHARACTERISTICS:
        (A) LENGTH: 32 amino acids
        (B) TYPE: amino acid
        (D) TOPOLOGY: linear (ii) MOLECULE TYPE: peptide (xi) SEQUENCE DESCRIPTION: SEQ ID NO:20:

```
Phe Phe Gly Ser His Leu Leu Pro Phe Ala Phe Leu His Gly Asn Pro
1               5                   10                  15

Trp Leu Cys Asn Cys Glu Ile Leu Tyr Phe Arg Arg Trp Leu Gln Asp
            20                  25                  30
```

(2) INFORMATION FOR SEQ ID NO:21:

(i) SEQUENCE CHARACTERISTICS:
        (A) LENGTH: 32 amino acids
        (B) TYPE: amino acid
        (D) TOPOLOGY: linear (ii) MOLECULE TYPE: peptide (xi) SEQUENCE DESCRIPTION: SEQ ID NO:21:

```
Leu Asp Ala Leu Pro Ala Leu Arg Thr Ala His Leu Gly Ala Asn Pro
1               5                   10                  15

Trp Arg Cys Asp Cys Arg Leu Val Pro Leu Arg Ala Trp Leu Ala Gly
            20                  25                  30
```

(2) INFORMATION FOR SEQ ID NO:22:

(i) SEQUENCE CHARACTERISTICS:
        (A) LENGTH: 32 amino acids
        (B) TYPE: amino acid
        (D) TOPOLOGY: linear (ii) MOLECULE TYPE: peptide (xi) SEQUENCE DESCRIPTION: SEQ ID NO:22:

Leu Asn Arg Thr Met Lys Trp Arg Ser Val Lys Leu Ser Gly Asn Pro
1               5                   10                  15

Trp Met Cys Asp Cys Thr Ala Lys Pro Leu Leu Leu Phe Thr Gln Asp
            20                  25                  30

(2) INFORMATION FOR SEQ ID NO:23:

(i) SEQUENCE CHARACTERISTICS:
        (A) LENGTH: 32 amino acids
        (B) TYPE: amino acid
        (D) TOPOLOGY: linear (ii) MOLECULE TYPE: peptide (xi) SEQUENCE DESCRIPTION: SEQ ID NO:23:

Phe Glu Asp Leu Lys Ser Leu Thr His Ile Ala Leu Gly Ser Asn Pro
1               5                   10                  15

Leu Tyr Cys Asp Cys Gly Leu Lys Trp Phe Ser Asp Trp Ile Lys Leu
            20                  25                  30

(2) INFORMATION FOR SEQ ID NO:24:

(i) SEQUENCE CHARACTERISTICS:
        (A) LENGTH: 35 amino acids
        (B) TYPE: amino acid
        (D) TOPOLOGY: linear (ii) MOLECULE TYPE: peptide (xi) SEQUENCE DESCRIPTION: SEQ ID NO:24:

Thr Ala Thr Arg Trp Asp Phe Gly Asp Gly Ser Ala Glu Val Asp Ala
1               5                   10                  15

Ala Gly Pro Ala Ala Ser His Arg Tyr Val Leu Pro Gly Arg Tyr His
            20                  25                  30

Val Thr Ala
        35

(2) INFORMATION FOR SEQ ID NO:25:

(i) SEQUENCE CHARACTERISTICS:
        (A) LENGTH: 35 amino acids
        (B) TYPE: amino acid
        (D) TOPOLOGY: linear (ii) MOLECULE TYPE: peptide (xi) SEQUENCE DESCRIPTION: SEQ ID NO:25:

Val Leu Tyr Thr Trp Asp Phe Gly Asp Gly Ser Pro Val Leu Thr Gln
1               5                   10                  15

Ser Gln Pro Ala Ala Asn His Thr Tyr Ala Ser Arg Gly Thr Tyr His
            20                  25                  30

Val Arg Leu
        35

(2) INFORMATION FOR SEQ ID NO:26:

(i) SEQUENCE CHARACTERISTICS:
        (A) LENGTH: 35 amino acids
        (B) TYPE: amino acid
        (D) TOPOLOGY: linear (ii) MOLECULE TYPE: peptide (xi) SEQUENCE DESCRIPTION: SEQ ID NO:26:

```
Val Ala Tyr His Trp Asp Phe Gly Asp Gly Ser Pro Gly Gln Asp Thr
 1               5                  10                  15
Asp Glu Pro Arg Ala Glu His Ser Tyr Leu Arg Pro Gly Asp Tyr Arg
            20                  25                  30
Val Gln Val
        35
```

(2) INFORMATION FOR SEQ ID NO:27:

(i) SEQUENCE CHARACTERISTICS:
        (A) LENGTH: 35 amino acids
        (B) TYPE: amino acid
        (D) TOPOLOGY: linear (ii) MOLECULE TYPE: peptide (xi) SEQUENCE DESCRIPTION: SEQ ID NO:27:

```
Leu Ser Tyr Thr Trp Asp Phe Gly Asp Ser Ser Gly Thr Leu Ile Ser
 1               5                  10                  15
Arg Ala Pro Val Val Thr His Thr Tyr Leu Glu Pro Gly Pro Val Thr
            20                  25                  30
Ala Gln Val
        35
```

(2) INFORMATION FOR SEQ ID NO:28:

(i) SEQUENCE CHARACTERISTICS:
        (A) LENGTH: 35 amino acids
        (B) TYPE: amino acid
        (D) TOPOLOGY: linear (ii) MOLECULE TYPE: peptide (xi) SEQUENCE DESCRIPTION: SEQ ID NO:28:

```
Leu Ser Tyr Thr Trp Asp Phe Gly Asp Ser Thr Gly Thr Leu Ile Ser
 1               5                  10                  15
Arg Ala Leu Thr Val Thr His Thr Tyr Leu Glu Ser Gly Pro Val Thr
            20                  25                  30
Ala Gln Val
        35
```

(2) INFORMATION FOR SEQ ID NO:29:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:29:

CACGACCTGT CCCAGGCAT                                                       19

(2) INFORMATION FOR SEQ ID NO:30:

```
    (i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:30:

CTGGCGGGCG AGGAGAT                                               17

(2) INFORMATION FOR SEQ ID NO:31:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:31:

CTTTGACAAG CACATCT                                               17

(2) INFORMATION FOR SEQ ID NO:32:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:32:

CAACTGGCTG GACAACA                                               17

(2) INFORMATION FOR SEQ ID NO:33:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:33:

AGGACCTGTC CAGGCATC                                              18

(2) INFORMATION FOR SEQ ID NO:34:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..60

(xi) SEQUENCE DESCRIPTION: SEQ ID NO:34:

CGC CCG CGC CGC TTC ACT AGC TTC GAC CAG GTG GCG CAG CTG AGC TCC   48
Arg Pro Arg Arg Phe Thr Ser Phe Asp Gln Val Ala Gln Leu Ser Ser
 1               5                  10                  15
```

```
GCA GCC CGT GGC                                                  60
Ala Ala Arg Gly
        20

(2) INFORMATION FOR SEQ ID NO:35:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..60

(xi) SEQUENCE DESCRIPTION: SEQ ID NO:35:

GCT GCC CAG CAC GTA CGC TTC GTG CGC CAG TGG TCC GTC TTT GGC AAG    48
Ala Ala Gln His Val Arg Phe Val Arg Gln Trp Ser Val Phe Gly Lys
 1               5                  10                  15

ACA TTA TGC CGA                                                  60
Thr Leu Cys Arg
        20

(2) INFORMATION FOR SEQ ID NO:36:

(i) SEQUENCE CHARACTERISTICS:
        (A) LENGTH: 20 amino acids
        (B) TYPE: amino acid
        (D) TOPOLOGY: linear (ii) MOLECULE TYPE: protein (xi) SEQUENCE DESCRIPTION: SEQ ID NO:36:

Ala Ala Gln His Val Arg Phe Val Arg Gln Trp Ser Val Phe Gly Lys
 1               5                  10                  15

Thr Leu Cys Arg
        20

(2) INFORMATION FOR SEQ ID NO:37:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..60

(xi) SEQUENCE DESCRIPTION: SEQ ID NO:37:

GCT GCC CAG CAG CTA CGC TTC GTG CGC CAG TGG TCC GTC TTT GGC AAG    48
Ala Ala Gln Gln Leu Arg Phe Val Arg Gln Trp Ser Val Phe Gly Lys
 1               5                  10                  15

ACA TTA TGC CGA                                                  60
Thr Leu Cys Arg
        20

(2) INFORMATION FOR SEQ ID NO:38:

(i) SEQUENCE CHARACTERISTICS:
        (A) LENGTH: 20 amino acids
        (B) TYPE: amino acid
        (D) TOPOLOGY: linear
```

(ii) MOLECULE TYPE: protein (xi) SEQUENCE DESCRIPTION: SEQ ID NO:38:

Ala Ala Gln Gln Leu Arg Phe Val Arg Gln Trp Ser Val Phe Gly Lys
  1               5                  10                  15

Thr Leu Cys Arg
            20

(2) INFORMATION FOR SEQ ID NO:39:

(i) SEQUENCE CHARACTERISTICS:
            (A) LENGTH: 81 base pairs
            (B) TYPE: nucleic acid
            (C) STRANDEDNESS: single
            (D) TOPOLOGY: linear (ii) MOLECULE TYPE: cDNA (ix) FEATURE:
            (A) NAME/KEY: CDS
            (B) LOCATION: 1..81

(xi) SEQUENCE DESCRIPTION: SEQ ID NO:39:

CTG GCC ACT GGC CCC AGC AGG ACA CCT TCG GGC CAA GAA CAA GGT CCA        48
Leu Ala Thr Gly Pro Ser Arg Thr Pro Ser Gly Gln Glu Gln Gly Pro
  1               5                  10                  15

CCC CAG CAG CAC TTA GTC CTC CTT CCT GGC GGG                            81
Pro Gln Gln His Leu Val Leu Leu Pro Gly Gly
            20                  25

(2) INFORMATION FOR SEQ ID NO:40:

(i) SEQUENCE CHARACTERISTICS:
            (A) LENGTH: 27 amino acids
            (B) TYPE: amino acid
            (D) TOPOLOGY: linear (ii) MOLECULE TYPE: protein (xi) SEQUENCE DESCRIPTION: SEQ ID NO:40:

Leu Ala Thr Gly Pro Ser Arg Thr Pro Ser Gly Gln Glu Gln Gly Pro
  1               5                  10                  15

Pro Gln Gln His Leu Val Leu Leu Pro Gly Gly
            20                  25

(2) INFORMATION FOR SEQ ID NO:41:

(i) SEQUENCE CHARACTERISTICS:
            (A) LENGTH: 81 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: CDS
            (B) LOCATION: 1..64

(xi) SEQUENCE DESCRIPTION: SEQ ID NO:41:

CTG GCC ACT GGC CCC AGC AGG ACA CCC CTT CGG GCC AAG AAC AAG GTC        48
Leu Ala Thr Gly Pro Ser Arg Thr Pro Leu Arg Ala Lys Asn Lys Val
  1               5                  10                  15

CAC CCC AGC AGC ACT T AGTCCTCCTT CCTGGCG                               81
His Pro Ser Ser Thr
            20

(2) INFORMATION FOR SEQ ID NO:42:

(i) SEQUENCE CHARACTERISTICS:
        (A) LENGTH: 21 amino acids
        (B) TYPE: amino acid
        (D) TOPOLOGY: linear (ii) MOLECULE TYPE: protein (xi) SEQUENCE DESCRIPTION: SEQ ID NO:42:

```
Leu Ala Thr Gly Pro Ser Arg Thr Pro Leu Arg Ala Lys Asn Lys Val
 1               5                  10                  15

His Pro Ser Ser Thr
            20
```

POLYCYSTIC KIDNEY DISEASE GENE

This is a division, of application Ser. No. 08/381,520, filed Jan. 31, 1995 now abandoned.

This application is a continuation-in-part of U.S. patent application Ser. No. 08/323,443, filed Oct. 12, 1994 now U.S. Pat. No. 5,654,170.

FIELD OF THE INVENTION

The present invention pertains to the diagnosis and treatment of polycystic kidney disease in humans, using DNA sequences derived from the human PKD1 gene and the protein or proteins encoded by that gene.

BACKGROUND OF THE INVENTION

Autosomal dominant polycystic kidney disease (APKD), also called adult-onset polycystic kidney disease, is one of the most common hereditary disorders in humans, affecting approximately one individual in a thousand. The prevalence in the United States is greater than 500,000, with 6,000 to 7,000 new cases detected yearly (Striker et al., *Am. J. Nephrol.*, 6:161–164, 1986; Iglesias et al., *Am. J. Kid. Dis.*, 2:630–639, 1983). The disease is considered to be a systemic disorder, characterized by cyst formation in the ductal organs such as kidney, liver, and pancreas, as well as by gastrointestinal, cardiovascular, and musculoskeletal abnormalities, including colonic diverticulitis, berry aneurysms, hernias, and mitral valve prolapse (Gabow et al., *Adv. Nephrol*, 18:19–32, 1989; Gabow, *New Eng. J. Med.*, 329:332–342, 1993).

The most prevalent and obvious symptom of APKD, however, is the formation of kidney cysts, which result in grossly enlarged kidneys and a decrease in renal-concentrating ability. Hypertension and endocrine abnormalities are also common in APKD patients, appearing even before symptoms of renal insufficiency. In approximately half of APKD patients, the disease progresses to end-stage renal disease; accordingly, APKD is responsible for 4–8% of the renal dialysis and transplantation cases in the United States and Europe (*Proc. European Dialysis and Transplant Assn.*, Robinson and Hawkins, eds., 17: 20, 1981). Thus, there is a need in the art for diagnostic and therapeutic tools to reduce the incidence and severity of this discease.

APKD exhibits a transmission pattern typical of autosomal dominant inheritance, i.e. each offspring of an affected individual has a 50% chance of inheriting the causative gene. Linkage studies indicated that a causative gene is present on the short arm of chromosome 16, near the α-globin cluster; this locus was designated PKD1 (Reeders et al., *Nature*, 317:542, 1985.) Though other PKD-associated genes exist, such as, for example, PKD2, PKD1 defects appear to cause APKD in about 85–90% of affected families (Parfrey et al., *New Eng. J. Med.*, 323:1085–1090, 1990; Peters et al., *Contrib. Nephrol.*, 97:128–139, 1992).

The PKD1 gene has been localized to chromosomal position 16p13.3. Using extensive linkage analysis, in conjunction with the identification of new markers and restriction enzyme analysis, the gene has been further localized to an interval of approximately 600 kb between the markers ATPL and CMM65 (D16S84). The region is rich in CpG islands that are thought to flank transcribed sequences, and it has been estimated that this interval contains at least 20 genes. The precise location of the PKD1 gene was pinpointed by the finding of a PKD family whose affected members carry a translocation that disrupts a 14 kb RNA transcript associated with this region, as reported in the European PKD Consortium, *Cell*, 77:881, 1994. This article describes approximately 5 kb of DNA sequence corresponding to the 3' end of the putative PKD1 cDNA sequence.

Notwithstanding knowledge of the partial PKD1 3' cDNA sequence, several significant impediments stand in the way of determining the complete sequence of the PKD1 gene. For the most part, these impediments arise from the complex organization of the PKD1 locus. One serious obstacle is that sequences related to the PKD1 transcript are duplicated at least three times on chromosome 16 proximal to the PKD1 locus, forming PKD1 homologues. Another obstacle is that the PKD1 genomic interval also contains repeat elements that are present in other genomic regions. Both of these types of sequence duplications interfere with "chromosome walling" techniques that are widely used for identification of genomic DNA. This is because these techniques rely on hybridization to identify clones containing overlapping fragments of genomic DNA; thus, there is a high likelihood of "walking" into clones derived from PKD1 homologues instead of clones derived from the authentic PKD1 gene. In a similar manner, the PKD1 duplications and chromosome 16-specific repeats also interfere with the unambiguous determination of a complete cDNA sequence that encodes the PKD1 protein. Thus, there is a need in the art for genomic and cDNA sequences corresponding to the authentic PKD1 gene. This includes identification of segments of these sequences that are unique to the expressed PKD1 and not are present in the duplicated homologous sequences also present on chromosome 16.

SUMMARY OF THE INVENTION

The present invention involves an isolated normal human PKD1 gene having the sequence set forth in FIG. 1, an isolated intronless nucleic acid having the PKD1 cDNA sequence set forth in FIG. 2, and sequences derived therefrom. The PKD1 gene is a genomic DNA sequence whose altered, defective, or non-functional expression leads to adult-onset polycystic kidney disease. The invention also encompasses DNA vectors comprising these nucleic acids, cells transformed with the vectors, and methods for producing PKD1 protein or fragments thereof.

In another aspect, the invention involves isolated oligonucleotides that hybridize only to the authentic expressed PKD1 gene, and not to PKD1 homologues.

In yet another aspect, the invention involves isolated mutant PKD1 genes, and their cDNA cognates, which contain alterations in nucleotide sequence relative to the normal PKD1 gene, and whose presence in one or more copies in the genome of a human individual is associated with adult-onset polycystic kidney disease.

In still another aspect, the invention involves isolated oligonucleotides that discriminate between normal and mutant versions of the PKD1 gene.

In still another aspect, the invention involves methods for identifying a human subject carrying a mutant PKD1 gene in a human subject, comprising:

a) obtaining a sample of biological material from the subject, and b) detecting the presence of the mutant gene or its protein product.

In still another aspect, the invention involves methods and compositions for treating APKD or disease conditions having the characteristics of APKD. Such methods encompass administering an isolated human PKD1 gene, or fragments of the gene, under conditions that result in expression of therapeutically effective amounts of all, or part of, the PKD1 protein. The invention also encompasses compositions for treating APKD that comprise all or part of the PKD1 DNA of FIG. 1, or the PKD1 protein encoded by the DNA of FIG. 1.

BRIEF DESCRIPTION OF THE DRAWINGS

FIG. 1 shows the DNA sequence of 53,577 bases comprising the normal human PKD1gene SEQ ID NO: 1.

FIG. 2 shows the partial DNA sequence of 894 bases within the 5' region of normal human PKD1 cDNA SEQ ID NO: 2.

FIG. 3A shows a comparison of the DNA sequence of the 5' region of cDNAs derived from the authentic PKD1 gene and PKD1 homologues SEQ ID NO: 3. A 29-base pair gap must be introduced into the sequence of the authentic gene to align the two sequences. In addition, the authentic PKD1 cDNA and the PKD1 homologue cDNA differ at position 418 of this figure. FIG. 3B shows the DNA sequence of an oligonucleotide that can be used to discriminate between the authentic PKD1 sequence and PKD1 homologues SEQ ID NO: 4. The star denotes a polymerization-blocking modification.

FIG. 6 shows a comparison between a previously reported partial PKD1 cDNA sequence and the sequence reported herein. The upper sequence SEQ ID NO:5, 35 and 39 (DNA); SEQ ID NO:6, 36 and 40 (AA) is that reported for the cDNA while the lower sequence is the genomic sequence of the present invention SEQ ID No:7, 38 and 42 (AA). Discrepancies are highlighted by lower case in the cDNA sequence and by boxes in the genomic sequence.

FIG. 8 shows regions of homology in the PKD1 gene between sequences encoded by GRAIL2-predicted exons and proteins present in SwissProt and PIR databases. Positions where the PKD1 sequence matches the consensus sequence are shaded.

DETAILED DESCRIPTION OF THE INVENTION

Figure 4:
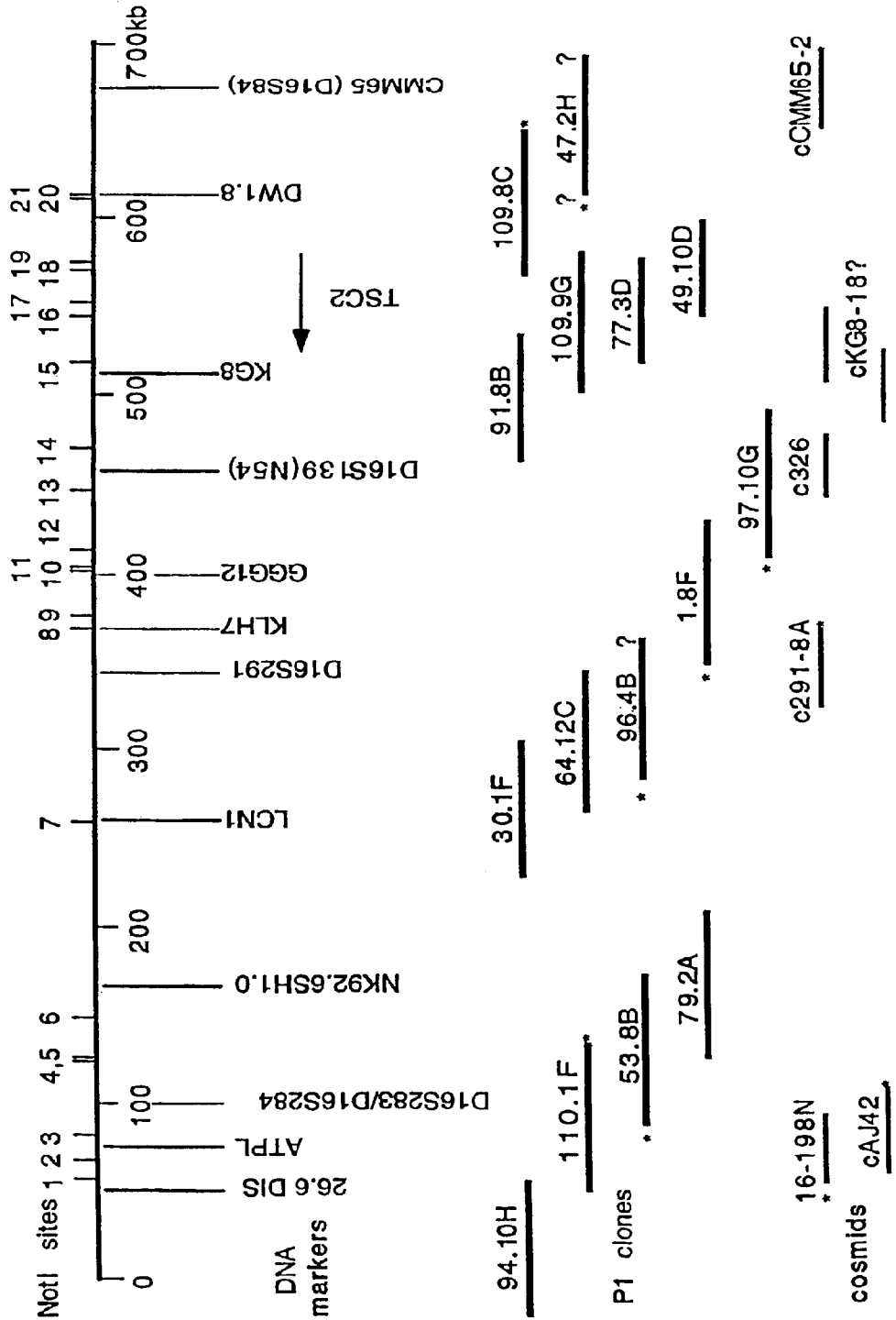
FIG. 4 shows the region of chromosome 16 containing the PKD1 locus. The upper panel shows NotI restriction sites, as well as previously identified genetic markers in this region. The bottom panel shows P1 clones covering this region.

All patent applications, patents, and literature references cited in this specification are hereby incorporated by reference in their entirety. In case of conflict or inconsistency, the present description, including definitions, will control.

Definitions:

1. "APKD" as used herein denotes adult-onset polycystic kidney disease, which is characterized by the development of renal cysts and, ultimately, renal failure, and may alternatively or in addition involve cysts in other organs including liver and spleen, as well as gastrointestinal, cardiovascular, and musculoskeletal abnormalities.

2. The term "PKD1 gene" refers to a genomic DNA sequence which maps to chromosomal position 16p13.3 and gives rise to a messenger RNA molecule encoding the PKD1 protein. The PKD1 gene encompasses the sequence shown in FIG. 1, which includes introns and putative regulatory sequences. The term "authentic" is used herein to denote the genomic sequence at this location, as well as sequences derived therefrom, and serves to distinguish these authentic sequences from "PK1homologues" (see below.)

3. "PKD1 complementary DNA (cDNA)" is defined herein as a single-stranded or double-stranded intronless DNA molecule that is derived from the authentic PKD1 gene and whose sequence, or complement thereof, encodes the PKD1 protein.

4. A "normal" PKD1 gene is defined herein as a PKD1 gene whose altered, defective, or non-functional expression leads to adult-onset polycystic kidney disease. A normal PKD1 gene is not associated with disease and thus is considered to be a wild-type version of the gene. Included in this category are allelic variants in the PKD1 gene, also denoted allelic polymorphisms, i.e. alternate versions of the PKD1 gene, not associated with disease, that may be represented at any frequency in the population. Also included are alterations in DNA sequence, whether recombinant or naturally occurring, that have no apparent effect on expression or function of the PKD1 gene product.

5. A "mutant" PKD1 gene is defined herein as a PKD1 gene whose sequence has been modified by transitions, transversions, deletions, insertions, or other modifications relative to the normal PKD1 gene, which modifications cause detectable changes in the expression or function of the PKD1 gene product, including causing disease. The modifications may involve from one to as many as several thousand nucleotides, and result in one or more of a variety of changes in PKD1 gene expression, such as, for example, decreased or increased rates of expression, or expression of a defective RNA transcript or protein product. Mutant PKD1 genes encompass those genes whose presence in one or more copies in the genome of a human individual is associated with APKD.

6. A "PKD1 homologue" is a sequence which is closely related to PKD1, but which does not encode the authentic expressed PKD1 gene product. Several examples of such homologues that map to chromosomal location 16p13.1 have been identified and sequenced by the present inventors.

7. A "PKD1 carrier" is defined herein as an individual who carries at least one copy of a disease-producing mutant PKD1 gene. Since the disease generally exhibits an autosomal dominant pattern of transmission, PKD1 carriers have a high probability of developing some symptom of PKD. Thus, a PKD1 carrier is likely to be a "PKD patient."

8. As referred to herein, a "contig" is a continuous stretch of DNA or DNA sequence, which may be represented by multiple, overlapping, clones or sequences.

9. As referred to herein, a "cosmid" is a DNA plasmid that can replicate in bacterial cells and that accommodates large DNA inserts from about 30 to about 45 kb in length.

10. The term "P1 clones" refers to genomic DNAs cloned into vectors based on the P1 phage replication mechanisms. These vectors generally accomodate inserts of about 70 to about 105 kb (Pierce et al., *Proc. Natl. Acad. Sci., USA*, 89:2056–2060, 1992).

11. As used herein, the term "exon trapping" refers to a method for isolating genomic DNA sequences that are flanked by donor and acceptor splice sites for RNA processing.

12. The term "single-strand conformational polymorphism analysis" (SSCP) refers to a method for detecting sequence differences between two DNAs, comprising hybridization of the two species with subsequent mismatch detection by gel electrophoresis. (Ravnik-Glavac et al., *Hum. Mol. Genet.*, 3:801, 1994.)

13. "HOT cleavage" is defined herein as a method for detecting sequence differences between two DNAs, comprising hybridization of the two species with subsequent mismatch detection by chemical cleavage (Cotton, et al., *Proc. Natl. Acad. Sci., USA*, 85:4397, 1988).

14. "Denaturing gradient gel electrophoresis" (DDGE) refers to a method for resolving two DNA fragments of identical length on the basis of sequence differences as small as a single base pair change, using electrophoresis through a gel containing varying concentrations of denaturant (Guldberg et al., *Nuc. Acids Res.*, 22:880, 1994.)

15. As used herein, "sequence-specific oligonucleotides" refers to related sets of oligonucleotides that can be used to detect allelic variations or mutations in the PKD1 gene.

16. As used herein, "PKD1-specific oligonucleotides" refers to oligonucleotides that hybridize to sequences present in the authentic expressed PKD1 gene and not to PKD1 homologues or other sequences.

17. "Amplification" of DNA as used herein denotes a reaction that serves to increase the concentration of a particular DNA sequence within a mixture of DNA sequences. Amplification may be carried out using polymerase chain reaction (PCR; Saiki et al., *Science*, 239:487, 1988), ligase chain reaction (LCR), nucleic acid-specific based amplification (NSBA), or any method known in the art.

18. "RT-PCR" as used herein refers to coupled reverse transcription and polymerase chain reaction. This method of amplification uses an initial step in which a specific oligonucleotide, oligo dT, or a mixture of random primers is used to prime reverse transcription of RNA into single-stranded cDNA; this cDNA is then amplified using standard amplification techniques e.g. PCR.

19. A PKD1 gene or PKD1 cDNA, whether normal or mutant, corresponding to a particular sequence is understood to include alterations in the particular sequence that do not change the inherent properties of the sequence. It will be understood that additional nucleotides may be added to the 5' and/or 3' terminus of the PKD1 gene shown in FIG. 1, or the PKD1 cDNA shown in FIG. 2, as part of routine recombinant DNA manipulations. Furthermore, conservative DNA substitutions, i.e. changes in the sequence of the protein-coding region that do not change the encoded amino acid sequence, may also be accommodated.

The present invention encompasses the human gene for PKD1. Mutations in this gene are associated with the occurrence of adult-onset polycystic kidney disease. A "normal" version of the genomic sequence, corresponding to 53,577 bases of the 5' end of the PKD1 gene is shown in FIG. 1.

The PKD1 gene sequence was determined using the strategy described in Example 1. Briefly, a series of cosmid and P1 DNA clones was assembled containing overlapping human genomic DNA sequences that collectively cover a 750 kilobase segment of chromosome 16 known to contain the PKD1 locus. To identify transcribed sequences within this 750 kb segment, including those sequences encoding PKD1, both exon trapping and cDNA selection techniques were employed. At the same time, direct DNA sequencing of the human DNA sequences contained in the genomic clones was performed, using techniques that are well-known in the art. These included the isolation of subclones from particular cosmid or P1 clones. Nested deletions were created from selected subclones, and the nested deletions were then subjected to direct DNA sequencing using the ALF™ automated sequencer (Pharmacia, Uppsala, Sweden).

A partial sequence of PKD1 cDNA is shown in FIG. 2. This 5' cDNA is fragment, comprising 894 bases, spans nucleotides 4378 to 5271 of the sequence shown in FIG. 1.

The present invention encompasses isolated oligonucleotides corresponding to sequences within the PKD1 gene, or within PKD1 cDNA, which, alone or together, can be used to discriminate between the authentic expressed PKD1 gene and PKD1 homologues or other repeated sequences. These oligonucleotides may be from about 12 to about 60 nucleotides in length, preferably about 18 nucleotides, may be single- or double-stranded, and may be labelled or modified as described below. An example of an oligonucleotide that can be used in this manner is shown in FIG. 3B. The discrimination function of this oligonucleotide is based on a comparison of the sequence of the authentic PKD1 gene with three cDNAs derived from the PKD1 homologues, which revealed that homologue cDNAs contain a 29 bp insertion relative to the authentic PKD1 sequence (FIG. 3A). The oligonucleotide shown in FIG. 3B is modified at its 3' terminus so that it does not support polymerization reactions, and is designed to hybridize specifically to the homologue sequence and not to the authentic PKD1 sequence. When this oligonucleotide is included in amplification reactions, it selectively prevents the amplification of PKD1 homologue sequences. In this manner, authentic PKD1 sequences are selectively amplified and PKD1 homologues are not. These oligonucleotides or their functional equivalents thus provide a basis for testing for the presence of mutations in the authentic PKD1 gene in a human patient (see Example 3 below).

The present invention encompasses isolated DNA and RNA sequences, including sense and antisense sequences, derived from the sequences shown in FIGS. 1, 2, and 3. The particular sequences may represent "normal" alleles of PKD1, including allelic variants, or "mutant" alleles, which are associated with disease symptoms. PKD1-derived sequences may also be associated with heterologous sequences, including promoters, enhancers, response elements, signal sequences, polyadenylation sequences, and the like. Furthermore, the nucleic acids can be modified to alter stability, solubility, binding affinity, and specificity. For example, PKD1-derived sequences can be selectively methylated.

The DNA may comprise antisense oligonucleotides, and may further include nuclease-resistant phosphorothioate, phosphoroamidate, and methylphosphonate derivatives, as well as "protein nucleic acid" (PNA) formed by conjugating bases to an amino acid backbone as described in Nielsen et al., 1991, *Science*, 254: 1497. The DNA may be derivatized by linkage of the a-anomer nucleotide, or by formation of a methyl or ethyl phosphotriester or an alkyl phosphoramidate linkage. Furthermore, the nucleic acid sequences of the present invention may also be modified with a label capable of providing a detectable signal, either directly or indirectly. Exemplary labels include radioisotopes, fluorescent molecules, biotin, and the like.

In general, nucleic acid manipulations according to the present invention use methods that are well known in the art, as disclosed in, for example, *Molecular Cloning, A Laboratory Manual* (2nd Ed., Sambrook, Fritsch and Maniatis, Cold Spring Harbor), or *Current Protocols in Molecular Biology* (Eds. Ausubel, Brent, Kingston, More, Feidman, Smith and Stuhl, Greene Publ. Assoc., Wiley-Interscience, NY, N.Y., 1992).

The invention also provides vectors comprising nucleic acids having PKD1 or PKD1-related sequences. A large number of vectors, including plasmid and fungal vectors, have been described for expression in a variety of eukaryotic and prokaryotic hosts, and may be used for gene therapy as well as for simple protein expression. Advantageously, vectors may also include a promoter operably linked to the PKD1 encoding portion, particularly when the PKD1-encoding portion comprises the cDNA shown in FIG. 2 or derivatives or fragments thereof. The encoded PKD1 may be expressed by using any suitable vectors, such as pREP4, pREP8, or pCEP4 (InVitrogen, San Diego, Calif.), and any suitable host cells, using methods disclosed or cited herein or otherwise known to those skilled in the relevant art. The particular choice of vector/host is not critical to the operation of the invention.

Recombinant cloning vectors will often include one or more replication systems for cloning or expression, one or more markers for selection in the host, e.g. antibiotic resistance, and one or more expression cassettes. The inserted PKD1 coding sequences may be synthesized, isolated from natural sources, or prepared as hybrids, for example. Ligation of the PKD1 coding sequences to transcriptional regulatory elements and/or to other amino acid coding sequences may be achieved by known methods. Suitable host cells may be transformed/transfected/infected by any suitable method including electoporation, $CaCl_2$ mediated DNA uptake, fungal infection, microinjection, microprojectile, or other established methods.

Appropriate host cells included bacteria, archebacteria, fungi, especially yeast, and plant and animal cells, especially mammalian cells. Of particular interest are *E. coli, B. Subtilis, Saccharomyces cerevisiae*, SF9 cells, C129 cells, 293 cells, *Neurospora*, and CHO cells, COS cells, HeLa cells, and immortal mammalian myeloid and lymphoid cell lines. Preferred replication systems include M13, Co1E1, SV40, baculovirus, lambda, adenovirus, artificial chromosomes, and the like. A large number of transcription initiation and termination regulatory regions have been isolated and shown to be effective in the transcription and translation of heterologous proteins in the various hosts. Examples of these regions, methods of isolation, manner of manipulation, and the like, are known in the art. Under appropriate expression conditions, host cells can be used as a source of recombinantly produced PKD1.

This invention also contemplates the use of unicellular or multicellular organisms whose genome has been transfected or transformed by the introduction of PKD1 coding sequences through any suitable method, in order to obtain recombinantly produced PKD1 protein or peptides derived therefrom.

Nucleic acids encoding PKD1 polypeptides may also be incorporated into the genome of recipient cells by recombination events. For example, such a sequence can be microinjected into a cell, and thereby effect homologous recombination at the site of an endogenous gene encoding PKD1, an analog or pseudogene thereof, or a sequence with substantial identity to a PKD1-encoding gene. Other recombination-based methods such as nonhomologous recombinations or deletion of endogenous gene by homologous recombination, especially in pluripotent cells, may also be used.

The present invention also encompasses an isolated polypeptide having a sequence encoded by the authentic PKD1 gene, as well as peptides of six or more amino acids derived therefrom. The polypeptide(s) may be isolated from human tissues obtained by biopsy or autopsy, or may be produced in a heterologous cell by recombinant DNA methods as described above. Standard protein purification methods may be used to isolate PKD1-related polypeptides, including but not limited to detergent extraction, and chromatographic methods including molecular sieve, ion-exchange, and affinity chromatography using e.g. PKD1-specific antibodies or ligands. When the PKD1-polypeptide to be purified is produced in a recombinant system, the recombinant expression vector may comprise additional sequences that encode additional aminoterminal or carboxy-terminal amino acids; these extra amino acids act as "tags" for immunoaffinity purification using immobilized antibodies or for affinity purification using immobilize ligands.

Peptides comprising PKD1-specific sequences may be derived from isolated larger PKD1 polypeptides described above, using proteolytic cleavages by e.g. proteases such as trypsin and chemical treatments such as cyanogen bromide that are well-known in the art. Alternatively, peptides up to 60 residues in length can be routinely synthesized in milligram quantities using commercially available peptide synthesizers.

The present invention encompasses antibodies that specifically recognize the PKD1 polypeptide(s) encoded by the gene shown in FIG. 1 or the cDNA shown in FIG. 2, and/or fragments or portions thereof. The antibodies may be polyclonal or monoclonal, may be produced in response to the native PKD1 polypeptide or to synthetic peptides as described above. Such antibodies are conveniently made using the methods and compositions disclosed in Harlow and Lane, *Antibodies, A Laboratory Manual*, Cold Spring Harbor laboratory, 1988, other references cited herein, as well as immunological and hybridoma technologies known to those in the art. Where natural or synthetic PKD1-derived peptides are used to induce a PKD1-specific immune response, the peptides may be conveniently coupled to an suitable carrier such as KLH and administered in a suitable adjuvant such as Freunds. Preferably, selected peptides are coupled to a lysine core carrier substantially according to the methods of Tam, *Proc. Natl. Acad. Sci, USA* 85:5409–5413, 1988. The resulting antibodies may be modified to a monovalent form, such as, for example, Fab, $Fab_2$, FAB', or FV. Anti-idiotypic antibodies may also be prepared using known methods.

In one embodiment, normal or mutant PKD1 polypeptides are used to immunize mice, after which their spleens are removed, and splenocytes used to form cell hybrids with myeloma cells and obtain clones of antibody-secreted cells according to techniques that are standard in the art. The resulting monoclonal antibodies are screened for specific binding to PKD1 proteins or PKD1-related peptides.

In another embodiment, antibodies are screened for selective binding to normal or mutant PKD1 sequences. Antibodies that distinguish between normal and mutant forms of PKD1 may be used in diagnostic tests (see below) employing ELISA, EMIT, CEDIA, SLIFA, and the like. Anti-PKD1 antibodies may also be used to perform subcellular and histochemical localization studies. Finally, antibodies may be used to block the function of the PKD1 polypeptide, whether normal or mutant, or to perform rational drug design studies to identify and test inhibitors of the function (e.g., using an anti-idiotypic antibody approach.)

Identification of Disease-Causing Mutations in PKD1

In one mode of practice of the present invention, the isolated and sequenced PKD1 gene is utilized to identify previously unknown or mutant versions of the PKD1 gene. First, human subjects with inherited polycystic kidney disease are identified by clinical testing, pedigree analysis, and linkage analysis, using standard diagnostic criteria and interview procedures, and DNA or RNA samples are obtained from the subjects (see below).

A variety of techniques are then employed to pinpoint new mutant sequences. First, PKD1 DNA may be subjected to direct DNA sequencing, using methods that are standard in the art. Furthermore, deletions may be detected using a PCR-based assay, in which pairs of oligonucleotides are used to prime amplification reactions and the sizes of the amplification products are compared with those of control products. Other useful techniques include Single-Strand Conformation Polymorphism analysis (SSCP), HOT cleavage, denaturing gradient gel electrophoresis, and two-dimensional gel electrophoresis.

A confounding and complicating factor in the detection of a PKD1 mutation is the presence of PKD1 homologues at several sites on chromosome 16 proximal to the transcribed gene. In analysis of mutations in PKD1, it is critical to distinguish between sequences derived from the authentic PKD1 gene and sequences derived from any of the homologues. Thus, an important feature of the present invention is the provision of oligonucleotide primers that discriminate between authentic PKD1 and the homologues. A detailed comparison of the sequences of the authentic PKD1 gene and the homologues enables the design of primers that discriminate between the authentic PKD1 gene or cDNA and the homologues. Primers that conform to this criterion, such as those disclosed in FIG. 3B, may be used in conjunction with any of the analytical methods described below.

For SSCP, primers are designed that amplify DNA products of about 250–300 bp in length across non-duplicated segments of the PKD1 gene. For each amplification product, one gel system and two running conditions are used. Each amplification product is applied to a 10% polyacrylamide gel containing 10% glycerol. Separate aliquots of each amplimer are subjected to electrophoresis at 8 W at room temperature for 16 hours and at 30 W at 4° C. for 5.4 hours. These conditions were previously shown to identify 98% of the known mutations in the CFTR gene (Ravnik-Glavac et al., *Hum. Mol. Genet.*, 3:801, 1994.)

For "HOT" cleavage, amplification reactions are performed using radiolabelled PKD1-specific primers. Each radiolabelled amplification product is then mixed with a 10-fold to 100-fold molar excess of unlabelled amplification products produced using the identical primers and DNA from APKD-affected or -unaffected subjects. Heteroduplex formation, chemical cleavage, and gel analysis are then performed as described (Cotton, et al., *Proc. Natl. Acad. Sci., USA*, 85:4397, 1988). Bands on the gel that are smaller than the homoduplex result from chemical cleavage of heteroduplexes at base pair mismatches involving cytidine or thymidine. Once a mutation has been identified by this procedure, the exact location of the mismatch(es) is determined by direct DNA sequencing.

Mutations are also identified by "broad range" DDGE (Guldberg et al., *Nuc. Acids Res.*, 22:880, 1994.) The use of GC-clamped PCR primers and a very broad denaturant gradient enables the efficient detection of mutant sequences. This method can also be combined with non-denaturing size fractionation in a two-dimensional system. An apparatus is used that permits automated two-dimensional electrophoresis, and the second dimension considerably increases the resolution of mutations.

After the presence of a mutation is detected by any of the above techniques, the specific nucleic acid alteration comprising the mutation is identified by direct DNA sequence analysis. In this manner, previously unidentified PKD1 mutations may be defined.

Once a previously unidentified PKD1 mutation is defined, methods for detecting the particular mutation in other affected individuals can be devised, using a variety of methods that are standard in the art. For example, oligonucleotide probes may be prepared that allow the detection and discrimination of the particular mutation. It will be understood that such probes may comprise either the mutant sequence itself, or, alternatively, may flank the mutant sequence. Furthermore, the oligonucleotide sequence can be used to design a peptide immunogen comprising the mutant amino acid sequence. These peptides are then used to elicit antibodies that distinguish between normal and mutant PKD1 polypeptides.

Diagnostic Tests for PKD1 Mutations

Mutant PKD1 genes, whether identified by the methods described above or by other means, find use in the design and operation of diagnostic tests. Tests that detect the presence of mutant PKD1 genes, including those described below and in Example 3, can be applied in the following ways:

(1) To determine donor suitability for kidney transplants. In general, it is desirable to use a close relative of the transplant recipient. When the recipient is a patient suffering from familial APKD, it is important to ascertain that the donor relative does not also carry the familial mutant PKD1 gene.

(2) To screen for at-risk individuals is APKD-affected families. Presymptomatic individuals who have a high probability of developing APKD can be identified, allowing them to be monitored and to avail themselves of preventive therapies.

(3) To target hypertensive patients for antihypertensive treatment. Hypertension is also linked to APKD. Screening of hypertensive patients for the presence of mutant PKD1 genes can be used to identify patients for preemptive regulation of blood pressure to prevent later kidney damage.

(4) To perform prenatal screening. Most PKD1-linked PKD is of the adult-onset type. In a small subset of families carrying a mutation in PKD1 genes, however, juvenile onset is common and signifies a more severe form of the disease. In these families, prenatal screening can be useful for genetic counselling purposes.

In general, the diagnostic tests according to the present invention involve obtaining a biological sample from a subject, and screening the sample, using all or part of the PKD1 gene of this invention, for the presence of one or more mutant versions of the PKD1 gene or its protein product. The subject may be a fetus in utero, or a human patient of any age.

In one embodiment, a sample of genomic DNA is obtained from a human subject and assayed for the presence of one or more disease-associated PKD1 mutations. This DNA may be obtained from any cell source or body fluid. Non-limiting examples of cell sources available in clinical practice include blood cells, buccal cells, cervicovaginal cells, epithelial cells from urine, fetal cells, or any cells present in tissue obtained by biopsy. Body fluids include blood, urine, cerebrospinal fluid, amniotic fluid, and tissue exudates at the site of infection or inflammation. DNA is extracted from the cell source or body fluid using any of the numerous methods that are standard in the art. It will be understood that the particular method used to extract DNA will depend on the nature of the source. The minimum amount of DNA to be extracted for use in the present invention is about 25 pg (corresponding to about 5 cell equivalents of a genome size of $4 \times 10^9$ base pairs).

In this embodiment, the assay used to detect the presence of mutations may comprise restriction enzyme digestion, direct DNA sequencing, hybridization with sequence-specific oligonucleotides, amplification by PCR, single-stranded conformational polymorphism analysis, denaturating gradient gel electrophoresis (DDGE), two-dimensional gel electrophoresis, in situ hybridization, and combinations thereof.

In a preferred embodiment, RNA is isolated from a PKD1-expressing cell or tissue, preferably lymphocytes, using standard techniques including automated systems such as that marketed by Applied Biosystems, Inc. (Foster City, Calif.). The RNA is then subjected to coupled reverse-transcription and PCR amplification (RT-PCR). The resulting DNA may then be screened for the presence of mutant sequences by any of the methods outlined above (see Example 3 below).

As discussed above, any nucleic-acid-based screening method for PKD1 mutations must be able to discriminate between the authentic PKD1 gene present at chromosome location 16p13.3 and PKD1 homologues present at 16p13.1 and other locations. The oligonucleotides shown in FIG. 3 are examples of primers that discriminate between the authentic and homologue sequences, and these oligonucleotides or their equivalents form an important part of any such diagnostic test. Furthermore, nucleotides 43,818 through 52,882 of the PKD1 sequence of FIG. 1 represent a sequence that is unique to the authentic PKD1 gene and is not present in the homologues. Thus, oligonucleotides derived from this region can be used in a screening method to insure that the authentic PKD1 gene, and not the homologues, are detected.

In another embodiment, the assay used to detect the presence of a mutant PKD1 gene involves testing for mutant gene products by an immunological assay, using one of many methods known in the art, such as, for example, radioimmunoassay, ELISA, immunofluorescence, and the like. In this embodiment, the biological sample is preferably derived from a PKD1-expressing tissue such as kidney. The PKD1 polypeptide may be extracted from the sample. Alternatively, the sample may be treated to allow detection or visualization of specifically bound antibodies in situ as occurs in, for example, cryosectioning followed by immunofluorescent staining.

The antibodies may be monoclonal or polyclonal, may be raised against intact PKD1 protein, or natural or synthetic peptides derived from PKD1. In a preferred embodiment, the antibodies discriminate between "normal" and "mutant" PKD1 sequences, and possess a sufficiently high affinity for PKD1 polypeptides so that they can be used in routine assays.

It will be understood that the particular method or combination of methods used will depend on the particular application. For example, high-throughput screening methods preferably involve extraction of DNA or RNA from an easily available tissue, followed by amplification of particular PKD1 sequence and hybridization of the amplification products with a panel of specific oligonucleotides.

Therapeutic Applications

The present invention encompasses the treatment of PKD using the methods and compositions disclosed herein. All or part of the normal PKD1 gene disclosed above can be delivered to kidney cells or other affected cells using a variety of known methods, including e.g. liposomes, viral vectors, recombinant viruses, and the like. The gene can be incorporated into DNA vectors that additionally comprise tissue-specific regulatory elements, allowing PKD1 expression in a tissue-specific manner. This approach is feasible if a particular mutant PKD1 allele, when present in a single copy, merely causes the level of the PKD1 protein to diminish below a threshold level necessary for normal function; in this case, increasing the gene dosage by supplementing with additional normal copies of the PKD1 gene should correct the functional defect. In another embodiment, a mixture of isolated nucleic acids, such as that set forth in FIG. 2 and at least a portion of the normal PKD1 gene, may be delivered to kidney or other affected cells in order to treat APKD. Alternatively, it may be desired to limit the expression of a mutant PKD1 gene, using, for example, antisense sequences. In this embodiment, antisense oligonucleotides may be delivered to kidney or other cells.

For therapeutic uses, PKD1-related DNA may be administered in any convenient way, for example, parenterally in a physiologically acceptable carrier such as phosphate buffered saline, saline, deionized water, or the like. Typically, the compositions are added to a retained physiological fluid such as blood or synovial fluid. The amount administered will be empirically determined using routine experimentation. Other additives, such as stabilizers, bactericides, and the like, may be included in conventional amounts.

This invention also encompasses the treatment of APKD by protein replacement. In one embodiment, protein produced by host cells transformed or transfected with DNA encoding the PKD1 polypeptide of the present invention is introduced into the cells of an individual suffering from altered, defective, or non-functional expression of the PKD1 gene. This approach augments the absence of PKD1 protein, or the presence of a defective PKD1 protein, by adding functional PKD1 protein. The PKD1 protein used in augmentation may comprise a subcellular fragment or fraction, or may be partially or substantially purified. In any case, the PKD1 protein is formulated in an appropriate vehicle, such as, for example, liposomes, that may additionally include conventional carriers, excipients, stabilizers, and the like.

It will be understood that the therapeutic compositions of the present invention need not in themselves constitute an effective amount, since such effective amounts can be reached by administering a plurality of such therapeutic compositions.

The following examples are intended to illustrate the invention without limiting its scope thereof.

EXAMPLE 1

Cloning and Sequencing of the Human PKD1 Gene

A. Methods:

Ordered restriction fragments were subcloned into either pBLUEscript (Stratagene, LaJolla, Calif.) or pGEM (Promega, Madison, Wis.). Plasmids were purified by CsCl density centrifugation in the presence of ethidium bromide. Nested deletions were generated from each plasmid using ExoIII (Henikoff, S., *Methods Enzymol.* 155: 156–165, 1987) and additional enzymatic reagents provided by the Erase-A-Base kit (Promega, Madison, Wis.). The resulting nested clones were analyzed electrophoretically after appropriate restriction enzyme digestion and were ordered into a nested set of templates for sequencing. A minimum tiling series of plasmids, each differing by approximately 250 bp from flanking clones, were identified and used for sequencing.

Plasmid DNAs were prepared for sequencing in one of two ways. Initially, all clones of interest were cultured in 2 mL of Super Broth (Tartof et al., *BRL Focus* 9: 12, 1987) for 20 hours at 37° C. Sets of 12–24 were processed simultaneously using a modified alkaline SDS procedure followed by ion exchange chromatography as described by the manufacturer Easy-Prep, Pharmacia, Piscataway, N.J.). Plasmid DNA yields ranged from 2.5 to 25 μg. Poor growing clones, or those whose plasmids generated sequence of unacceptable quality, were recultured in 100 mL of Luria's Broth and the plasmid DNA isolated using Qiagen columns (Qiagen, San Diego, Calif.).

Dideoxy sequencing reactions were performed on deletion clones using the Auto-Read Sequencing Kit (Pharmacia, Piscataway, N.J.) and fluorescein-labeled vector primers (M13 universal, M13 reverse, T3, T7 and SP6). Reaction products were separated on 6% denaturing acrylamide gels using the ALF DNA Sequencer (Pharmacia, Piscataway, N.J.). Second strand sequencing was performed using either an opposing set of nested deletions or primer walking. For primer waling, custom 17mers, staggered every 250 bp, were purchased from a commercial supplier (Protogene, Palo Alto, Calif.). Template DNAs prepared by Qiagen or CsCl density gradients were sequenced using the unlabeled 17mers by inclusion of fluor-dATP labeling mix in the sequencing reactions as described by the manufacturer (Pharmacia, Piscataway, N.J.). In all cases, except the 2.5 kb GC-rich region, single-stranded DNA was rescued from deletion clones using helper phage VCSM13 (Stratagene) essentially as described by the manufacturer. Single-stranded templates from the 2.5 kb GC-rich region were sequenced using fluorescein-labeled universal primer and the Sequitherm Long Read cycle sequencing kit (Epicentre Technologies, Madison, Wis.) (Zimmerman et al., Biotechniques 17: 303–307, 1994). All processed sequencing data was transferred to a Quadra 700 Macintosh computer and assembled using the SEQUENCHER (Gene Codes, Ann Arbor, Mich.) sequencing assembly program. For differences that would not be resolved by examining the chromatograms, is templates were either resequenced or primers proximal to the ambiguity were designed and used for resolution of the sequence difference. Cycle sequencing was performed using the Sequitherm cycle sequencing kit as described by the manufacturer (Epicentre Technologies, Madison, Wis.). Reaction products were separated on denaturing acrylamide gels and subsequently detected by autoradiography.

Figure 5:
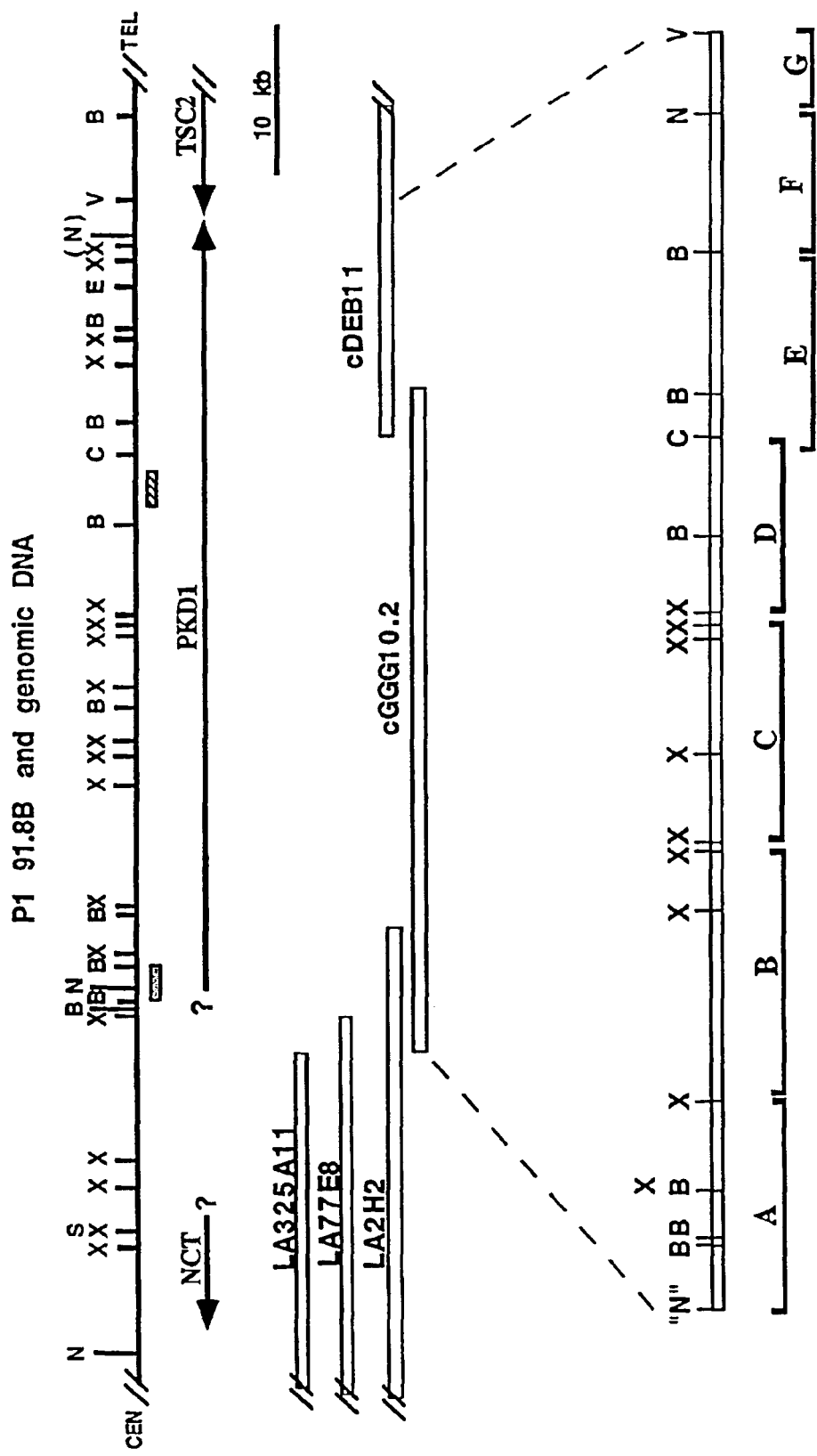
FIG. 5 shows a restriction map of a P1 clone designated 91.8B, which contains the authentic PKD1 gene.

B. Sequencing Strategy:

A 700 kbp region of chromosome 16 containing the PKD1 locus is shown in FIG. 4 (top panel). A contig covering this region was assembled from overlapping P1 clones (shown in the middle panel). The contig was assembled by unidirectional chromosomal walking from the ends of the interval (ATPL and D16S84) and bidirectional walking from several internal loci (D16S139 and KG8). One of the clones, 91.8B, appears to span the entire PKD1 interval and includes cosmids cDEB11, cGGG10.2 and substantial portions of cosmids 2H2 and 325A11 (Stallings, R. L. et al.; Genomics 13:1031, 1992). This P1 clone (shown schematically in FIG. 5) was used as a second genomic template to confirm discrepancies between the published cDNA sequence and the cosmid-derived genomic sequence.

Preliminary experiments revealed the presence of multiple repetitive elements in the cGGG10.2 cosmid. Therefore, an ordered approach based on nested deletions, rather than random shotgun subcloning, was used to sequence the PKD1 gene. Restriction fragments derived from the inserts of both cGGG10.2 and cDEB11 were subcloned into high-copy number plasmids as a preliminary step to the generation of nested deletions. Unidirectional deletions were prepared and sequenced, using the ALF™ automated sequencing system (Pharmacia, Uppsala, Sweden).

Read lengths averaged 350 nucleotides, with runs greater than 500 nucleotides being common. This strategy allowed for the rapid and accurate sequencing of 53,577 nucleotides of linear gene sequence using 1,200 sequencing reactions. Based on this analysis, the cumulative fold-redundancy is approximately 7-fold. Intervals of minimum redundancy (3-fold) showed perfect sequence identity between overlapping templates. The only exception to complete double-stranded sequencing was the 2.5 kb GC-rich region in the 4 kb BamH1-SacI fragment, and an adjoining 150 bp GC-rich region in the adjacent Sac1-BamH1 fragment. These segments were only sequenced on the non-coding strand due to complications arising from the repetitive nature of the sequences in this region.

In this manner, the sequence of PKD1 genomic DNA shown in FIG. 1 was obtained.

C. Primary Structure of the PED1 Locus:

The primary sequence of the interval encompassing the PKD1 gene is 53,577 bp in length. The locus is GC-rich (62.4%), with a CpG/GpC dinucleotide ratio of 0.485. Comparison of this sequence with the previously reported partial cDNA sequence revealed differences at three locations (FIG. 6). The first and most significant difference is the presence of two additional cytosine residues on the plus strand at position 4566 of the reported sequence. This sequence difference was confirmed using sequence derived from cDNA originating from a different individual. In addition, allele-specific oligonucleotides (ASOs) homologous to either the reported sequence or the present sequence were hybridized to the genomic and cDNA clones. In all cases, dot-blot analysis using single-base discrimination conditions showed that only the ASO containing the additional cytosine residues hybridized to all cloned DNAs. The presence of these two cytosine residues results in a frame shift in the predicted protein coding sequence, leading to the replacement of 92 carboxy terminal amino acids with a novel 12-amino acid carboxy terminus. Seven of the twelve amino acids, of the new carboxy terminus are charged or polar. Additional sequence differences are located at positions 3639–3640 and 3708–3709 of the published sequence (FIG. 6). A GC dinucleotide pair is present at each of these positions in the present sequence, while a CG pair is found in the reported sequence. In each case, histidine and valine residues would replace the previously predicted glutamine and leucine residues, respectively. It is unclear at present if these latter differences represent allelic variation or errors in the reported sequence.

It is clear that the previously reported cDNA sequence provides an inaccurate sequence with an incorrect reading frame. Any proteins encoded by the prior partial sequence would thus be defective, and would in no way suggest proteins encoded by the sequence of the present invention, or indeed the sequence itself. It follows that employ of the prior sequence, or of proteins encoded thereby, in therapeutic or diagnostic uses would not be successful.

Figure 7:
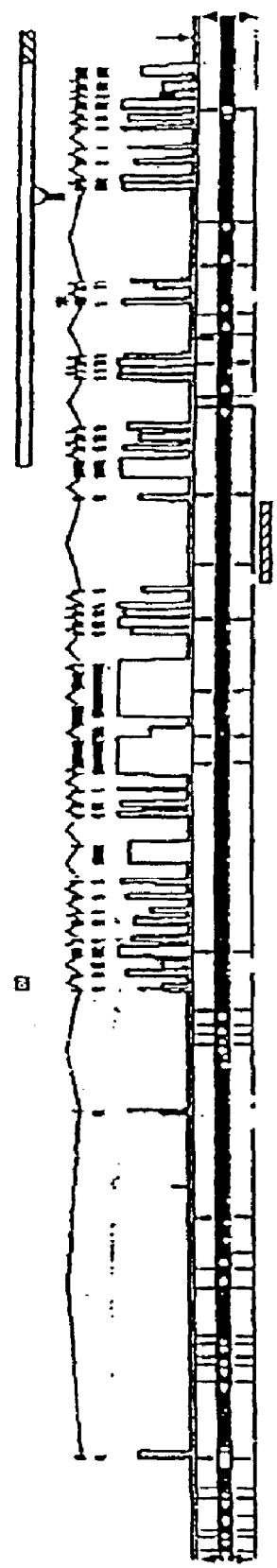
FIG. 7 shows an illustration of the PKD1 genomic structure as predicted by GRAIL2. The predicted exons are represented as boxes along the genomic sequence. The reported cDNA is at the top right. The position of the 2.5 kb GC-rich region is indicated by the striped box at the bottom.

The entire sequence was analyzed for transcriptional elements and CpG islands using GRAIL2 (Uberbacher, E. C. et al., Proc. Natl. Acad. Sci. USA 88:11261, 1991) and XGrail client server (Shah et al., User's Guide to GRAIL and GENQUEST, Client-Server Systems, available by anonymous ftp to arthur.epm.omi.gov (128.219.9.76) from directory pub/xgrail or pub/xgenquest, as file manual.grail-genquest, 1994). Ten CpG islands were identified (FIG. 7). Forty-eight exons were predicted on the coding strand by the GRAIL program. The quality of 39 of the 48 exons was "excellent", six were considered "good", and three were deemed "marginal". These data were analyzed using the gene model feature of GRAIL2. The final gene model contained 46 exons. When the accuracy of the gene model was examined by comparison to the published cDNA, 22 of 23 exons in the published cDNA were predicted in the model. Of the 22 exons present in the gene model, 16 were correctly spliced, four were wholly contained in the model but used either an incorrect 5' or 3' splice site, and in one case two exons were combined into a single exon in the model (with the program failing to remove a small intron). Only one of the deduced exons in the published cDNA was absent from the gene model.

D. Identification of Protein Coding Regions:

Exons predicted by the GRAIL2 program with an "excellent" score were used to search the SwissProt and PIR databases using the BLASTP program. Exons 3 and 4 of the gene model were predicted to encode peptides with homology to a number of leucine-rich repeat (LRR)-containing proteins involved in protein-protein interactions (FIG. 8). In addition to the LRR itself, sequences amino- and carboxy-flanking to the LRR may also be conserved in proteins of the leucine-rich glycoprotein (LRG) family, either singly or together. Exon 3 encodes residues homologous to the LRR from leucine-rich α2 glycoprotein, members of the GP1b.IX complex which comprise the von Willebrand factor receptor, as well as to the Drosophila proteins chaoptin, toll, and slit. The latter are involved in adhesion, dorsal-ventral polarity, and morphogenesis, respectively. Sequences predicted by GRAIL2 to be encoded by exon 4 were found to have homology to the conserved region carboxy terminal to the LRR in all of the above proteins except chaoptin, which lacks this conserved region. Homology was also observed between the exon 4-encoded sequences and the trk proto-oncogene, which encodes a receptor for nerve growth factor. Further examination of the predicted PKD1 peptide revealed additional regions of weaker homology with conserved regions of the trk tyrosine kinase domain. None of the more proximal exons in the gene model appear to encode a peptide with homology to the conserved amino-flanking region seen in a subset of the LRR-containing proteins.

Exon trapping, RT-PCR, and Northern blot analysis revealed that GRAIL2-predicted exons 3 and 4 are present in expressed sequences. During initial exon trapping experiments using genomic P1 and cosmid clones from the PKD1 locus, an exon trap was identified that contained both of these exons. In separate experiments, the presence of the LRR-carboxy-flanking motif in transcribed sequences was confirmed by RT-PCR using as a template RNA from fetal kidney and from adult brain. On the Northern blot, an RT-PCR fragment containing this motif detected the 14 kb PKD1 transcript and several other transcripts of 21 kb, 17 kb, and 8.5 kb.

A region of homology was also observed between the GRAIL2-predicted peptide and the human gp100/PmeI17 gene products, as well as with bovine RPE1. The gp100/PmeI 17 gene encodes two alternately spliced products (gp10 and PmeI17) that differ by only 7 amino acids. Closer examination indicated that this region of homology was present in sequences encoded by three separate GRAIL-predicted exons; however, only the exon containing the first copy of the motif is fully contained within the final gene model.

GRAIL2-predicted exons 9, 22, and 28, upstream of the 3' cDNA, showed strong homology to EST T03080 (85%, 255 bp), EST T04943 (98%, 189 bp) and EST T05931 (94%, 233 bp). In addition, nucleotides 10378–10625 of GRAIL-predicted intron 1 showed strong homology to a region of the Apo CII gene (81%, 263 bp).

E. Repeated Sequences:

The PKD1 locus was searched for known classes of repetitive DNA by FASTA comparison against the repeat database of Jurka et al. (*J. Mol. Evol.* 35:286–291, 1992). This search identified 23 Alu repeats but no other repetitive elements. The Alu repeats are organized into three clusters of four or more Alu repeats, three clusters of two alu repeats, and two singlet Alu repeats (FIG. 7). The average density of Alu repeats per kb is 0.4. The three clusters of four or more Alu repeats are positioned within the first 20,000 nucleotides (0.85 Alu per kb) and are predominantly on the reverse strand (15 of 17). Intervals 20,000–40,000 and 47,000–54,000 are devoid of Alu repeats.

The sequence interval contained two dinucleotide repeats (>(TG)8) and a single tetranucleotide repeat ((TTTA)6). The TG dinucleotide repeats are present at positions 209–224 and 52,693–52,708. The tetranucleotide repeat is located at position 7795–7810. No trinucleotide repeats >5 were identified. Only the TG8 repeat is known to be polymorphic.

In addition to the more usual repetitive elements, the PKD1 gene contains several types of repeated sequences that either do not appear in existing data bases, or do not appear in the extreme form seen at this locus. The most striking repeat is a 2.5 kb segment within the 4 kb BamH1-Sac1 fragment. A significantly shorter C-T rich region is also found in the adjoining 1.8 kb Sac1-BamH1 fragment. These regions proved very difficult to sequence unambiguously due to the high GC content (65 %), to the purine asymmetry with respect to each strand and to the length of the repeat. The coding strand in this region has an extreme pyrimidine bias, being 96 % C-T, and could not be sequenced using T7 DNA polymerase or Sequenase. This was true regardless of the template type (plasmid, single-stranded phage, or strand-separated single-stranded DNA). In both cases, the noncoding strand, which is G-A rich, was successfully sequenced with both T7 DNA polymerase and Sequenase, although run lengths were noticeably abbreviated compared to all other regions sequenced. Compressions on the non-coding strand were resolved by conventional and cycle sequencing using single-stranded template. The extreme purine assymetry of strands in this segment may promote localized triple strand conformation under the appropriate conditions (pH, divalent cations, supercoiling), and may be a major cause of the difficulty in sequencing this segment.

The other unusual repeat was located in the 7.6 kb XhoI fragment. This repeat is 459 bp in length and consists of 17 tandem copies of a perfect 27 bp repeat.

EXAMPLE 2

PKD1 cDNA Sequences Obtained through Exon Trapping and cDNA Selection Techniques The 700 kbp interval of chromosome 16 that includes the PKD1 gene appears to be particularly rich in CpG islands and, by association, is most likely rich in expressed sequences as well. To purify and sequence expressed PKD1 sequences, an exon-rescue vector, pSPL3, was used to recover sequences from cosmids that contain both a splice acceptor and splice donor element; this method is designated "exon trapping." The application of this method, in conjunction with standard subcloning, amplification, and DNA sequencing methods, allowed the determination of PKD1 cDNA sequence as shown in FIG. 2.

Exon trapping is a highly efficient method for isolating expressed sequences from genomic DNA. The procedure utilizes the pSPL3 plasmid, which contains rabbit δ-globin coding sequences separated by a portion of the HIV-tat gene, or improved derivatives of SPL3 lacking cryptic (interfering) splice sites. Fragments of cloned PKD1 genomic DNA were cloned into the intron of the tat gene, and the resulting subclones were transfected into COS-7 cells. SV40 sequences in the vector allow for both relaxed episomal replication of the transfected vectors, as well as transcription of the cloned genomic DNAS. Exons within the subcloned genomic DNAs spliced into the globin/tat transcript were recovered using RT-PCR, using primers containing tat splice donor and acceptor sequences. A major advantage of exon trapping is that expression of the cloned DNA is directed by a viral promoter; thus, developmental or tissue-specific expression of gene products is not a concern.

PKD1-containing genomic clones, in the form of either cosmid or P1 DNA, were either double digested with BamHI and BglII or partially digested with Sau3A and shotgun cloned into BamHI-digested and dephosphorylated pSPL3 (GIBCO BRL, Bethesda, Md.) or its derivatives. Plasmid minipreps were electroporated into COS-7 cells, and trapped exons were recovered by RT-PCR, followed by subcloning, using standard procedures.

Figure 9:
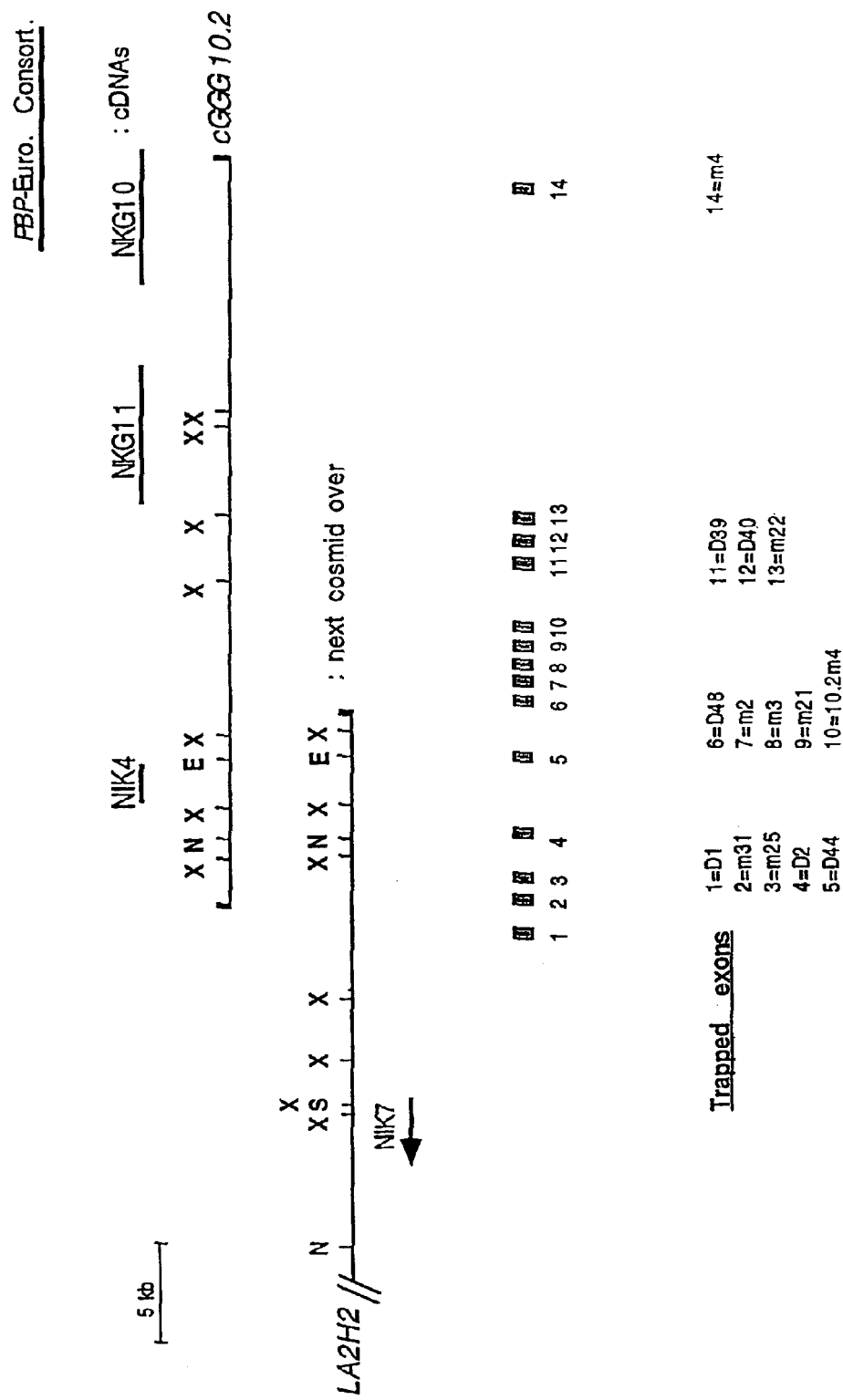
FIG. 9 shows the results of exon trapping within the PKD1 locus.

Trapped exons from the PKD1 locus are shown in FIG. 9 (bottom). The trapped exons were subjected to automated DNA sequencing as above, allowing their alignment with the genomic PKD1 DNA.

EXAMPLE 3

Diagnostic Test for PKD1 Mutations

Whole blood samples collected in high glucose ACD Vacutainers™ (yellow top) were centrifuged and the buffy coat collected. The white cells were lysed with two washed of a 10:1 (v/v) mixture of 14 mM $NH_4Cl$ and 1 mM $NaHCO_3$, their nuclei were resuspended in nuclei-lysis buffer (10 mM Tris, pH 8.0, 0.4 M NaCl, 2 mM EDTA, 0.5% SDS, 500 ug/ml proteinase K) and incubated overnight at 37° C. Samples were then extracted with a one-fourth volume of saturated NaCl and the DNA was precipitated in ethanol. The DNA was then washed with 70% ethanol, dried, and dissolved in TE buffer (10 mM Tris-HCl, pH 7.5, 1 mM EDTA.)

0.2–1 µg of DNA (in 1–2 µl) was then added to a PCR reaction mixture containing the following components:

| | | |
|---|---|---|
| 10X Taq buffer | 8 µl | |
| dNTPS (2 mM each) | 7 µl | |
| Forward primer (100 µM) | 1.5 µl | |
| Reverse primer (100 µM) | 1.5 µl | |
| Blocking oligo (2 mM) | 1.5 µl | |
| Taq DNA polymerase | 1 µl | |
| water | to 80 µl | |

Thirty cycles of amplification are then performed, using a standard DNA thermal cycler the following protocol for each cycle: 94° C., 30 seconds; 55° C., 30 seconds; and 72° C., 30 seconds. It will be understood that the enzymes and nucleotides used in the above reactions may be obtained from any manufacturer, such as GIBCO-BRL, Promega, New England Biolabs, and the like.

The forward primer used in the reaction described above comprises an oligonucleotide that hybridizes to both authentic PKD1 and PKD1 homologue sequences. An example of such a primer is: 5'-CACGACCTGTCCCAGGCAT-3' SEQ ID No: 29. The reverse primer comprises a sequence derived from a 3' region of the authentic PKD1 gene, which may or may not be present in the PKD1 homologues. Examples of suitable reverse primers are:

5'-CTGGCGGGCGAGGCAGAT-3' SEQ ID No: 30, 5'-CTTTGACAAGCACATCT-3' SEQ ID No:31, and 5'-CAACTGGCTGGACAACA-3' SEQ ID No:32.

The blocking oligonucleotide comprises: 5'-AGGACCTGTCCAGGCATC-3' SEQ ID No: 33 Importantly, this oligonucleotide must be incapable of supporting polymerization. One example is an oligonucleotide in which the 3' terminal nucleotide comprises a dideoxynucleotide. It will be understood that any modification that achieves this effect may be used in practicing the invention. Under appropriate conditions, the blocking oligonucleotide hybridizes efficiently to PKD1 homologues but inefficiently to the authentic PKD1 sequence. Thus, the amplification products in this diagnostic test are derived only from the authentic PKD1 gene.

The RT-PCR products obtained above are analyzed for the presence of specific PKD1 mutations as follows:

8 µl of the amplified prepared as describe above are added to 50 µl of a denaturing solution (0.5M NaOH, 2.0M NaCl, 25 mM EDTA) and spotted onto nylon membrane filters (INC Biotrans). The DNA is then fixed to the membranes by baking the filters at 80° C. for 15 minutes under vacuum.

Oligonucleotides that detect PKD1 mutations are chemically synthesized using an automated synthesizer and radio-labelled with $^{32}P$ with polynucleotide kinase, using methods that are standard in the art.

Hybridizations are carried out in plastic bags containing the filters prepared as in Example 1D above, to which one dr more labelled oligonucleotides are added in a hybridization buffer (3.0M Tetramethylammonium chloride (TMAC), 0.6% SDS, 1 mM EDTA, 10 mM sodium phosphate pH 6.8, 5×Denhardt's Solution, and 40 µg/ml yeast RNA). Oligonucleotide concentrations in the pools range from 0.03 to 0.15 pmol/ml hybridization solution.

Hybridizations are allowed to proceed overnight at 52° C., with agitation. The membranes are then removed from the bags and washed for 20 min at room temperature with wash buffer (3.0M TMAC, 0.6% SDS, 1 mM EDTA, 10 mM sodium phosphate pH 6.8), followed by a second wash in the same buffer for 20 min at 52° C. The membranes are then dried and exposed to Kodak X-OMAT film.

While the present invention has been described with respect to what are presently considered to be the preferred embodiments, it is to be understood that the invention is not limited to the disclosed embodiments. To the contrary, the invention is intended to cover various modifications and equivalent arrangements included within the spirit and scope of the appended claims. The scope of the following claims is to be accorded the broadest interpretation so as to encompass all such modifications and equivalent structures and functions.

What is claimed:

1. A composition for treating cyst formation associated with APKD, said composition comprising an isolated human PKD1 gene having the DNA sequence of SEQ ID NO:1, its complement, or fragments thereof, and a pharmaceutically acceptable carrier or diluent.

2. The composition of claim 1 comprising a vector into which said PKD1 gene is incorporated.

3. The composition of claim 1, wherein said isolated human PKD1 gene comprises an intronless nucleic acid sequence derived from the DNA sequence of SEQ ID NO:1, its complement or fragments thereof, wherein said intronless nucleic acid sequence is a cDNA.

* * * * *